United States Patent
Zhang et al.

(10) Patent No.: US 7,803,956 B2
(45) Date of Patent: Sep. 28, 2010

(54) BENZOFURAN DERIVATIVES USEFUL FOR TREATING HYPER-PROLIFERATIVE DISORDERS

(75) Inventors: Chengzhi Zhang, Orange, CT (US); Jacques Dumas, Bethany, CT (US); Gaetan H. Ladouceur, Guilford, CT (US); Qian Zhao, Wallingford, CT (US); Martin F. Hentemann, Hamden, CT (US); Sharad K. Verma, New Haven, CT (US); Qingming Zhu, Malden, MA (US); Rico C. Lavoie, Cheshire, CT (US); Jianmei Fan, Newton, MA (US); Barton Phillips, New Haven, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 12/471,335

(22) Filed: May 22, 2009

(65) Prior Publication Data

US 2009/0292014 A1 Nov. 26, 2009

Related U.S. Application Data

(60) Continuation of application No. 12/201,547, filed on Aug. 29, 2008, now Pat. No. 7,659,412, which is a division of application No. 10/566,343, filed as application No. PCT/US2004/025480 on Aug. 6, 2004, now Pat. No. 7,420,066.

(60) Provisional application No. 60/494,165, filed on Aug. 7, 2003.

(51) Int. Cl.
  *C07D 307/87* (2006.01)
  *A01N 43/12* (2006.01)
  *A01N 43/08* (2006.01)

(52) U.S. Cl. .................. 549/462; 514/443; 514/470

(58) Field of Classification Search .................. 549/462; 514/443, 470
See application file for complete search history.

(56) References Cited

U.S. PATENT DOCUMENTS 7,585,888 B2 * 9/2009 Zhang et al. ................. 514/443

FOREIGN PATENT DOCUMENTS

| EP | 0 731 097 A1 | 9/1996 |
| WO | 03/072561 A1 | 9/2003 |

OTHER PUBLICATIONS

Hayakawa, I., et al., "4-Hydroxy-3-Methyl-6-Phenylbenzofuran-2-Carboxylic Acid Ethyl Ester Derivatives as Potent Anti-Tumor Agents," Bioorganic & Medicinal Chemistry Letters 14(2):455-458, Jan. 2004.

Hayakawa, I., et al., "A Library Synthesis of 4-Hydroxy-3-Methly-6-Phenylbenzofuran-2-Carboxylic Acid Ethyl Ester Derivatives as Anti-Tumor Agents," Bioorganic & Medicinal Chemistry Letters 14(17):4383-4387, Sep. 2004.

Hayakawa, I., et al., "Thienopyridine and Benzofuran Derivatives as Potent Anti-Tumor Agents Possessing Different Structure-Activity Relationships," Bioorganic & Medicinal Chemistry Letters 14(13):3411-3414, Jul. 2004.

* cited by examiner

*Primary Examiner*—D. Margaret Seaman
*Assistant Examiner*—Nizal S Chandrakumar
(74) *Attorney, Agent, or Firm*—Christensen O'Connor Johnson Kindness PLLC

(57) ABSTRACT

The invention relates to novel benzofuran derivatives, processes for their preparation and their use for preparing medicaments for the treatment or prophylaxis of disorders, especially of hyperproliferative disorders.

19 Claims, No Drawings

BENZOFURAN DERIVATIVES USEFUL FOR TREATING HYPER-PROLIFERATIVE DISORDERS

CROSS-REFERENCES TO RELATED APPLICATIONS

This application is a continuation of U.S. patent application Ser. No. 12/201,547, filed Aug. 29, 2008, which is a divisional of U.S. patent application Ser. No. 10/566,343, filed Aug. 6, 2004, now U.S. Pat. No. 7,420,066, which is a U.S. National Stage of International Patent Application No. PCT/US2004/025480, filed Aug. 6, 2004, which claims the benefit of U.S. Provisional Application No. 60/494,165, filed Aug. 7, 2003. Each application is expressly incorporated herein by reference in its entirety.

FIELD OF THE INVENTION

This invention relates to novel benzofuran derivative compounds, pharmaceutical compositions containing such compounds and the use of those compounds and compositions for the treatment of hyper-proliferative disorders.

Biorg. Med. Chem. Lett., 14 (2004) 45-458, Biorg. Med. Chem. Lett., 14 (2004) 3411-3414 and Biorg. Med. Chem. Lett., 14 (2004) 4383-4387 describe benzofuran derivatives for the treatment of cancer. "Synthetic 2-Arylindole Derivatives as a New Class of Potent Tubulin-Inhibitory, Antimitotic Agents", and J. Med. Chem. 44, 2001, 4535-4553, describe 2-arylindole derivatives for the treatment of cancer. WO 2003/072561 and WO 2003/072566 relate to the treatment of cancer, while EP-A1-19960911 relates to the treatment of inflammation.

DESCRIPTION OF THE INVENTION

One embodiment of the present invention relates to a compound of formula (I)

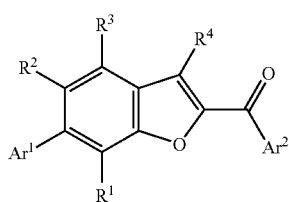

(I)

wherein $Ar^1$ is selected from benzodioxolyl, pyrrolidinyl,
pyridyl or pyridyl N-oxide, each optionally mono-substituted with $C(O)NH_2$, halo, $(C_1-C_3)$alkoxy, amino, hydroxy$(C_1-C_3)$alkyl, or $(C_1-C_3)$alkyl optionally substituted with aminocarbonyl or $(C_1-C_3)$alkylcarbonylamino,
a five-membered aromatic heterocycle optionally substituted with 1 or 2 substituents each independently selected from $(C_1-C_3)$alkyl, $C(O)H$, $C(O)(C_1-C_3)$alkyl, and halo, and
phenyl optionally substituted with 1 or 2 substituents each selected independently from OH, $-OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $C(O)R^{10}$, $C(O)NH(C_1-C_3)$alkoxy-$(C_1-C_3)$alkyl, $C(O)NH(C_3-C_6)$cycloalkyl, pyrrolidinonyl, imidazolinyl, imidazolidinonyl, $(C_1-C_3)$alkoxy optionally substituted with 1 or 2 OH groups, and $(C_1-C_3)$alkyl optionally mono-substituted with CN, OH, $NR^5R^5$, $NHC(O)R^6$,
$NHS(O)_2(C_1-C_3)$alkyl, $C(O)NR^5R^5$, oxazolidinonyl,
imidazolidinonyl optionally mono-substituted with $(C_1-C_3)$alkyl,
pyrrolidinonyl optionally mono-substituted with $(C_1-C_3)$alkyl,
a five-membered N containing heterocycle optionally mono-substituted with $(C_1-C_3)$alkyl,
piperazinyl optionally mono-substituted with $(C_1-C_3)$alkyl,
pyridyl optionally mono-substituted with $CF_3$, or $(C_1-C_3)$alkoxy,
thienyl optionally mono-substituted with $C(O)(C_1-C_3)$alkyl, or
pyrimidinyl optionally mono-substituted with $N[(C_1-C_3)$alkyl$]_2$;

$Ar^2$ is selected from benzodioxolyl,
phenyl optionally substituted with 1 or 2 substituents each selected independently from $(C_1-C_3)$alkyl, $(C_1-C_3)$alkoxy, OH, $NO_2$, CN, halo, and $CF_3$, and
pyridyl mono-substituted with $(C_1-C_3)$alkyl, or $CF_3$;

$R^1$ is selected from H, $(C_1-C_3)$alkyl, OH, and halo;
$R^2$ is selected from H, $(C_1-C_3)$alkyl, $(C_1-C_3)$alkoxy, OH, halo, $CF_3$, and $-OCF_3$;
$R^3$ is selected from H, $(C_1-C_3)$alkoxy, OH, halo, and $CF_3$;
$R^4$ is selected from hydrogen, $(C_1-C_3)$alkyl, $(C_1-C_3)$alkoxy, CN, and $C(O)NHR^5$, wherein $(C_1-C_3)$alkyl can optionally be substituted with halo, $(C_1-C_3)$alkoxy, hydroxyalkylamino, alkoxyalkylamino;
$R^5$ is selected from H, $(C_3-C_6)$cycloalkyl, and
$(C_1-C_3)$alkyl optionally substituted with 1 or 2 OH groups or mono-substituted with $(C_1-C_3)$alkoxy, $(C_1-C_3)$alkylamino, $S(O)_2(C_1-C_3)$alkyl, or $C(O)R^7$;
$R^6$ is selected from H, $(C_3-C_6)$cycloalkyl, $(C_1-C_3)$alkoxy, $(C_2-C_8)$alkenyl, $CHF_2$, $CF_3$, $NHR^5$,
and $(C_1-C_3)$alkyl optionally substituted with one or more substituents selected from Cl and F, or optionally mono-substituted with $NH_2$ or $NHC(O)(C_1-C_3)$alkyl;
$R^7$ is selected from $(C_1-C_3)$alkoxy, $(C_2-C_6)$alkenyl, $CHF_2$, $CF_3$, $(C_3-C_6)$cycloalkyl, $NR^{7-1}R^{7-1}$,
and $(C_1-C_3)$alkyl optionally substituted with one or more substituents selected from Cl and F, or mono-substituted with $NHC(O)(C_1-C_3)$alkyl or $NH_2$, wherein $R^{7-1}$ is hydrogen or $(C_1-C_3)$alkyl;
$R^8$ is selected from $(C_1-C_3)$alkyl and $NR^9R^9$;
$R^9$ is selected from H, and $(C_1-C_3)$alkyl optionally mono-substituted with
$(C_1-C_3)$alkoxy, or aminocarbonyl, or substituted with 1 or 2 OH groups;
$R^{10}$ is selected from H, $(C_1-C_3)$alkoxy, $NHR^9$, and
$(C_1-C_3)$alkyl optionally mono-substituted with pyrrolidinyl, morpholinyl, pyridinyl, piperazinyl optionally sub stituted with $(C_1-C_3)$alkyl, or piperidinyl optionally substituted with $(C_1-C_3)$alkyl;

n is 0, 1 or 2;

or a pharmaceutically acceptable salt thereof.

In another embodiment, the present Invention relates to a compound of formula (I), wherein $Ar^1$ is phenyl optionally substituted with 1 or 2 substituents each selected independently from OH, —$OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $C(O)R^{10}$, $C(O)NH(C_1-C_3)$alkoxy-$(C_1-C_3)$alkyl, $C(O)NH(C_3-C_6)$cycloalkyl, pyrrolidinonyl, imidazolinyl, imidazolidinonyl, $(C_1-C_3)$alkoxy optionally substituted with 1 or 2 OH groups, and $(C_1-C_3)$alkyl optionally mono-substituted with CN, OH, $NR^5R^5$, $NHC(O)R^6$, $NHS(O)_2(C_1-C_3)$alkyl, $C(O)NR^5R^5$, oxazolidinonyl, imidazolidinonyl optionally mono-substituted with $(C_1-C_3)$alkyl, pyrrolidinonyl optionally mono-substituted with $(C_1-C_3)$alkyl, a five-membered N containing heterocycle optionally mono-substituted with $(C_1-C_3)$alkyl, piperazinyl optionally mono-substituted with $(C_1-C_3)$alkyl, pyridyl optionally mono-substituted with $CF_3$, or $(C_1-C_3)$alkoxy, thienyl optionally mono-substituted with $C(O)(C_1-C_3)$alkyl, or pyrimidinyl optionally mono-substituted with $N[(C_1-C_3)$alkyl$]_2$, $R^5$ is selected from H, $(C_3-C_6)$cycloalkyl, and $(C_1-C_3)$alkyl optionally substituted with 1 or 2 OH groups or mono-substituted with $(C_1-C_3)$alkoxy, $(C_1-C_3)$alkylamino, $S(O)_2(C_1-C_3)$alkyl, or $C(O)R^7$;

$R^6$ is selected from H, $(C_3-C_5)$cycloalkyl, $(C_1-C_3)$alkoxy, $(C_2-C_8)$alkenyl, $CHF_2$, $CF_3$, $NHR^5$, and $(C_1-C_3)$alkyl optionally substituted with one or more substituents selected from Cl and F, or optionally mono-substituted with $NH_2$ or $NHC(O)(C_1-C_3)$alkyl;

$R^7$ is selected from $(C_1-C_3)$alkoxy, $(C_2-C_6)$alkenyl, $CHF_2$, $CF_3$, $(C_3-C_6)$cycloalkyl, $NR^{7-1}R^{7-1}$, and $(C_1-C_3)$alkyl optionally substituted with one or more substituents selected from Cl and F, or mono-substituted with $NHC(O)(C_1-C_3)$alkyl or $NH_2$, wherein $R^7$ is hydrogen, methyl or ethyl;

$R^8$ is selected from $(C_1-C_3)$alkyl and $NR^9R^9$;

$R^9$ is selected from H, and $(C_1-C_3)$alkyl optionally mono-substituted with $(C_1-C_3)$alkoxy, or aminocarbonyl, or substituted with 1 or 2 OH groups;

$R^{10}$ is selected from H, $(C_1-C_3)$alkoxy, $NHR^9$, and $(C_1-C_3)$alkyl optionally mono-substituted with pyrrolidinyl, morpholinyl, pyridinyl, piperazinyl optionally substituted with $(C_1-C_3)$alkyl, or piperidinyl optionally substituted with $(C_1-C_3)$alkyl;

In another embodiment, the present invention relates to a compound of formula (I), wherein $Ar^2$ is 2,4-dihalosubstituted phenyl.

In another embodiment, the present invention relates to a compound of formula (I), wherein $Ar^2$ is 2,4-dichlorophenyl.

In another embodiment, the present invention relates to a compound of formula (I), wherein $R^1$, $R^2$ and $R^3$ are hydrogen.

The terms identified above have the following meaning throughout:

The term "optionally substituted" means that the moiety so modified may have from none to up to at least the highest number of substituents indicated. Each substituent may replace any H atom on the moiety so modified as long as the replacement is chemically possible and chemically stable. When there are two or more substituents on any moiety, each substituent is chosen independently of any other substituent and can, accordingly, be the same or different.

The term "$(C_1-C_3)$alkyl" means a linear or branched saturated hydrocarbon radical having from about 1 to about 3 C atoms. Such groups include but are not limited to methyl, ethyl, n-propyl, isopropyl, and the like.

The term "$(C_1-C_3)$alkyl" optionally substituted with one or more substituents selected from Cl or F" means an alkyl group, as described above, that may be substituted (also as defined above) with from 1 up to perhalo (that is, up to 2 or 3 per C atom, as appropriate) Cl and/or F atom(s), each Cl and F atom being selected in each instance independently from any other Cl or F atom. Such groups include but are not limited to difluoromethyl, trichloromethyl, pentafluoroethyl, chlorodifluoromethyl, 1-chloro-1,1-difluoroethyl, dichlorofluoromethyl, 1-chloro-1,2,2-trifluoroethyl, 1-chloro-1,2,2-trifluoropropyl, and the like.

The term "$(C_3-C_6)$cycloalkyl" includes cyclopropyl, cyclobutyl, cyclopentyl, and cyclohexyl.

The term "$(C_1-C_3)$alkoxy" means a linear or branched saturated hydrocarbon radical having from about 1 to about 3 C atoms, said radical being attached to an O atom. The O atom is the atom through which the alkoxy substituent is attached to the rest of the molecule. Such groups include but are not limited to methoxy, ethoxy, n-propoxy, isopropoxy, and the like.

The term "$(C_2-C_6)$alkenyl" means a linear or branched carbon group having from about 2 to about 6 C atoms wherein at least two adjacent C atoms In the alkenyl group are joined by a double bond, with the proviso that when a C atom is double bonded to one adjacent C atom, it must be single bonded to any other adjacent C atom. The alkenyl group is attached to the rest of the molecule through a single bond.

The term "halo" means Cl, Br, F or I.

The term "pyridyl N-oxide" means that the N atom of the pyridyl ring containing an otherwise unsubstituted $sp^2$ N atom bears a covalently bound O atom, i.e., —N(->O).

When "(O)" is used in a chemical formula, it means an O atom that is double bonded to the atom to which it is attached, but is not further bonded to any other atom. For example, "C(O)" represents a carbonyl group.

The formulae "$N[C_1-C_3)$alkyl$]_2$", "$NR^5R^5$", "$NR^9R^9$", and the like, each means that each of the 2 possible groups attached to the N atom are selected independently from the other so that they may be the same or they may be different.

The term "a five-membered aromatic heterocycle" means an aromatic ring made of 5 atoms and containing at least 1 and no more than 2 heteroatoms, each selected independently from N, S and O. There can be only one S or one O atom in any one ring. Five-membered aromatic heterocycles include thienyl, imidazolyl, thiazolyl, oxazolyl, pyrazolyl, pyrrolyl, furyl, Isoxazolyl, isothiazolyl, and the like. The heterocycle is attached to the rest of the molecule through a bond attached to the heterocycle at any position of the heterocyclic radical from which a H atom could conceptually have been removed to create the radical from its corresponding stand-alone molecule.

The term "a five membered N containing heterocycle" means a ring made of 5 atoms, any 1 or 2 of which are N with the remaining atoms being C. The heterocycle is saturated, unsaturated or partially saturated. Five membered N containing heterocycles Include but are not limited to pyrrolyl, imidazolyl, pyrazolyl, pyrrolidinyl, pyrrolinyl, imidazolidinyl, imidazolinyl, pyrazolidinyl, pyrazolinyl, and the like. The heterocycle is attached to the rest of the molecule through a bond attached to the heterocycle at any position of the heterocyclic radical from which a H atom could conceptually have been removed to create the radical from its corresponding stand-alone molecule.

A dashed line (—) means to indicate the bond via which a radical is connected to the rest of the molecule.

The term "hydroxyalkylamino" means an amino group which bears an alkyl, wherein the alkyl is substituted with one hydroxy.

The term "alkoxyalkylamino" means an amino group which bears an alkyl, wherein the alkyl is substituted with one alkoxy.

The term "hydroxyalkyl" means an alkyl substituted with one hydroxy.

The term "$(C_1-C_3)$alkylcarbonylamino" means an amino group which bears an carbonyl group, wherein the carbonyl group is connected to an $(C_1-C_3)$alkyl.

The term "aminocarbonyl" means a carbonyl group which bears an amino group i.e. a $C(O)NH_2$ group. The point of attachment to the rest of the molecule is through the carbon atom of the carbonyl group.

When a phenyl ring, pyridyl ring, a five membered aromatic heterocycle, a five membered N containing heterocycle or any other ring radical is attached to the rest of the molecule, the bond to the rest of the molecule is attached to the radical at any position of the radical from which a H could conceptually have been removed to create the radical from its corresponding stand-alone molecule.

In another embodiment, the present invention relates to the treatment and/or prophylaxis of disorders; a pharmaceutical composition comprising a compound according to claim 1; a pharmaceutical composition comprising a compound according to claim 1 in combination with at least one pharmaceutically acceptable excipient; a process for preparing said pharmaceutical composition, comprising combining at least one compound of claim 1 with at least one pharmaceutically acceptable excipient, mixing the combination and bringing the combination into a suitable administration form; said pharmaceutical composition for the treatment or prophylaxis of hyperproliferative disorders; the use of a compound according to claim 1 for manufacturing a medicament for the treatment or prophylaxis of hyperproliferative disorders; a method of treating a disease or condition in a mammal, comprising administering to a mammal in need thereof an effective amount of a compound according to the formula (I); and said method, wherein the disease or condition is a hyperproliferative disorder.

In yet another embodiment, the present invention relates to a compound of Formula (I-1)

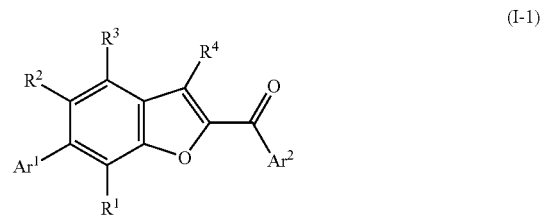

(I-1)

wherein
$Ar^1$ is selected from benzodioxolyl, pyrrolidinyl,
  pyridyl or pyridyl N-oxide, each optionally mono-substituted with $C(O)NH_2$, halo, $(C_1-C_3)$alkoxy, or $NH(C_1-C_3)$alkyl,
  a five-membered aromatic heterocycle optionally substituted with 1 or 2 substituents each independently selected from $(C_1-C_3)$alkyl, $C(O)H$, $C(O)(C_1-C_3)$alkyl, and halo, and
  phenyl optionally substituted with 1 or 2 substituents each selected independently from OH, $-OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $C(O)R^{10}$, $C(O)NH(C_3-C_6)$cycloalkyl, pyrrolidinonyl, imidazolidinonyl, $(C_1-C_3)$alkoxy optionally substituted with 1 or 2 OH groups, and $(C_1-C_3)$alkyl optionally mono-substituted with CN, OH, $NR^5R^5$, $NHC(O)R^6$, $NHS(O)_2(C_1-C_3)$alkyl, $C(O)NR^5R^5$, oxazolidinonyl, imidazolidinonyl optionally mono-substituted with $(C_1-C_3)$alkyl, pyrrolidinonyl optionally mono-substituted with $(C_1-C_3)$alkyl,
  a five-membered N containing heterocycle optionally mono-substituted with $(C_1-C_3)$alkyl,
  piperazinyl optionally mono-substituted with $(C_1-C_3)$alkyl,
  pyridyl optionally mono-substituted with $CF_3$, or $(C_1-C_3)$alkoxy,
  thienyl optionally mono-substituted with $C(O)(C_1-C_3)$alkyl, or
  pyrimidinyl optionally mono-substituted with $N[(C_1-C_3)$alkyl$]_2$;
$Ar^2$ is selected from benzodioxolyl,
  phenyl optionally substituted with 1 or 2 substituents each selected independently from $(C_1-C_3)$alkyl, $(C_1-C_3)$alkoxy, OH, $NO_2$, CN, halo, and $CF_3$, and
  pyridyl mono-substituted with $(C_1-C_3)$alkyl, or $CF_3$;
$R^1$ is selected from H, $(C_1-C_3)$alkyl, OH, and halo;
$R^2$ is selected from H, $(C_1-C_3)$alkyl, $(C_1-C_3)$alkoxy, OH, halo, $CF_3$, and $-OCF_3$;
$R^3$ is selected from H, $(C_1-C_3)$alkoxy, OH, halo, and $CF_3$;
$R^4$ is selected from $(C_1-C_3)$alkyl, CN, and $C(O)NHR^5$;
$R^5$ is selected from H, $(C_3-C_6)$cycloalkyl, and ($C_1$-$C_3$)alkyl optionally substituted with 1 or 2 OH groups or mono-substituted with ($C_1$-$C_3$)alkoxy, $S(O)_2$($C_1$-$C_3$) alkyl, or $C(O)R^7$;

$R^6$ is selected from H, ($C_3$-$C_6$)cycloalkyl, ($C_1$-$C_3$)alkoxy, ($C_2$-$C_6$)alkenyl, $CHF_2$, $CF_3$, $NHR^5$, and ($C_1$-$C_3$)alkyl optionally substituted with one or more substituents selected from Cl and F, or optionally mono-substituted with $NH_2$ or $NHC(O)$($C_1$-$C_3$)alkyl;

$R^7$ is selected from ($C_1$-$C_3$)alkoxy, ($C_2$-$C_6$)alkenyl, $CHF_2$, $CF_3$, ($C_3$-$C_6$)cycloalkyl, $NR^5R^5$, and ($C_1$-$C_3$)alkyl optionally substituted with one or more substituents selected from Cl and F, or mono-substituted with $NHC(O)$($C_1$-$C_3$)alkyl or $NH_2$;

$R^8$ is selected from ($C_1$-$C_3$)alkyl and $NR^9R^9$;

$R^9$ is selected from H, and ($C_1$-$C_3$)alkyl optionally mono-substituted with ($C_1$-$C_3$)alkoxy, or substituted with 1 or 2 OH groups;

$R^{10}$ is selected from H, ($C_1$-$C_3$)alkoxy, $NHR^9$, and ($C_1$-$C_3$)alkyl optionally mono-substituted with pyrrolidinyl, morpholinyl, pyridinyl, piperazinyl optionally substituted with ($C_1$-$C_3$)alkyl, or piperidinyl optionally substituted with ($C_1$-$C_3$)alkyl;

n is 0, 1 or 2;

or a pharmaceutically acceptable salt thereof.

In yet another embodiment, the present invention relates to a method of treating a hyper-proliferative disorder comprising the administration to a patient in need thereof of an effective amount of a compound of Formula (I-1)

(I-1)

wherein $Ar^1$ is selected from benzodioxolyl, pyrrolidinyl, pyridyl or pyridyl N-oxide, each optionally mono-substituted with $C(O)NH_2$, halo, ($C_1$-$C_3$)alkoxy, or $NH$($C_1$-$C_3$)alkyl, a five-membered aromatic heterocycle optionally substituted with 1 or 2 substituents each independently selected from ($C_1$-$C_3$)alkyl, $C(O)H$, $C(O)$($C_1$-$C_3$)alkyl, and halo, and phenyl optionally substituted with 1 or 2 substituents each selected independently from OH, —$OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $C(O)R^{10}$, $C(O)NH$($C_3$-$C_6$)cycloalkyl, pyrrolidinonyl, imidazolidinonyl, ($C_1$-$C_3$)alkoxy optionally substituted with 1 or 2 OH groups, and ($C_1$-$C_3$)alkyl optionally mono-substituted with CN, OH, $NR^5R^5$, $NHC(O)R^6$, $NHS(O)_2$($C_1$-$C_3$)alkyl, $C(O)NR^5R^5$, oxazolidinonyl, imidazolidinonyl optionally mono-substituted with ($C_1$-$C_3$)alkyl, pyrrolidinonyl optionally mono-substituted with ($C_1$-$C_3$)alkyl, a five-membered N containing heterocycle optionally mono-substituted with ($C_1$-$C_3$)alkyl, piperazinyl optionally mono-substituted with ($C_1$-$C_3$) alkyl, pyridyl optionally mono-substituted with $CF_3$, or ($C_1$-$C_3$)alkoxy, thienyl optionally mono-substituted with $C(O)$($C_1$-$C_3$) alkyl, or pyrimidinyl optionally mono-substituted with $N[(C_1$-$C_3$)alkyl]$_2$;

$Ar^2$ is selected from benzodioxolyl, phenyl optionally substituted with 1 or 2 substituents each selected independently from ($C_1$-$C_3$)alkyl, ($C_1$-$C_3$) alkoxy, OH, $NO_2$, CN, halo, and $CF_3$, and pyridyl mono-substituted with ($C_1$-$C_3$)alkyl, or $CF_3$;

$R^1$ is selected from H, ($C_1$-$C_3$)alkyl, OH, and halo;

$R^2$ is selected from H, ($C_1$-$C_3$)alkyl, ($C_1$-$C_3$)alkoxy, OH, halo, $CF_3$, and —$OCF_3$;

$R^3$ is selected from H, ($C_1$-$C_3$)alkoxy, OH, halo, and $CF_3$;

$R^4$ is selected from ($C_1$-$C_3$)alkyl, CN, and $C(O)NHR^5$;

$R^5$ is selected from H, ($C_3$-$C_6$)cycloalkyl, and ($C_1$-$C_3$)alkyl optionally substituted with 1 or 2 OH groups or mono-substituted with ($C_1$-$C_3$)alkoxy, $S(O)_2$($C_1$-$C_3$) alkyl, or C(O)RF;

$R^6$ is selected from H, ($C_3$-$C_6$)cycloalkyl, ($C_1$-$C_3$)alkoxy, ($C_2$-$C_6$)alkenyl, $CHF_2$, $CF_3$, $NHR^5$, and ($C_1$-$C_3$)alkyl optionally substituted with one or more substituents selected from Cl and F, or optionally mono-substituted with $NH_2$ or $NHC(O)$($C_1$-$C_3$)alkyl;

$R^7$ is selected from ($C_1$-$C_3$)alkoxy, ($C_2$-$C_6$)alkenyl, $CHF_2$, $CF_3$, ($C_3$-$C_6$)cycloalkyl, $NR^5R^5$, and ($C_1$-$C_3$)alkyl optionally substituted with one or more substituents selected from Cl and F, or monosubstituted with $NHC(O)$($C_1$-$C_3$)alkyl or $NH_2$;

$R^8$ is selected from ($C_1$-$C_3$)alkyl and $NR^9R^9$;

$R^9$ is selected from H, and ($C_1$-$C_3$)alkyl optionally mono-substituted with ($C_1$-$C_3$)alkoxy, or substituted with 1 or 2 OH groups;

$R^{10}$ is selected from H, ($C_1$-$C_3$)alkoxy, $NHR^9$, and ($C_1$-$C_3$)alkyl optionally mono-substituted with pyrrolidinyl, morpholinyl, pyridinyl, piperazinyl optionally substituted with ($C_1$-$C_3$)alkyl, or piperidinyl optionally substituted with ($C_1$-$C_3$)alkyl;

n is 0, 1 or 2;

or a pharmaceutically acceptable salt thereof.

Representative compounds of formula (I) are described In Table 1 below.

TABLE 1

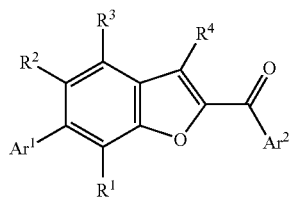

In table 1, the method of the last column refers to the method of Reaction Schemes 1-12 of page 47 et seq.
(I), $R^1$, $R^2$, $R^3$ = H

| Example No. | $R^4$ | $Ar^1$ | $Ar^2$ | HPLC/ES-MS [M + H]+ (RT min) | Method |
|---|---|---|---|---|---|
| 1 | $CH_3$ | 3-methylphenyl | 2,4-dichlorophenyl | 395/397 (4.85) | 1 |
| 2 | $C(O)NH_2$ | 3-methylphenyl | 2,4-dichlorophenyl | 424/426 (4.26) | 2 |
| 3 | CN | 3-methylphenyl | 2,4-dichlorophenyl | 406/408 (4.55) | 3 |
| 4 | $CH_3$ | pyridin-3-yl | 2,4-dichlorophenyl | 382/384 (2.93) | 1 |
| 5 | $CH_3$ | 3-cyanophenyl | 2,4-dichlorophenyl | 406/408 (4.13) | 1 |
| 6 | $CH_3$ | 3-(methylsulfonylamino)phenyl | 2,4-dichlorophenyl | 474/476 (3.78) | 1 |

TABLE 1-continued

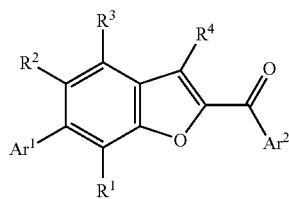

In table 1, the method of the last column refers to the method of Reaction
Schemes 1-12 of page 47 et seq.
(I), $R^1$, $R^2$, $R^3$ = H

| Example No. | $R^4$ | $Ar^1$ | $Ar^2$ | HPLC/ ES-MS [M + H]+ (RT min) | Method |
|---|---|---|---|---|---|
| 7 | CH$_3$ | (3-acetamidomethylphenyl) | (2,4-dichlorophenyl) | 452/454 (3.66) | 1 |
| 8 | CH$_3$ | (3-carbamoylmethylphenyl) | (2,4-dichlorophenyl) | 438/440 (3.60) | 1 |
| 9 | CH$_3$ | (3-methoxyphenyl) | (2,4-dichlorophenyl) | 411/413 (4.54) | 1 |
| 10 | CH$_3$ | (3-acetylphenyl) | (2,4-dichlorophenyl) | 423/425 (3.01) | 1 |
| 11 | CH$_3$ | (3-aminomethylphenyl) | (2,4-dichlorophenyl) | 434/436 (2.75) | 1 |

TABLE 1-continued
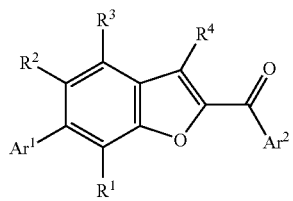
In table 1, the method of the last column refers to the method of Reaction Schemes 1-12 of page 47 et seq.
(I), $R^1$, $R^2$, $R^3$ = H
| Example No. | $R^4$ | $Ar^1$ | $Ar^2$ | HPLC/ES-MS [M + H]+ (RT min) | Method |
|---|---|---|---|---|---|
| 12 | $CH_3$ | 3-(NHC(O)CF$_3$)phenyl | 2,4-dichlorophenyl | 492/494 (3.99) | 1 |
| 13 | $CH_3$ | 3-(NHC(O)OCH$_3$)phenyl | 2,4-dichlorophenyl | 454/456 (3.72) | 1 |
| 14 | $CH_3$ | 3-(NHC(O)OCH$_2$CH$_3$)phenyl | 2,4-dichlorophenyl | 488/470 (3.83) | 1 |
| 15 | $CH_3$ | 3-(NHC(O)CH=CH$_2$)phenyl | 2,4-dichlorophenyl | 450/452 (3.61) | 1 |

TABLE 1-continued

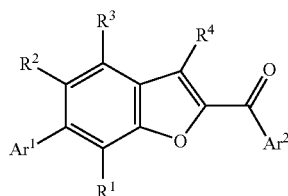

In table 1, the method of the last column refers to the method of Reaction
Schemes 1-12 of page 47 et seq.
(I), $R^1$, $R^2$, $R^3$ = H

| Example No. | $R^4$ | $Ar^1$ | $Ar^2$ | HPLC/ES-MS [M + H]+ (RT min) | Method |
|---|---|---|---|---|---|
| 16 | CH₃ | 3-(NHC(O)CHF₂)-phenyl | 2,4-dichlorophenyl | 474/476 (3.63) | 1 |
| 17 | CH₃ | 3-(CH₂NHC(O)OCH₃)-phenyl | 2,4-dichlorophenyl | 468/470 (3.54) | 1 |
| 18 | CH₃ | 3-(CH₂NHC(O)OEt)-phenyl | 2,4-dichlorophenyl | 482/484 (3.71) | 1 |
| 19 | CH₃ | 3-(CH₂NHC(O)CH=CH₂)-phenyl | 2,4-dichlorophenyl | 464/466 (3.34) | 1 |
| 20 | CH₃ | 3-chlorophenyl | 2,4-dichlorophenyl | 415/417 (3.51) | 1 |

TABLE 1-continued

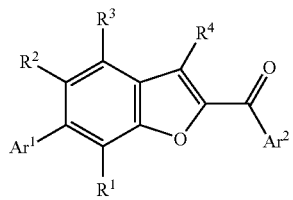

In table 1, the method of the last column refers to the method of Reaction
Schemes 1-12 of page 47 et seq.
(I), $R^1, R^2, R^3$ = H

| Example No. | $R^4$ | $Ar^1$ | $Ar^2$ | HPLC/ES-MS [M + H]+ (RT min) | Method |
|---|---|---|---|---|---|
| 21 | CH$_3$ | 3-(trifluoromethyl)phenyl | 2,4-dichlorophenyl | 449/451 (3.55) | 1 |
| 22 | CH$_3$ | 2-chlorophenyl | 2,4-dichlorophenyl | 415/417 (3.41) | 1 |
| 23 | CH$_3$ | 3,4-dimethoxyphenyl | 2,4-dichlorophenyl | 399/401 (3.34) | 1 |
| 24 | CH$_3$ | 3-nitrophenyl | 2,4-dichlorophenyl | 428/428 (3.39) | 1 |
| 25 | CH$_3$ | 3,4-dimethylphenyl | 2,4-dichlorophenyl | 409/411 (3.68) | 1 |
| 26 | CH$_3$ | 2-fluorophenyl | 2,4-dichlorophenyl | 399/401 (3.34) | 1 |

TABLE 1-continued
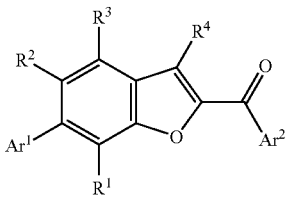
In table 1, the method of the last column refers to the method of Reaction Schemes 1-12 of page 47 et seq.
(I), $R^1$, $R^2$, $R^3$ = H
| Example No. | $R^4$ | $Ar^1$ | $Ar^2$ | HPLC/ ES-MS [M + H]+ (RT min) | Method |
|---|---|---|---|---|---|
| 27 | CH$_3$ | 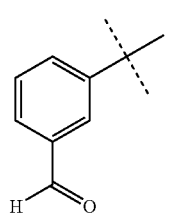 | 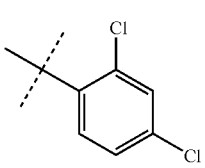 | 409/411 (3.17) | 1 |
| 28 | CH$_3$ | 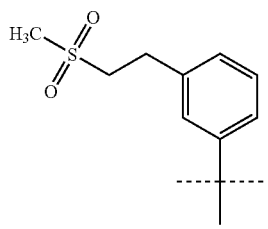 | 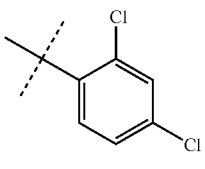 | 488/490 (3.75) | 1 |
| 29 | CH$_3$CH$_2$ | 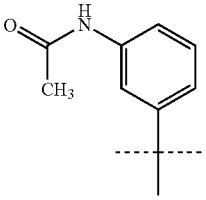 | 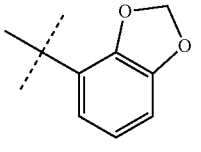 | 428.2 (3.36) | 1 |
| 30 | CH$_3$CH$_2$ | 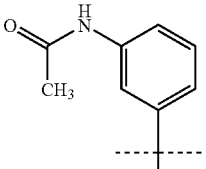 | 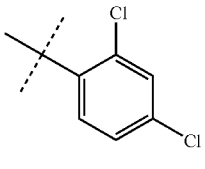 | 452.1 (3.74) | 1 |
| 31 | CH$_3$CH$_2$ | 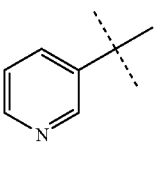 | 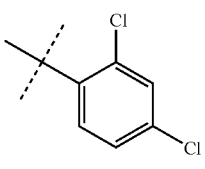 | 396.2 (3.47) | 1 |

TABLE 1-continued
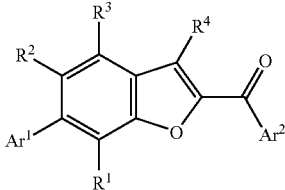
In table 1, the method of the last column refers to the method of Reaction Schemes 1-12 of page 47 et seq.
(I), $R^1, R^2, R^3 = H$
| Example No. | $R^4$ | $Ar^1$ | $Ar^2$ | HPLC/ES-MS [M + H]+ (RT min) | Method |
|---|---|---|---|---|---|
| 32 | $CH_3CH_2$ | 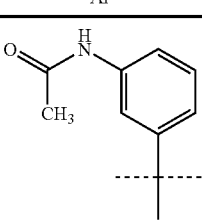 | 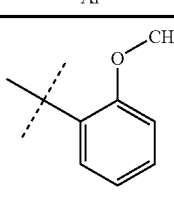 | 414.1 (3.81) | 1 |
| 33 | $CH_3CH_2$ | 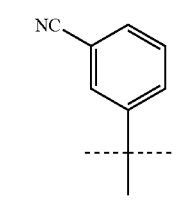 | 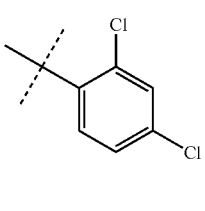 | 420.1 (4.65) | 1 |
| 34 | $CH_3CH_2$ | 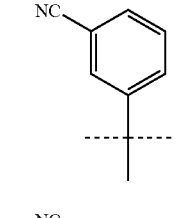 | 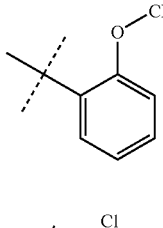 | 382.1 (3.78) | 1 |
| 35 | $(CH_3)_2CH$ | 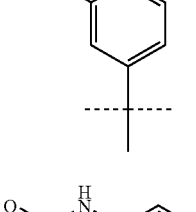 | 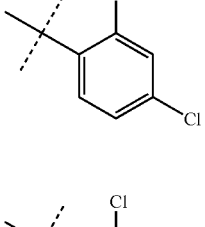 | 434/436 (2.95) | 1 |
| 36 | $(CH_3)_2CH$ | 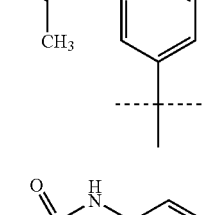 | 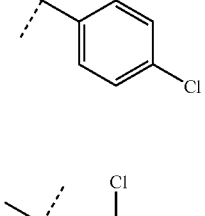 | 466/468 (2.69) | 1 |
| 37 | $(CH_3)_2CH$ | 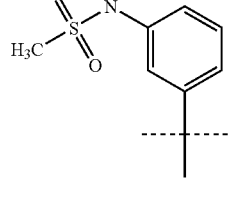 | 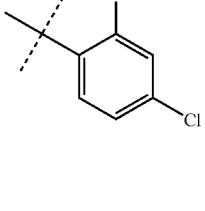 | 502/504 (3.17) | 1 |

TABLE 1-continued

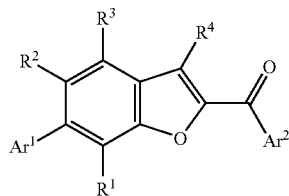

In table 1, the method of the last column refers to the method of Reaction Schemes 1-12 of page 47 et seq.
(I), $R^1$, $R^2$, $R^3$ = H

| Example No. | $R^4$ | $Ar^1$ | $Ar^2$ | HPLC/ES-MS [M + H]+ (RT min) | Method |
|---|---|---|---|---|---|
| 38 | $(CH_3)_2CH$ | 3-(CH₃C(O)NHCH₂)-phenyl | 2,4-dichlorophenyl | 480/482 (2.81) | 1 |
| 39 | $(CH_3)_2CH$ | 3-(H₂NC(O)CH₂)-phenyl | 2,4-dichlorophenyl | 466/468 (2.81) | 1 |
| 40 | $C(O)NH_2$ | pyridin-3-yl | 2,4-dichlorophenyl | 411/413 (3.23) | 2 |
| 41 | $C(O)NH_2$ | 3-NC-phenyl | 2,4-dichlorophenyl | 435/437 (3.70) | 2 |
| 42 | $C(O)NHCH_3$ | 3-NC-phenyl | 2,4-dichlorophenyl | 449/451 (3.54) | 2 |
| 43 | $C(O)NH_2$ | 3-CH₃O-phenyl | 2,4-dichlorophenyl | 440/442 (3.85) | 2 |

TABLE 1-continued

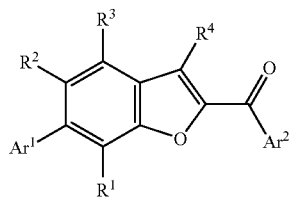

In table 1, the method of the last column refers to the method of Reaction Schemes 1-12 of page 47 et seq.
(I), $R^1$, $R^2$, $R^3$ = H

| Example No. | $R^4$ | $Ar^1$ | $Ar^2$ | HPLC/ ES-MS [M + H]+ (RT min) | Method |
|---|---|---|---|---|---|
| 44 | CN | 3-methoxyphenyl | 2,4-dichlorophenyl | 422/424 (4.37) | 3 |
| 45 | CN | 3-cyanophenyl | 2,4-dichlorophenyl | NMR1* | 3 |
| 46 | CN | 3-nitrophenyl | 2,4-dichlorophenyl | NMR2** | 3 |
| 170 | CH2-NH-CH2CH2-OMe | 3-(methylsulfonylaminomethyl)phenyl | 2,4-dichlorophenyl | 562 (2.66) | 10 |
| 171 | CH2-NH-CH2CH2-OMe | 3-(methylsulfonylamino)phenyl | 2,4-dichlorophenyl | 547 (2.73) | 10 |

TABLE 1-continued
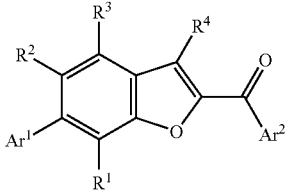
In table 1, the method of the last column refers to the method of Reaction Schemes 1-12 of page 47 et seq.
(I), $R^1, R^2, R^3$ = H
| Example No. | $R^4$ | $Ar^1$ | $Ar^2$ | HPLC/ ES-MS [M + H]+ (RT min) | Method |
|---|---|---|---|---|---|
| 172 | | | | 562 (2.63) | 10 |
| 173 | | | | 561 (2.59) | 10 |
| 174 | | | | 547 (2.59) | 10 |
| 175 | | | | 589 (2.86) | 10 |
| 176 | $CF_3$ | | | 492/494 (4.33) | 10 |

TABLE 1-continued

In table 1, the method of the last column refers to the method of Reaction Schemes 1-12 of page 47 et seq.
(I), $R^1$, $R^2$, $R^3$ = H

| Example No. | $R^4$ | $Ar^1$ | $Ar^2$ | HPLC/ ES-MS [M + H]+ (RT min) | Method |
|---|---|---|---|---|---|
| 177 | —CH$_2$OCH$_3$ | 3-(CH$_3$SO$_2$NH)-phenyl | 2,4-dichlorophenyl | 504/506 (3.81) | 10 |
| 178 | —CH$_2$OCH$_3$ | 3-(CH$_3$C(O)NHCH$_2$)-phenyl | 2,4-dichlorophenyl | 482/484 (3.85) | 10 |
| 179 | —CH$_2$OCH$_3$ | 3-(CH$_3$C(O)NH)-phenyl | 2,4-dichlorophenyl | 468/470 (3.72) | 10 |
| 180 | CF$_3$ | 3-(CH$_3$SO$_2$NH)-phenyl | 2,4-dichlorophenyl | 428/430 (4.38) | 8 |
| 181 | CF$_3$ | 3-aminophenyl | 2,4-dichlorophenyl | 450/452 (3.97) | 8 |

TABLE 1-continued
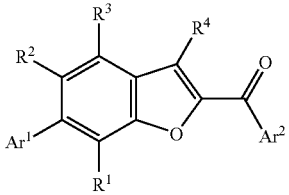
In table 1, the method of the last column refers to the method of Reaction Schemes 1-12 of page 47 et seq.
(I), $R^1$, $R^2$, $R^3$ = H
| Example No. | $R^4$ | $Ar^1$ | $Ar^2$ | HPLC/ES-MS [M + H]+ (RT min) | Method |
|---|---|---|---|---|---|
| 182 | CH$_3$ | 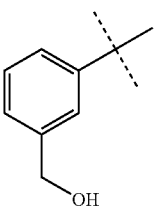 | 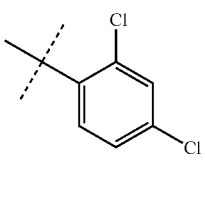 | 411/413 (3.91) | 1 |
| 183 | H | 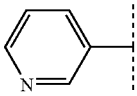 | 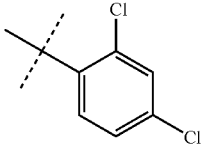 | 368/370 (2.74) | 11 |
| 184 | H | 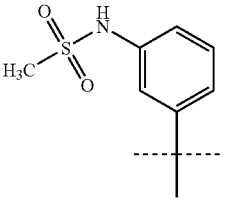 | 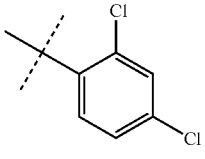 | 460/462 (3.64) | 11 |
| 185 | H | 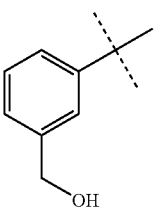 | 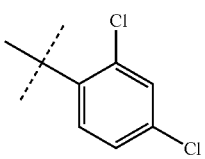 | 397/399 (3.57) | 11 |
| 186 | CH$_3$ | 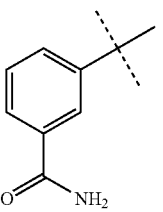 | 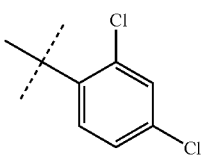 | 424/426 (3.59) | 12 |

TABLE 1-continued
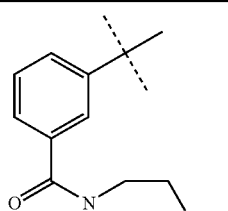
In table 1, the method of the last column refers to the method of Reaction Schemes 1-12 of page 47 et seq.
(I), $R^1$, $R^2$, $R^3$ = H
| Example No. | $R^4$ | $Ar^1$ | $Ar^2$ | HPLC/ ES-MS [M + H]+ (RT min) | Method |
|---|---|---|---|---|---|
| 187 | CH$_3$ | 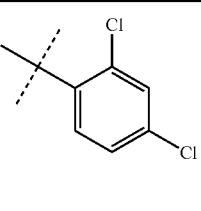 | 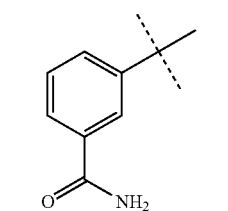 | 482/484 (3.78) | 1 |
| 188 | CH$_3$ | 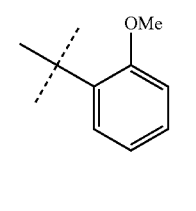 | 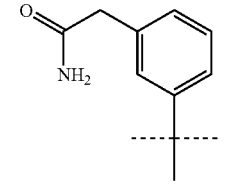 | 386 (2.87) | 12 |
| 189 | CH$_3$ | 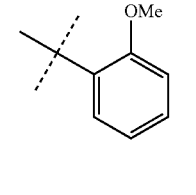 | 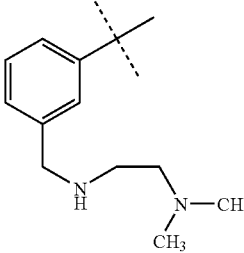 | 400 (2.86) | 12 |
| 190 | CH$_3$ | 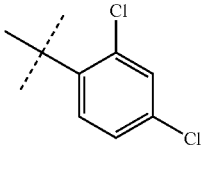 | 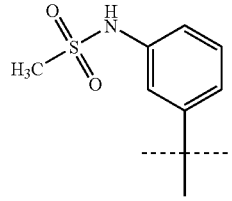 | 481/483 (2.84) | 1 |
| 191 | OCH$_3$ | 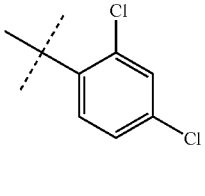 | | 492 (3.57) | 9 |

TABLE 1-continued
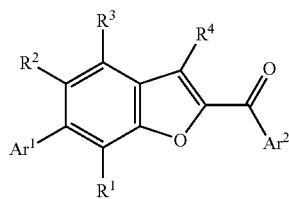
In table 1, the method of the last column refers to the method of Reaction
Schemes 1-12 of page 47 et seq.
(I), $R^1$, $R^2$, $R^3$ = H
| Example No. | $R^4$ | $Ar^1$ | $Ar^2$ | HPLC/ ES-MS [M + H]+ (RT min) | Method |
|---|---|---|---|---|---|
| 192 | OCH$_3$ | | | 456 (3.46) | 9 |
| 193 | OCH$_3$ | | | 429 (3.53) | 9 |
| 194 | OCH$_3$ | | | 506 (3.66) | 9 |
| 195 | CH$_3$ | | | 398 (3.74) | 9 |
| 196 | CH$_3$ | | | 411 (2.05) | 12 |

TABLE 1-continued

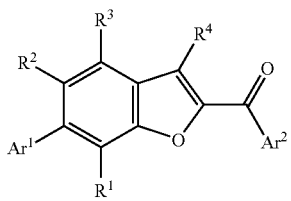

In table 1, the method of the last column refers to the method of Reaction Schemes 1-12 of page 47 et seq.

(I), $R^1$, $R^2$, $R^3$ = H

| Example No. | $R^4$ | $Ar^1$ | $Ar^2$ | HPLC/ES-MS [M + H]+ (RT min) | Method |
|---|---|---|---|---|---|
| 197 | CH₃ | 6-aminopyridin-2-yl | 2,4-dichlorophenyl | 397/399 (2.65) | 12 |
| 198 | CH₃ | 3-(2-hydroxyethyl)phenyl | 2,4-dichlorophenyl | 425/426 (3.96) | 1 |
| 199 | CH₃ | 3-(carbamoylmethylaminocarbonylmethyl)phenyl | 2,4-dichlorophenyl | 495/497 (3.30) | 1 |
| 200 | CH₃ | 3-(carbamoylmethylaminomethyl)phenyl | 2,4-dichlorophenyl | 467/469 (3.17) | 1 |
| 201 | CH₃ | 3-(carbamoylmethylaminocarbonylmethyl)phenyl | 2,4-dimethoxyphenyl | 487 (3.05) | 1 |

TABLE 1-continued

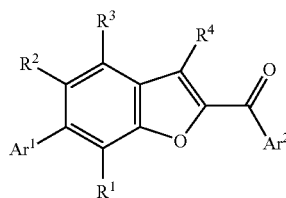

In table 1, the method of the last column refers to the method of Reaction
Schemes 1-12 of page 47 et seq.
(I), $R^1$, $R^2$, $R^3$ = H

| Example No. | $R^4$ | $Ar^1$ | $Ar^2$ | HPLC/ ES-MS [M + H]+ (RT min) | Method |
|---|---|---|---|---|---|
| 202 | CH$_3$ | 3-(hydroxymethyl)phenyl (t-Bu) | 2,4-diOMe-phenyl (t-Bu) | 403 (2.78) | 1 |
| 203 | CH$_3$ | 3-acetamidophenyl | 2,4-diOMe-phenyl (t-Bu) | 430 (3.36) | 1 |
| 204 | CH$_3$ | 3-(methylsulfonamido)phenyl | 2,4-diOMe-phenyl (t-Bu) | 466 (3.46) | 1 |
| 205 | CH$_3$ | 3-(carbamoylmethyl)phenyl | 2,4-diOMe-phenyl (t-Bu) | 430 (3.81) | 12 |
| 206 | CH$_3$ | 6-(hydroxymethyl)pyridin-2-yl | 2,4-diCl-phenyl | 412/414 (3.78) | 12 |

TABLE 1-continued
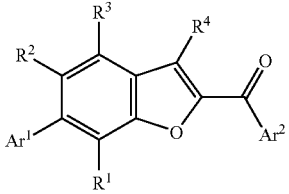
In table 1, the method of the last column refers to the method of Reaction Schemes 1-12 of page 47 et seq.
(I), $R^1, R^2, R^3 = H$
| Example No. | $R^4$ | $Ar^1$ | $Ar^2$ | HPLC/ES-MS [M + H]+ (RT min) | Method |
|---|---|---|---|---|---|
| 207 | CH$_3$ | 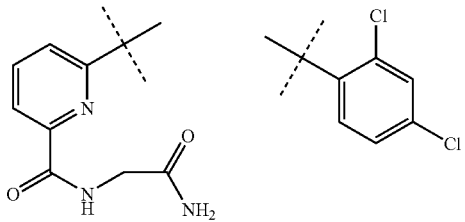 | 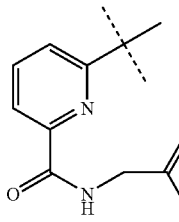 | 481/483 (3.33) | 1 |
| 208 | CH$_3$ | 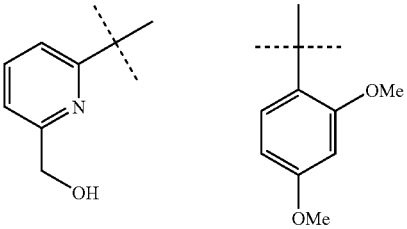 | 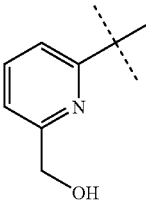 | 404 (2.72) | 1 |
| 209 | CH$_3$ | 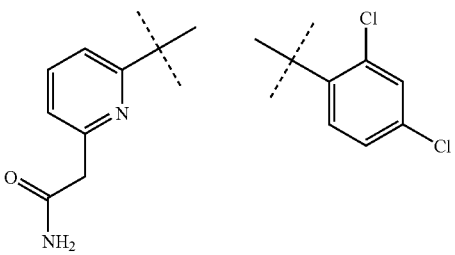 | 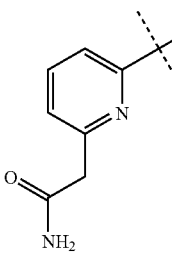 | 441/443 (3.27) | 12 |
| 210 | CH$_3$ | 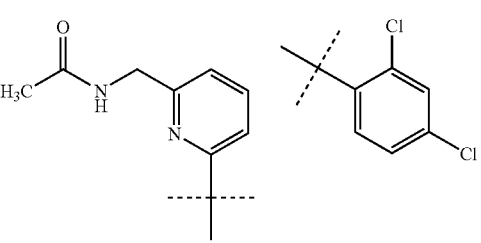 | 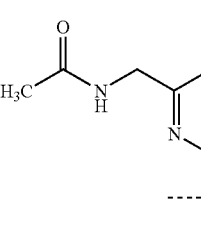 | 453/455 (3.36) | 12 |

TABLE 1-continued

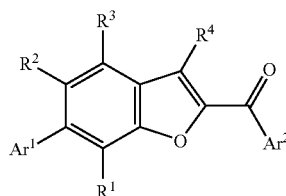

In table 1, the method of the last column refers to the method of Reaction Schemes 1-12 of page 47 et seq.
(I), $R^1$, $R^2$, $R^3$ = H

| Example No. | $R^4$ | $Ar^1$ | $Ar^2$ | HPLC/ES-MS [M + H]+ (RT min) | Method |
|---|---|---|---|---|---|
| 211 | $CH_3$ | 6-(aminocarbonyl)pyridin-2-yl | 2,4-dimethoxyphenyl | 417 (3.16) | 12 |
| 212 | $CH_3$ | 6-(acetamidomethyl)pyridin-2-yl | 2,4-dimethoxyphenyl | 445 (2.88) | 12 |
| 213 | $CH_3$ | 6-(aminocarbonylmethyl)pyridin-2-yl | 2,4-dimethoxyphenyl | 431 (2.74) | 12 |
| 214 | $CH_3$ | 6-(aminocarbonyl)pyridin-2-yl | 2,4-dichlorophenyl | 425 (3.64) | 12 |

*NMR1: $^1$H-NMR (CDCl$_3$): δ 7.95 (d, J = 8.3 Hz, 1H), 7.89 (s, 1H), 7.83 (d, J = 8.3 Hz, 1H), 7.79 (s, 1H), 7.70 (m, 2H), 7.60 (t, 1H), 7.55-7.52 (m, 2H), 7.49 (ds, J = 1.5, 8.3 Hz, 1H),
**NMR2: $^1$H-NMR (CDCl$_3$): δ 8.48 (s, 1H), 8.27 (d, J = 8.3 Hz, 1H), 7.97 (d, J = 8.3 Hz, 1H), 7.95 (d, J = 8.3 Hz, 1H), 7.86 (s, 1H), 7.77 (dd, J = 1.5, 8.3 Hz, 1H), 7.64 (t, 1H), 7.55 (s, 1H), 7.54 (d, J = 8.3 Hz, 1H), 7.45 (dd, J = 1.5, 8.3 Hz, 1H).

Further examples of the compounds of the present invention include the compound Examples of Table 2 that can be prepared using the methods described in Reaction Schemes 1-12 below or methods analogous thereto.

TABLE 2
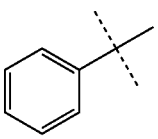
| Example No. | R¹ | R² | R³ | R⁴ | Ar¹ | Ar² |
|---|---|---|---|---|---|---|
| 47 | H | H | H | CH$_3$ | phenyl | phenyl |
| 48 | H | H | H | CH$_3$ | 3-(H$_3$C-C(O)-NH)-phenyl | 2,4-dichlorophenyl |
| 49 | H | H | H | CN | 3-(CH$_2$NHCOCH$_3$)-phenyl | 2-bromo-4-fluorophenyl |
| 50 | H | H | H | CH$_3$ | 3-(CF$_3$CF$_2$C(O)NH)-phenyl | 3-nitrophenyl |
| 51 | H | H | H | CH$_3$ | 3-(CH$_2$CONH$_2$)-phenyl | 3-cyanophenyl |
| 52 | H | H | H | CH$_3$CH$_2$ | 3-(SO$_2$Me)-phenyl | 2,4-bis(trifluoromethyl)phenyl |

TABLE 2-continued
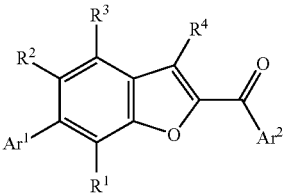
(I)
| Example No. | R¹ | R² | R³ | R⁴ | Ar¹ | Ar² |
|---|---|---|---|---|---|---|
| 53 | H | H | H | $CH_3$ | 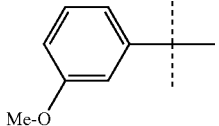 | 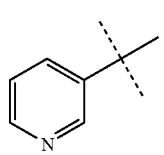 |
| 54 | H | H | H | $C(O)NH_2$ | 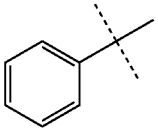 | 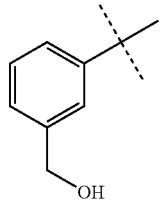 |
| 55 | H | H | H | $CH_3$ | 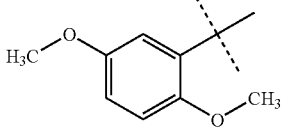 | 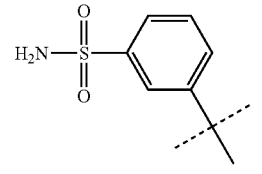 |
| 56 | H | H | H | $CH_3$ | 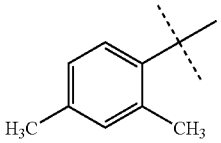 | 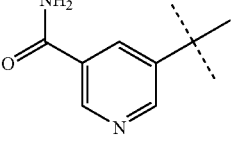 |
| 57 | H | H | H | $CH_3$ | 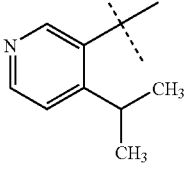 | 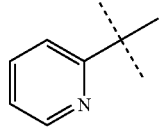 |
| 58 | H | OH | H | $(CH_3)_2CH$ | 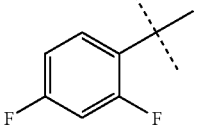 | 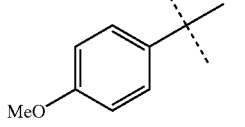 |
| 59 | H | H | H | $CH_3CH_2$ | 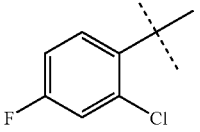 | |

TABLE 2-continued (I)

| Example No. | R¹ | R² | R³ | R⁴ | Ar¹ | Ar² |
|---|---|---|---|---|---|---|
| 60 | H | H | H | CH₃ | 3-OCF₃-phenyl | 2,4-difluorophenyl |
| 61 | H | H | H | CN | 3-CF₃-phenyl | 2-Cl-4-F-phenyl |
| 62 | H | H | H | CH₃ | 4-(N-methylcarbamoyl)phenyl | 4-isopropylpyridin-3-yl |
| 63 | H | H | H | CH₃ | 3-chlorophenyl | 2,4-dichlorophenyl |
| 64 | H | H | H | C(O)NH₂ | 3-methylphenyl | 2-Br-4-F-phenyl |
| 65 | H | H | H | (CH₃)₂CH | 3-OEt-phenyl | 3-NO₂-phenyl |

TABLE 2-continued (I)

| Example No. | R¹ | R² | R³ | R⁴ | Ar¹ | Ar² |
|---|---|---|---|---|---|---|
| 66 | H | H | H | CH₃CH₂ | 2-methylphenyl | 3-cyanophenyl |
| 67 | H | OMe | H | CH₃ | furan-3-yl | 2,4-bis(trifluoromethyl)phenyl |
| 68 | H | H | H | CH₃ | 3-(NHSO₂CH₃-methyl)phenyl | 3-methoxyphenyl |
| 69 | H | H | H | CH₃ | 3-(aminomethyl)phenyl | phenyl |
| 70 | H | H | H | CH₃ | 3-nitrophenyl | 2,5-dimethoxyphenyl |
| 71 | H | H | H | CN | 3-(2-hydroxyethyl)phenyl | 2,4-dimethylphenyl |

TABLE 2-continued (I)

| Example No. | R¹ | R² | R³ | R⁴ | Ar¹ | Ar² |
|---|---|---|---|---|---|---|
| 72 | H | H | H | CH₃ | 3-(1-hydroxyethyl)phenyl | 4-isopropylpyridin-3-yl |
| 73 | H | Me | H | CH₃ | 3-(cyanomethyl)phenyl | 2,4-difluorophenyl |
| 74 | H | H | H | (CH₃)₂CH | 3-((diethylamino)methyl)phenyl | 2-chloro-4-fluorophenyl |
| 75 | H | H | H | CH₃CH₂ | 3-(N-(2-methoxyethyl)sulfamoyl)phenyl | 2,4-difluorophenyl |
| 76 | H | H | H | C(O)NH₂ | 2,4-difluorophenyl | 2-chloro-4-fluorophenyl |
| 77 | H | Cl | H | CH₃ | 3-cyanophenyl | 4-isopropylpyridin-3-yl |

TABLE 2-continued

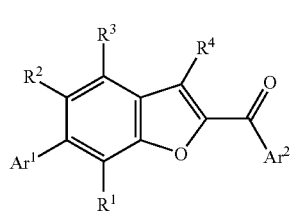

(I)

| Example No. | R¹ | R² | R³ | R⁴ | Ar¹ | Ar² |
|---|---|---|---|---|---|---|
| 78 | H | H | H | $CH_3$ | 3-(methoxycarbonylaminomethyl)phenyl | 2,4-dichlorophenyl |
| 79 | H | H | OH | $CH_3$ | 3-(cyclopropylcarbonylamino)phenyl | 2-bromo-4-fluorophenyl |
| 80 | H | H | H | $CH_3$ | 3-(N-(2-hydroxyethyl)sulfamoyl)phenyl | 3-nitrophenyl |
| 81 | H | Me | H | $CH_3$ | 3-((S)-2,3-dihydroxypropoxy)phenyl | 3-cyanophenyl |
| 82 | H | Cl | H | $(CH_3)_2CH$ | pyridin-3-yl N-oxide | 2,4-bis(trifluoromethyl)phenyl |
| 83 | H | $CF_3$ | H | $CH_3CH_2$ | 3-hydroxyphenyl | 3-methoxyphenyl |

TABLE 2-continued

| Example No. | R¹ | R² | R³ | R⁴ | Ar¹ | Ar² |
|---|---|---|---|---|---|---|
| 84 | H | OH | H | CH₃ | 2-tert-butyl-1-methyl-1H-imidazol-5-yl | phenyl |
| 85 | H | F | H | CH₃ | 5-tert-butyl-1-methyl-1H-imidazol-4-yl | 2-tert-butyl-4,5-dimethoxyphenyl (2-tBu, 2,5-diOMe) |
| 86 | H | EtO | H | CN | 3-[(4-methylpiperazin-1-yl)methyl]-5-tert-butylphenyl | 5-tert-butyl-2,4-dimethylphenyl |
| 87 | H | Cl | H | CH₃ | 3-(pyrrolidin-1-ylmethyl)-5-tert-butylphenyl | 3-tert-butyl-4-isopropylpyridin-... |
| 88 | H | CF₃O | H | C(O)NH₂ | 3-(imidazol-1-ylmethyl)-5-tert-butylphenyl | 5-tert-butyl-2,4-difluorophenyl |
| 89 | H | CH₃ | H | CH₃ | 5-tert-butyl-2-fluoro-3-cyanophenyl | 5-tert-butyl-2-chloro-4-fluorophenyl |
| 90 | H | H | H | CH₃ | 3-(cyclopropylaminocarbonyl)-5-tert-butylphenyl | 5-tert-butyl-2,4-difluorophenyl |

TABLE 2-continued

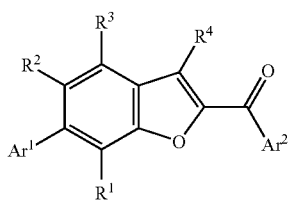

| Example No. | R¹ | R² | R³ | R⁴ | Ar¹ | Ar² |
|---|---|---|---|---|---|---|
| 91 | H | H | H | CH₃ | 3-(N-ethylcarbamoyl)phenyl with tert-butyl | 2-chloro-4-fluorophenyl with tert-butyl |
| 92 | H | H | H | (CH₃)₂CH | 3-(2-hydroxypropan-2-yl)phenyl with tert-butyl | 4-isopropylpyridin-3-yl with tert-butyl |
| 93 | H | H | H | CH₃CH₂ | 3-(N-(2-hydroxyethyl)carbamoyl)phenyl with tert-butyl | 2,4-dichlorophenyl with tert-butyl |
| 94 | H | H | H | CH₃ | 3-fluoro-5-nitrophenyl with tert-butyl | 2-bromo-4-fluorophenyl with tert-butyl |
| 95 | H | H | H | CH₃ | 3-(N-(2-methoxyethyl)carbamoyl)phenyl with tert-butyl | 3-nitrophenyl with tert-butyl |
| 96 | H | Cl | H | CH₃ | 3-((2S)-2,3-dihydroxypropoxy)phenyl with tert-butyl | 3-cyanophenyl with tert-butyl |

TABLE 2-continued (I)

| Example No. | R¹ | R² | R³ | R⁴ | Ar¹ | Ar² |
|---|---|---|---|---|---|---|
| 97 | H | F | H | CN | 3-(N-methylaminocarbonylmethyl)-5-tert-butylphenyl | 2,4-bis(trifluoromethyl)-phenyl (with t-Bu) |
| 98 | H | Me | H | $CH_3$ | 3-(N-methylaminosulfonyl)-5-tert-butylphenyl | 3-methoxy-5-tert-butylphenyl |
| 99 | H | H | OMe | $C(O)NH_2$ | 3-(N-ethylaminosulfonyl)-5-tert-butylphenyl | tert-butylphenyl |
| 100 | H | OH | H | $CH_3$ | 2-fluoro-3-tert-butylpyridin-yl | 2,5-dimethoxy-4-tert-butylphenyl |
| 101 | H | H | H | $CH_3$ | 2-methoxy-3-tert-butylpyridin-yl | 2,4-dimethyl-5-tert-butylphenyl |
| 102 | H | H | H | $(CH_3)_2CH$ | 2-chloro-3-tert-butylpyridin-yl | 4-isopropyl-3-tert-butylpyridin-yl |
| 103 | H | H | H | $CH_3CH_2$ | 2-(N-methylamino)-3-tert-butylpyridin-yl | 2,4-difluoro-5-tert-butylphenyl |

TABLE 2-continued
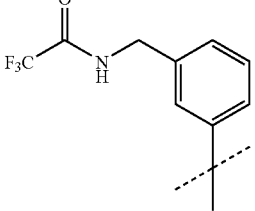
| Example No. | R¹ | R² | R³ | R⁴ | Ar¹ | Ar² |
|---|---|---|---|---|---|---|
| 104 | H | OH | H | CH₃ | 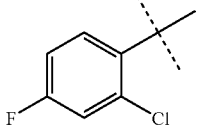 | 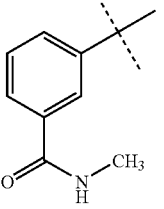 |
| 105 | H | H | H | CH₃ | 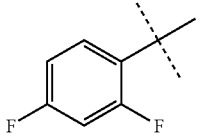 | 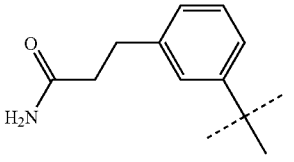 |
| 106 | H | H | H | CN | 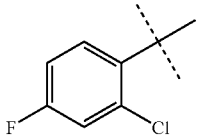 | 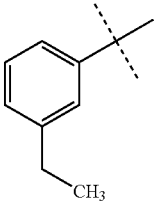 |
| 107 | H | H | Cl | CH₃ | 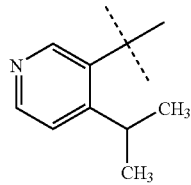 | 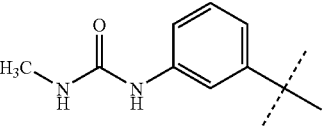 |
| 108 | H | H | H | CH₃ | 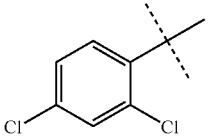 | 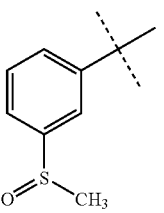 |
| 109 | H | H | H | CH₃ | 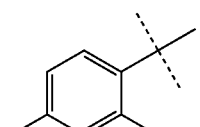 |  |

TABLE 2-continued

Structure (I): benzofuran core with substituents R¹ (7-position), Ar¹ (6-position), R² (5-position), R³ (4-position), R⁴ (3-position), and C(O)Ar² at the 2-position.

| Example No. | R¹ | R² | R³ | R⁴ | Ar¹ | Ar² |
|---|---|---|---|---|---|---|
| 110 | H | H | CF₃ | C(O)NH₂ | 3,5-difluorophenyl | 3-nitrophenyl |
| 111 | H | OMe | H | CH₃ | 4-methylthiophen-3-yl | 3-cyanophenyl |
| 112 | H | OH | H | (CH₃)₂CH | 3-(methylsulfonylamino)phenyl | 2,4-bis(trifluoromethyl)phenyl |
| 113 | H | Me | H | CH₃CH₂ | 3-acetylphenyl | 3-methoxyphenyl |
| 114 | H | Cl | H | CH₃ | 3-(3-morpholinopropanoyl)phenyl | phenyl |
| 115 | H | F | H | CH₃ | 3-formylthiophen-2-yl | 2,5-dimethoxyphenyl |
| 116 | H | Et | H | CH₃ | 2-methylthiazol-4-yl | 2,4-dimethylphenyl |

TABLE 2-continued

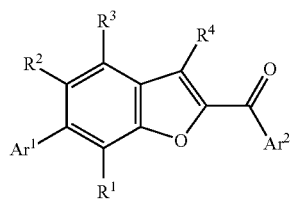
(I)

| Example No. | R¹ | R² | R³ | R⁴ | Ar¹ | Ar² |
|---|---|---|---|---|---|---|
| 117 | H | CF₃O | H | CN | 3-thienyl | 3-(1-methyl-1-methylethyl)-4-(1-methylethyl)pyridinyl |
| 118 | H | H | H | CH₃ | 3,5-dimethylisoxazol-4-yl | 2,4-difluorophenyl |
| 119 | H | H | H | CH₃ | 2-methyloxazol-4-yl | 2-chloro-4-fluorophenyl |
| 120 | H | Me | H | C(O)NH₂ | 5-acetylthien-2-yl | 2,4-difluorophenyl |
| 121 | H | OH | H | (CH₃)₂CH | 3-methoxyphenyl | 2-chloro-4-fluorophenyl |
| 122 | H | H | H | CH₃CH₂ | 3-fluorophenyl | 3-(1-methyl-1-methylethyl)-4-(1-methylethyl)pyridinyl |
| 123 | H | H | H | CH₃ | 4-acetyl-2-chlorophenyl | 2,4-dimethylphenyl |

TABLE 2-continued

Structure (I):

Benzofuran core with substituents $R^1$, $R^2$, $R^3$, $R^4$, $Ar^1$, and C(=O)$Ar^2$ at the 2-position.

| Example No. | $R^1$ | $R^2$ | $R^3$ | $R^4$ | $Ar^1$ | $Ar^2$ |
|---|---|---|---|---|---|---|
| 124 | H | H | OH | $CH_3$ | 3-aminophenyl | 2-chloro-4-fluorophenyl |
| 125 | H | H | H | $CH_3$ | 4-ethylphenyl | 2,4-dimethylphenyl |
| 126 | H | H | H | CN | 3-(methylsulfonyl)phenyl | 4-isopropylpyridin-3-yl |
| 127 | H | OH | H | $CH_3$ | 3-(methylthio)phenyl | 2-methoxyphenyl |
| 128 | Cl | H | F | $CH_3$ | 3-(ethylsulfonylamino)phenyl | 2-chloro-4-fluorophenyl |
| 129 | Me | H | Cl | $C(O)NH_2$ | 3-(N,N-dimethylsulfamoylamino)phenyl | 4-fluoro-2-methoxyphenyl |

TABLE 2-continued

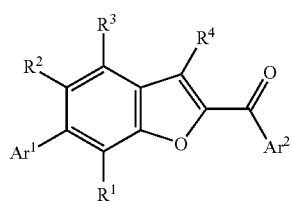

(I)

| Example No. | R¹ | R² | R³ | R⁴ | Ar¹ | Ar² |
|---|---|---|---|---|---|---|
| 130 | H | Me | H | (CH₃)₂CH | 3-tert-butyl-1-methyl-1H-pyrazol-5-yl | 3-isopropyl-pyridin-4-yl |
| 131 | H | H | H | CH₃CH₂ | 4-methylthiophen-3-yl | 2-methoxyphenyl |
| 132 | H | H | H | CH₃ | 2-methoxyphenyl | 4-fluoro-2-chlorophenyl |
| 133 | H | H | H | CH₃ | 3-((6-trifluoromethyl-pyridin-2-yl)methyl)phenyl | 4-fluoro-2-methoxyphenyl |
| 134 | H | H | Cl | CN | 3-(pyrimidin-2-ylmethyl)phenyl | benzo[1,3]dioxol-4-yl |
| 135 | H | H | H | CH₃ | 4-((6-methoxy-pyridin-2-yl)methyl)phenyl | 4-fluoro-2-bromophenyl |
| 136 | H | H | H | CH₃ | 3-methylthiophen-2-yl | 3-nitrophenyl |

US 7,803,956 B2
73  74
TABLE 2-continued
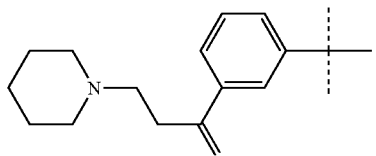
(I)
| Example No. | R¹ | R² | R³ | R⁴ | Ar¹ | Ar² |
|---|---|---|---|---|---|---|
| 137 | H | H | H | CH₃ | 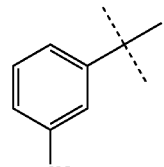 | 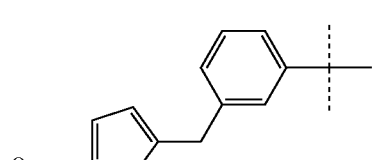 |
| 138 | H | H | OH | C(O)NH₂ | 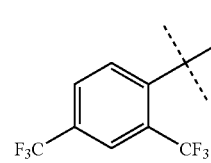 | 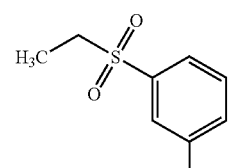 |
| 139 | H | Me | H | (CH₃)₂CH | 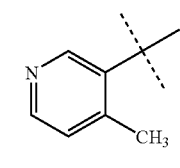 | 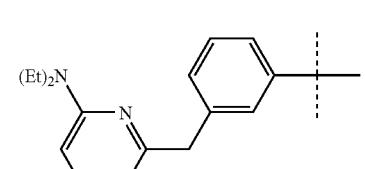 |
| 140 | H | H | H | CH₃CH₂ | 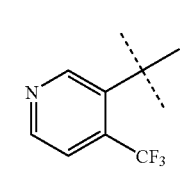 | 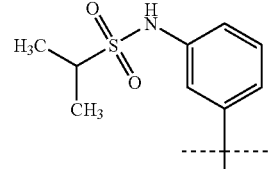 |
| 141 | H | H | H | CH₃ | 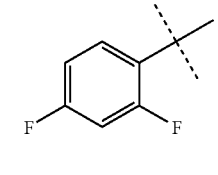 | 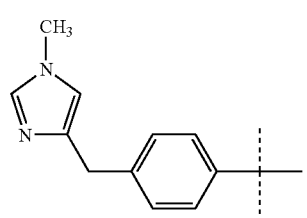 |
| 142 | H | H | MeO | CH₃ | 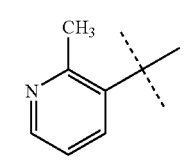 |  |

TABLE 2-continued
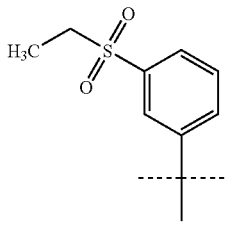
(I)
| Example No. | R¹ | R² | R³ | R⁴ | Ar¹ | Ar² |
|---|---|---|---|---|---|---|
| 143 | H | H | H | CN | 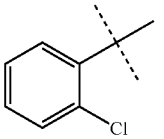 | 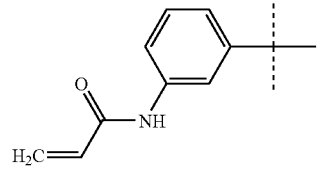 |
| 144 | H | MeO | H | CH₃ | 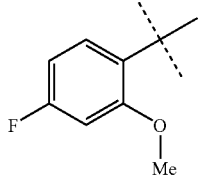 | 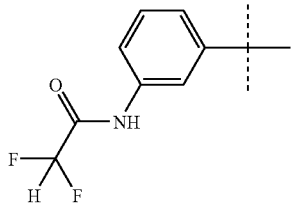 |
| 145 | H | H | H | CH₃ | 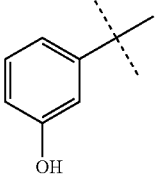 | 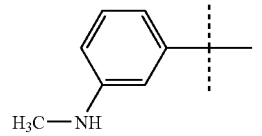 |
| 146 | H | H | H | CH₃ | 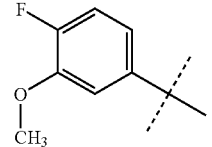 | 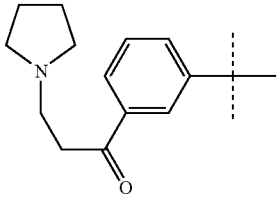 |
| 147 | H | H | Cl | C(O)NH₂ | 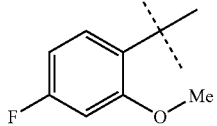 | 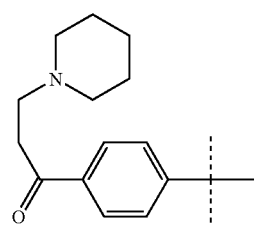 |
| 148 | H | H | H | CH₃ | 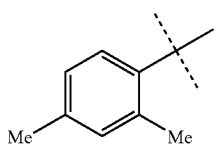 |  |

TABLE 2-continued (I)

| Example No. | R¹ | R² | R³ | R⁴ | Ar¹ | Ar² |
|---|---|---|---|---|---|---|
| 149 | OH | H | H | (CH₃)₂CH | N-pyrrolidinone | 2,4-dichlorophenyl |
| 150 | H | H | OH | CH₃CH₂ | imidazolidinone-NH | 3-cyanophenyl |
| 151 | OH | H | H | CH₃ | 1,3-dimethylimidazolidin-2-one | 2,4-bis(trifluoromethyl)phenyl |
| 152 | OH | H | H | CN | pyrrolidinyl | 3-methoxyphenyl |
| 153 | H | OH | H | CH₃ | pyrrolyl | phenyl |
| 154 | H | H | OH | CH₃ | imidazolyl | 2,5-dimethoxyphenyl |
| 155 | OH | OH | H | C(O)NH₂ | pyrazolyl | 2,4-dichlorophenyl |

TABLE 2-continued

| Example No. | R¹ | R² | R³ | R⁴ | Ar¹ | Ar² |
|---|---|---|---|---|---|---|
| 156 | F | H | H | CH₃ | 4-chloro-1-(t-butyl)pyrazol-1-yl | 4-fluoro-2-bromophenyl |
| 157 | H | H | F | CH₃ | 3-(acetamidoacetamido)phenyl | 3-nitrophenyl |
| 158 | F | H | F | CH₃ | 3-[3-(4-methylpiperazin-1-yl)propanoyl]phenyl | 3-cyanophenyl |
| 159 | H | H | H | (CH₃)₂CH | 3-[(2-oxopyrrolidin-1-yl)methyl]phenyl | 2,4-bis(trifluoromethyl)phenyl |
| 160 | H | H | H | CH₃CH₂ | 3-[(3-methyl-2-oxoimidazolidin-1-yl)methyl]phenyl | 3-methoxyphenyl |
| 161 | H | H | H | CH₃ | 3-[(2-oxooxazolidin-3-yl)methyl]phenyl | phenyl |
| 162 | H | H | H | CN | 3-[(2S)-2-aminopropanamido]phenyl | 2,5-dimethoxyphenyl |

TABLE 2-continued

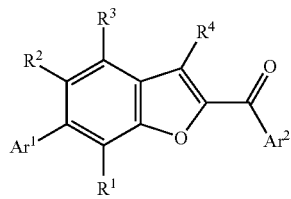
(I)

| Example No. | R¹ | R² | R³ | R⁴ | Ar¹ | Ar² |
|---|---|---|---|---|---|---|
| 163 | OH | H | H | CH₃ | 3-(tert-butyl)phenyl-NH-CH₂-CH(OH)-CH₃ | 2-(tert-butyl)-4,6-dimethylphenyl |
| 164 | H | OH | H | CH₃ | HO-CH₂-C*H(OH)-CH₂-NH-(3-tert-butylphenyl) | 3-(tert-butyl)-4-isopropylpyridin-4-yl |
| 165 | H | OH | H | CH₃ | H₃CO-CH₂-CH(OH)-CH₂-NH-(3-tert-butylphenyl) | 2-(tert-butyl)-4,5-difluorophenyl |
| 166 | H | H | H | C(O)NH₂ | 3-(H₂NC(O))phenyl-(tert-butyl) | 2-chloro-4-fluoro-6-(tert-butyl)phenyl |
| 167 | H | OH | H | CH₃ | 3-(F₃C-C(O)NH)phenyl-(tert-butyl) | 2-(tert-butyl)-4,5-difluorophenyl |
| 168 | H | H | H | (CH₃)₂CH | 3-(H₃CO-C(O)NH)phenyl-(tert-butyl) | 2-chloro-4-fluoro-6-(tert-butyl)phenyl |

TABLE 2-continued

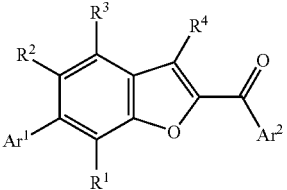

| Example No. | R¹ | R² | R³ | R⁴ | Ar¹ | Ar² |
|---|---|---|---|---|---|---|
| 169 | H | OH | H | CH₃ | | |

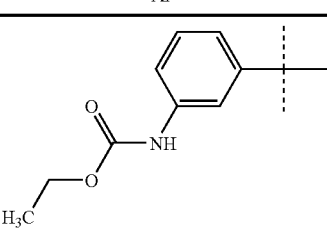

The compound structures of Table 1 correspond to the IUPAC compound names in Table 3 below.

TABLE 3

| Example No. | IUPAC Name |
|---|---|
| 1 | (2,4-Dichloro-phenyl)-(3-methyl-6-pyridin-3-yl-benzofuran-2-yl)-methanone |
| 2 | (2,4-Dichloro-phenyl)-(3-methyl-6-m-tolyl-benzofuran-2-yl)-methanone |
| 3 | 3-[2-(2,4-Dichloro-benzoyl)-3-methyl-benzofuran-6-yl]-benzonitrile |
| 4 | N-{3-[2-(2,4-Dichloro-benzoyl)-3-methyl-benzofuran-6-yl]-phenyl}-methanesulfonamide |
| 5 | N-{3-[2-(2,4-Dichloro-benzoyl)-3-methyl-benzofuran-6-yl]-benzyl}-acetamide |
| 6 | 2-{3-[2-(2,4-Dichloro-benzoyl)-3-methyl-benzofuran-6-yl]-phenyl}-acetamide |
| 7 | (2,4-Dichloro-phenyl)-[6-(3-methoxy-phenyl)-3-methyl-benzofuran-2-yl]-methanone |
| 8 | 1-{3-[2-(2,4-Dichloro-benzoyl)-3-methyl-benzofuran-6-yl]-phenyl}-ethanone |
| 9 | [6-(3-Aminomethyl-phenyl)-3-methyl-benzofuran-2-yl]-(2,4-dichloro-phenyl)-methanone; compound with trifluoro-acetic acid |
| 10 | N-{3-[2-(2,4-Dichloro-benzoyl)-3-methyl-benzofuran-6-yl]-phenyl}-2,2,2-trifluoro-acetamide |
| 11 | {3-[2-(2,4-Dichloro-benzoyl)-3-methyl-benzofuran-6-yl]-phenyl}-carbamic acid methyl ester |
| 12 | {3-[2-(2,4-Dichloro-benzoyl)-3-methyl-benzofuran-6-yl]-phenyl}-carbamic acid ethyl ester |
| 13 | N-{3-[2-(2,4-Dichloro-benzoyl)-3-methyl-benzofuran-6-yl]-phenyl}-acrylamide |
| 14 | N-{3-[2-(2,4-Dichloro-benzoyl)-3-methyl-benzofuran-6-yl]-phenyl}-2,2-difluoro-acetamide |
| 15 | {3-[2-(2,4-Dichloro-benzoyl)-3-methyl-benzofuran-6-yl]-benzyl}-carbamic acid methyl ester |
| 16 | {3-[2-(2,4-Dichloro-benzoyl)-3-methyl-benzofuran-6-yl]-benzyl}-carbamic acid ethyl ester |
| 17 | N-{3-[2-(2,4-Dichloro-benzoyl)-3-methyl-benzofuran-6-yl]-benzyl}-acrylamide |
| 18 | [6-(3-Chloro-phenyl)-3-methyl-benzofuran-2-yl]-(2,4-dichloro-phenyl)-methanone |
| 19 | (2,4-Dichloro-phenyl)-[3-methyl-6-(3-trifluoromethyl-phenyl)-benzofuran-2-yl]-methanone |
| 20 | [6-(2-Chloro-phenyl)-3-methyl-benzofuran-2-yl]-(2,4-dichloro-phenyl)-methanone |
| 21 | (2,4-Dichloro-phenyl)-[6-(3,4-dimethoxy-phenyl)-3-methyl-benzofuran-2-yl]-methanone |
| 22 | (2,4-Dichloro-phenyl)-[3-methyl-6-(3-nitro-phenyl)-benzofuran-2-yl]-methanone |

TABLE 3-continued

| Example No. | IUPAC Name |
|---|---|
| 23 | (2,4-Dichloro-phenyl)-[6-(3,4-dimethyl-phenyl)-3-methyl-benzofuran-2-yl]-methanone |
| 24 | (2,4-Dichloro-phenyl)-[6-(2-fluoro-phenyl)-3-methyl-benzofuran-2-yl]-methanone |
| 25 | 3-[2-(2,4-Dichloro-benzoyl)-3-methyl-benzofuran-6-yl]-benzaldehyde |
| 26 | N-{3-[2-(2,4-Dichloro-benzoyl)-3-methyl-benzofuran-6-yl]-benzyl}-methanesulfonamide |
| 27 | N-{3-[2-(Benzo[1,3]dioxole-4-carbonyl)-3-ethyl-benzofuran-6-yl]-phenyl}-acetamide |
| 28 | N-{3-[2-(2,4-Dichloro-benzoyl)-3-ethyl-benzofuran-6-yl]-phenyl}-acetamide |
| 29 | (2,4-Dichloro-phenyl)-(3-ethyl-6-pyridin-3-yl-benzofuran-2-yl)-methanone |
| 30 | N-{3-[3-Ethyl-2-(2-methoxy-benzoyl)-benzofuran-6-yl]-phenyl}-acetamide |
| 31 | 3-[2-(2,4-Dichloro-benzoyl)-3-ethyl-benzofuran-6-yl]-benzonitrile |
| 32 | 3-[3-Ethyl-2-(2-methoxy-benzoyl)-benzofuran-6-yl]-benzonitrile |
| 33 | 3-[2-(2,4-Dichloro-benzoyl)-3-isopropyl-benzofuran-6-yl]-benzonitrile |
| 34 | N-{3-[2-(2,4-Dichloro-benzoyl)-3-isopropyl-benzofuran-6-yl]-phenyl}-acetamide |
| 35 | N-{3-[2-(2,4-Dichloro-benzoyl)-3-isopropyl-benzofuran-6-yl]-phenyl}-methanesulfonamide |
| 36 | N-{3-[2-(2,4-Dichloro-benzoyl)-3-isopropyl-benzofuran-6-yl]-benzyl}-acetamide |
| 37 | 2-{3-[2-(2,4-Dichloro-benzoyl)-3-isopropyl-benzofuran-6-yl]-phenyl}-acetamide |
| 38 | 2-(2,4-Dichloro-benzoyl)-6-pyridin-3-yl-benzofuran-3-carboxylic acid amide |
| 39 | 6-(3-Cyano-phenyl)-2-(2,4-dichloro-benzoyl)-benzofuran-3-carboxylic acid amide |
| 40 | 6-(3-Cyano-phenyl)-2-(2,4-dichloro-benzoyl)-benzofuran-3-carboxylic acid methylamide |
| 41 | 6-(3-Cyano-phenyl)-2-(2,4-dichloro-benzoyl)-benzofuran-3-carbonitrile |
| 42 | 6-(3-Cyano-phenyl)-2-(2,4-dichloro-benzoyl)-benzofuran-3-carbonitrile |
| 43 | 2-(2,4-Dichloro-benzoyl)-6-(3-methoxy-phenyl)-benzofuran-3-carboxylic acid amide |
| 44 | 2-(2,4-Dichloro-benzoyl)-6-m-tolyl-benzofuran-3-carbonitrile |
| 45 | 2-(2,4-Dichloro-benzoyl)-6-(3-methoxy-phenyl)-benzofuran-3-carbonitrile |
| 46 | 2-(2,4-Dichloro-benzoyl)-6-(3-nitro-phenyl)-benzofuran-3-carbonitrile |
| 170 | N-[3-(2-(2,4-dichlorobenzoyl)-3-{[(2-methoxyethyl)amino]methyl}-1-benzofuran-6-yl)benzyl]methanesulfonamide trifluoroacetate |
| 171 | N-[3-(2-(2,4-dichlorobenzoyl)-3-{[(2-methoxyethyl)amino]methyl}-1-benzofuran-6-yl)phenyl]methanesulfonamide |
| 172 | N-[3-(2-(2,4-dichlorobenzoyl)-3-{[(2-methoxyethyl)(methyl)amino]methyl}-1-benzofuran-6-yl)phenyl]methanesulfonamide |
| 173 | N-[3-(2-(2,4-dichlorobenzoyl)-3-{[(2-hydroxyethyl)(methyl)amino]methyl}-1-benzofuran-6-yl)benzyl]methanesulfonamide |
| 174 | N-[3-(2-(2,4-dichlorobenzoyl)-3-{[(2-hydroxyethyl)(methyl)amino]methyl}-1-benzofuran-6-yl)phenyl]methanesulfonamide |
| 175 | N-[3-(2-(2,4-dichlorobenzoyl)-3-{[(2-methoxyethyl)(propyl)amino]methyl}-1-benzofuran-6-yl)phenyl]methanesulfonamide |
| 176 | N-{3-[2-(2,4-dichlorobenzoyl)-3-(trifluoromethyl)-1-benzofuran-6-yl]phenyl}acetamide |
| 177 | N-{3-[2-(2,4-dichlorobenzoyl)-3-(methoxymethyl)-1-benzofuran-6-yl]phenyl}methanesulfonamide |
| 178 | N-{3-[2-(2,4-dichlorobenzoyl)-3-(methoxymethyl)-1-benzofuran-6-yl]benzyl}acetamide |
| 179 | N-{3-[2-(2,4-dichlorobenzoyl)-3-(methoxymethyl)-1-benzofuran-6-yl]phenyl}acetamide |
| 180 | N-{3-[2-(2,4-dichlorobenzoyl)-3-(trifluoromethyl)-1-benzofuran-6-yl]phenyl}methanesulfonamide |
| 181 | [6-(3-aminophenyl)-3-(trifluoromethyl)-1-benzofuran-2-yl](2,4-dichlorophenyl)methanone |
| 182 | (2,4-dichlorophenyl){6-[3-(hydroxymethyl)phenyl]-3-methyl-1-benzofuran-2-yl}methanone |
| 183 | (2,4-dichlorophenyl)(6-pyridin-3-yl-1-benzofuran-2-yl)methanone |
| 184 | N-{3-[2-(2,4-dichlorobenzoyl)-1-benzofuran-6-yl]phenyl}methanesulfonamide |
| 185 | (2,4-dichlorophenyl){6-[3-{hydroxymethyl)phenyl]-1-benzofuran-2-yl}methanone |
| 186 | 3-[2-(2,4-dichlorobenzoyl)-3-methyl-1-benzofuran-6-yl]benzamide |

TABLE 3-continued

| Example No. | IUPAC Name |
|---|---|
| 187 | 3-[2-(2,4-dichlorobenzoyl)-3-methyl-1-benzofuran-6-yl]-N-(2-methoxyethyl)benzamide |
| 188 | 3-[2-(2-methoxybenzoyl)-3-methyl-1-benzofuran-6-yl]benzamide |
| 189 | 2-{3-[2-(2-methoxybenzoyl)-3-methyl-1-benzofuran-6-yl]phenyl}acetamide |
| 190 | (2,4-dichlorophenyl){6-[3-({[2-(dimethylamino)ethyl]amino}methyl)phenyl]-3-methyl-1-benzofuran-2-yl}methanone |
| 191 | N-[3-(2-{(2Z)-2-[(1E)-1,3-dichloroprop-1-en-1-yl]penta-2,4-dienoyl}-3-methoxy-1-benzofuran-6-yl)phenyl]methanesulfonamide |
| 192 | N-[3-(2-{(2Z)-2-(1E)-1,3-dichloroprop-1-en-1-yl]penta-2,4-dienoyl}-3-methoxy-1-benzofuran-6-yl)phenyl]acetamide |
| 193 | (2Z)-2-[(1E)-1,3-dichloroprop-1-en-1-yl]-1-{6-[3-(hydroxymethyl)phenyl]-3-methoxy-1-benzofuran-2-yl}penta-2,4-dien-1-one |
| 194 | N-[3-(2-{(2Z)-2-[(1E)-1,3-dichloroprop-1-en-1-yl]penta-2,4-dienoyl}-3-methoxy-1-benzofuran-6-yl)benzyl]methanesulfonamide |
| 195 | 3-[2-(2,4-dimethoxybenzoyl)-3-methyl-1-benzofuran-6-yl]benzonitrile |
| 196 | {6-[3-(4,5-dihydro-1H-imidazol-2-yl)phenyl]-3-methyl-1-benzofuran-2-yl}(2-methoxyphenyl)methanone |
| 197 | [6-(6-aminopyridin-2-yl)-3-methyl-1-benzofuran-2-yl](2,4-dichlorophenyl)methanone |
| 198 | (2,4-dichlorophenyl){6-[3-(2-hydroxyethyl)phenyl]-3-methyl-1-benzofuran-2-yl}methanone |
| 199 | N-Carbamoylmethyl-2-{3-[2-{2,4-dichoro-benzoyl)-3-methyl-benzofuran-6-yl]-phenyl}-acetamide* |
| 200 | 2-{3-[2-(2,4-Dichloro-benzoyl)-3-methyl-benzofuran-6-yl]-benzylamino}-acetamide* |
| 201 | N-Carbamoylmethyl-2-(3-[2-(2,4-dimethoxy-benzoyl)-3-methyl-benzofuran-6-yl]-phenyl}-acetamide* |
| 202 | (2,4-dimethoxyphenyl){6-[3-(hydroxymethyl)phenyl]-3-methyl-1-benzofuran-2-yl}methanone |
| 203 | N-{3-[2-(2,4-dimethoxybenzoyl)-3-methyl-1-benzofuran-6-yl]phenyl}acetamide |
| 204 | N-{3-[2-(2,4-dimethoxybenzoyl)-3-methyl-1-benzofuran-6-yl]phenyl}methanesulfonamide |
| 205 | 2-{3-[2-(2,4-dimethoxybenzoyl)-3-methyl-1-benzofuran-6-yl]phenyl}acetamide |
| 206 | (2,4-dichlorophenyl){6-[6-(hydroxymethyl)pyridin-2-yl]-3-methyl-1-benzofuran-2-yl}methanone |
| 207 | N-(2-amino-2-oxoethyl)-3-[2-(2,4-dichlorobenzoyl)-3-methyl-1-benzofuran-6-yl]benzamide |
| 208 | (2,4-dimethoxyphenyl){6-[6-(hydroxymethyl)pyridin-2-yl]-3-methyl-1-benzofuran-2-yl}methanone |
| 209 | 2-{6-[2-(2,4-dichlorobenzoyl)-3-methyl-1-benzofuran-6-yl]pyridin-2-yl}acetamide |
| 210 | N-({6-[2-(2,4-dichlorobenzoyl)-3-methyl-1-benzofuran-6-yl]pyridin-2-yl}methyl)acetamide |
| 211 | 6-[2-(2,4-dimethoxybenzoyl)-3-methyl-1-benzofuran-6-yl]pyridine-2-carboxamide |
| 212 | N-({6-[2-(2,4-dimethoxybenzoyl)-3-methyl-1-benzofuran-6-yl]pyridin-2-yl}methyl)acetamide |
| 213 | 2-{6-[2-(2,4-dimethoxybenzoyl)-3-methyl-1-benzofuran-6-yl]pyridin-2-yl}acetamide |
| 214 | 6-[2-(2,4-Dichloro-benzoyl)-3-methyl-benzofuran-6-yl]-pyridine-2-carboxylic acid amide |

*The IUPAC name was obtained using AutoNom 1.0 Add-In for IsisDraw from MDL Information Systems, Inc.

Asymmetry, ie, where a compound's mirror Image cannot be super-imposed on the compound, may be present in a compound of formula (I) due to the Inherent structure of the molecule. Examples of such asymmetric molecules include certain allenes. The compounds of this invention may also contain one or more asymmetric centers depending upon the location and nature of the various substituents selected. A molecule with a single asymmetric center may be a mixture of enantiomers (R,S), or may be a single (R) or (S) enantiomer. A molecule with more than one asymmetric center may be a mixture of diastereomers, or may be a single diastereomer. Additionally, a compound may exhibit asymmetry due to restricted rotation about a given bond, for example, the central bond adjoining two substituted aromatic rings of the specified compounds. It is intended that all such configurations and conformations (including enantiomers, diastereomers, and other optical Isomers) are included within the scope of the present invention. Separated, pure or partially purified stereo Isomers of the compounds of formula (I) are each included within the scope of the present invention. Preferred compounds are those with the absolute configuration or conformation which produces the more desirable biological activity.

Pharmaceutically acceptable salts of the compounds of this invention are also within the scope of this invention. The term "pharmaceutically acceptable salt" refers to an inorganic or organic salt of a compound of the present invention that has properties acceptable for therapeutic use. For example, see S. M. Berge, et al. "Pharmaceutical Salts," *J. Pharm. Sci.* 1977, 66, 1-19.

Representative salts of the compounds of this invention include the conventional non-toxic salts and the quaternary ammonium salts that are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate. The term acid addition salts also comprises the hydrates and the solvent addition forms which the compounds of this Invention are able to form. Examples of such forms are, for example, hydrates, alcoholates and the like.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others.

Unless the context clearly indicates to the contrary, whenever the term "compounds of this invention," "a compound of the present invention", and the like, are used herein, it is intended to include the chemically feasible pharmaceutically acceptable salts as well as all stereoisomeric forms of the referenced compounds.

Method of Making the Compounds of the Present Invention

In general, the compounds of this invention may be prepared by standard techniques known in the art, by known processes analogous thereto, and/or by the processes disclosed below, using starting materials which are either commercially available, producible according to routine, conventional chemical methods and/or the synthesis of which is described herein.

The particular process to be utilized in the preparation of the compounds of this invention depends upon the specific compound desired. Such factors as whether the 3-benzofuran position is substituted with $(C_1-C_3)$ alkyl, $C(O)NHR^5$ or with CN, and the selection of the specific substituents possible at various other locations on the molecule, each play a role in which path will be followed in the preparation of the specific compounds of this invention. Those factors are readily recognized by one of ordinary skill in the art.

ABBREVIATIONS

When the following abbreviations are used herein, they have the following meaning:

| | |
|---|---|
| DCM | dichloromethane |
| DMF | N,N-dimethylformamide |
| DMSO | dimethylsulfoxide |
| EDC | N-ethyl-N'-(3-dimethylaminopropyl)carbodiimide |
| EtMgBr | ethyl magnesium bromide |
| Et$_2$O | diethyl ether |
| EtOAc | ethyl acetate |
| EtOH | ethanol |
| HPLC ES-MS | high performance liquid chromatography-electrospray mass spectrometry |
| HOBt | 1-hydroxybenzotriazole |
| LC/MS | Liquid Chromatography/Mass Spectrometry |
| Me | methyl |
| MeOH | methanol |
| NaOH | sodium hydroxide |
| NMR | Nuclear Magnetic Resonance Spectroscopy |
| NBS | N-Bromosuccinimide |
| Nuc | Nucleophile |
| Pd | Palladium |
| Ph | phenyl |
| PyBOP | benzotriazole-1-yl-oxy-tris-pyrrolidino-phosphonium hexafluorophosphate |
| RT | retention time (HPLC) |
| R$_f$ | TLC Retention Factor |
| SOCl$_2$ | thionyl chloride |
| TBDMS | tert-butyldimethylsilane |
| TBDMSCl | tert-butyldimethylsilyl chloride |
| Tf | trifluoromethanesulfonyl |
| Tf$_2$O | trifluoromethanesulfonic anhydride |
| rt | room temperature |
| THF | tetrahydrofuran |
| TFA | trifluoroacetic acid |
| TLC | thin layer chromatography |

Generally, the benzofuran derivatives of formula (I) where $R^4$ is $(C_1-C_3)$alkyl can be prepared by the method outlined below in Reaction Scheme 1.

Reaction Scheme 1

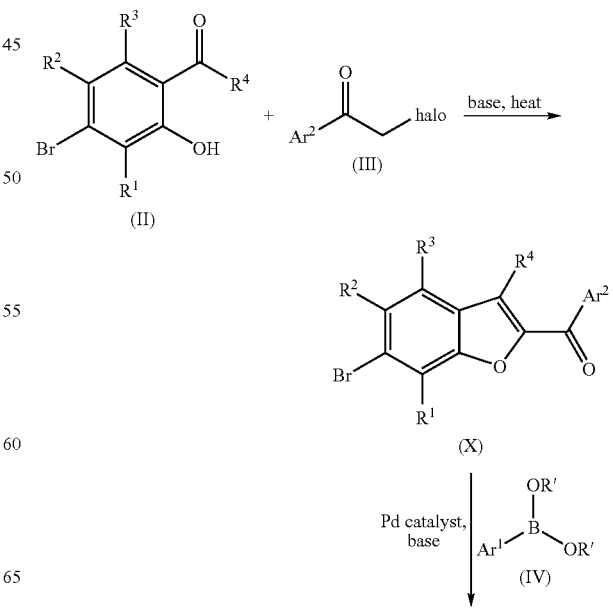

-continued

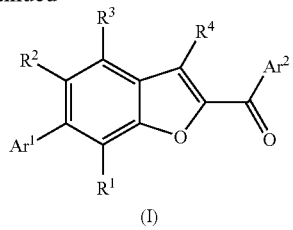
(I)

In Reaction Scheme 1, a benzofuran compound of formula (I) where $R^4$ is $(C_1-C_3)$alkyl may be synthesized by the condensation of a properly substituted 1-(4-bromo-2-hydroxyphenyl)alkanone of formula (II), with an appropriate arylhalomethylketone of formula (III) in the presence of a base such as cesium carbonate, potassium carbonate, sodium carbonate or DBU, In a solvent such as DMF or MeCN, and at a temperature between room temperature to 100° C., to yield a brominated benzofuranylketone compound (X). Compound (X) is then coupled to an appropriate boronic acid or boronate $Ar^1(BOR')_2$ of formula (IV) [where R' is selected in each instance independently from H and $(C_1-C_3)$alkyl and where, when both R' groups are $(C_1-C_3)$alkyl they may, together with the O atoms to which they are attached, form a five- or six-membered ring exemplified by (IVa) or (IVb) below], in the presence of a palladium catalyst and a base such as potassium acetate, to yield the desired compound of formula I.

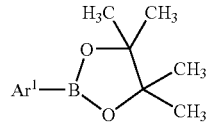
(IVa)

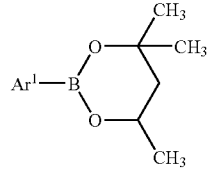
(IVb)

Preferably, R' is $(C_3)$alkyl in each instance, as in compound (IVa).

A compound of formula I where $R^4$ is CN or $C(O)NHR^5$ can generally be prepared according to Reaction Scheme 2.

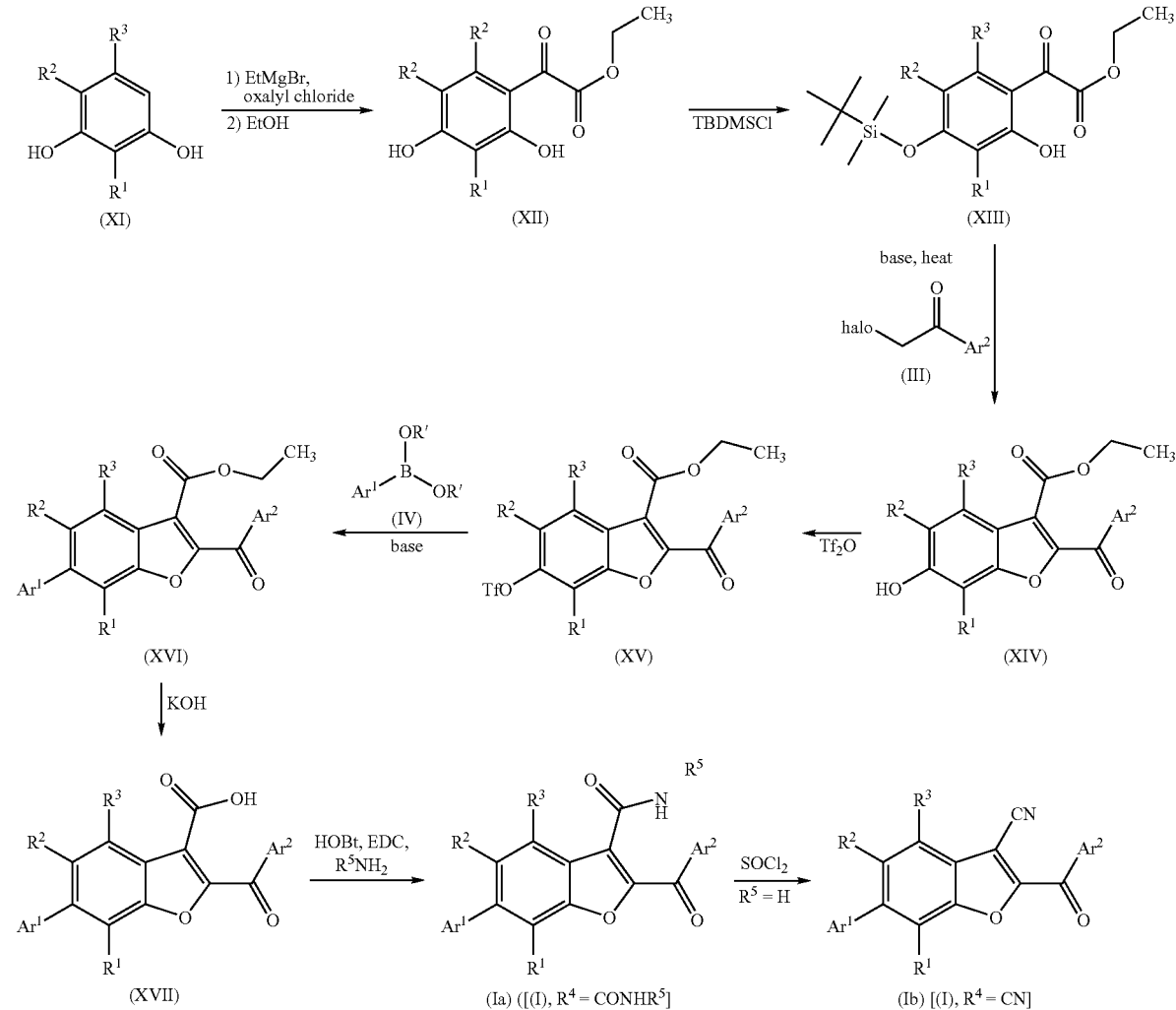

Reaction Scheme 2

A substitute dihydroxyphenyl compound of formula (XI) is reacted with oxalyl chloride in the presence of ethyl magnesium bromide and, subsequently, with ethanol, according to the procedures described by Franca Bigi in *J. Chem. Soc. Perkin Trans I* 1984, 2655, to yield a substituted dihydroxyphenyl-oxo-acetate of formula (XII). The appropriate hydroxy group on compound formula (XII) is then silyl-protected using TBDMSCI, to yield a silyl-protected-hydroxy oxalate of formula (XIII). The silyl-protected hydroxy oxalate (XIII) is subsequently reacted with an appropriate 1-aryl-2-haloethanone (III), said reaction being facilitated by a base such as cesium carbonate, potassium carbonate, sodium carbonate or DBU, in a solvent such as DMF or MeCN, and at a temperature between room temperature and 100° C., and is subsequently de-protected to yield a substituted benzofuran that includes the desired $Ar^2$ group (XIV). The hydroxy group on compound (XIV) is then converted into a leaving group by reacting it with $Tf_2O$, to form compound formula (XV). Compound (XV) is then coupled with an appropriate boronic acid or boronate $Ar^1(BOR')_2$ (IV), as described above, the coupling reaction being facilitated by a palladium catalyst in the presence of a base, to yield the biaryl benzofuran (XVI). Compound (XVI) is then converted to its corresponding carboxylic acid (XVII) using potassium hydroxide, and the resulting carboxylic acid (XVII) is then reacted with the appropriate amine ($R^5NH_2$) in the presence of hydroxybenzotriazole and EDC to form a biaryl benzofuran where $R^4$ is $C(O)NHR^5$ (Ia). Compound (Ia) where $R^5$ is H can subsequently be reacted with $SOCl_2$ to yield a compound of the invention where $R^4$ is CN (Ib).

Reaction Schemes 3, 4 and 5 show ways to synthesize the starting materials (II), (III) and (IV), respectively.

Reaction Scheme 3 depicts a three-step process for the preparation of the hydroxy ketones of formula (II) from their readily available corresponding fluoronitriles.

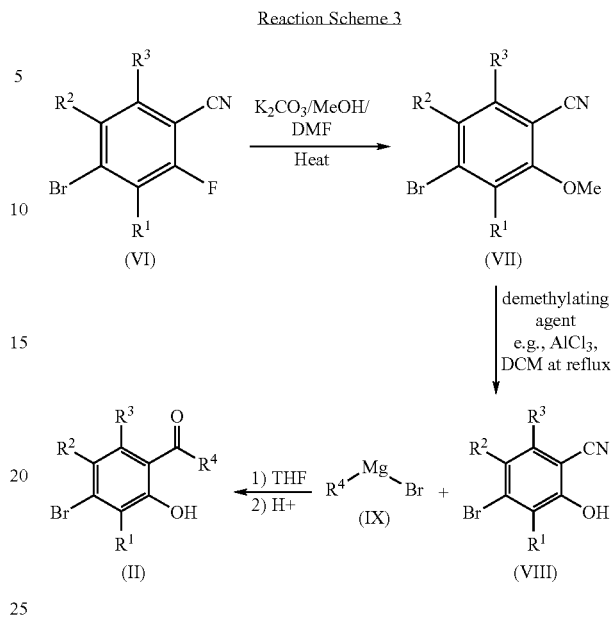

Reaction Scheme 3

The first step of Reaction Scheme 3 involves the nucleophilic displacement of fluorine on compound formula (VI) by a methoxide ion in a solvent such as DMF, under heat and facilitated by the presence of a base such as $K_2CO_3$ to yield compound formula (VII). The second step is the demethylation of the methyl ether of (VII) with a demethylating agent, for example $AlCl_3$, in a solvent such as DCM under argon and at reflux conditions to give the appropriate hydroxynitrile of formula (VIII). Finally, the hydroxynitrile (XIII) is reacted with $R^4MgBr$ in a Grignard reaction to yield the starting material (II).

Reaction Scheme 4 shows the synthesis of starting material (III).

Reaction Scheme 4

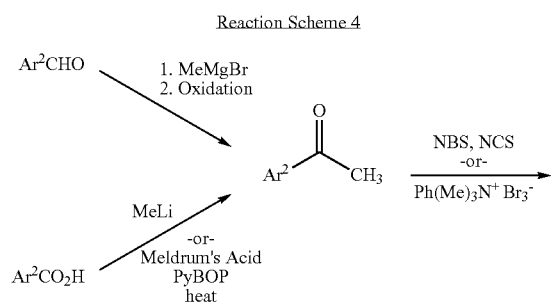

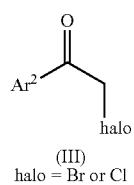

(III)
halo = Br or Cl

Reaction Scheme 4 depicts the preparation of aryl-halomethylketones of formula (III) by two routes. In one route, an arylaldehyde is converted to an intermediate aryl ketone by a Grignard reaction with methylmagnesium bromide, followed by oxidation of the intermediate alcohol under any of several methods, such as PCC, Swern, Dess-Martin or Moffat oxidations. Alternatively the intermediate aryl ketone can be prepared from the corresponding arylcarboxylic acid by reaction with methyllithium, or with Meldrum's acid in the presence of PyBOP. Halogenation of the intermediate aryl ketone to the aryl halomethylketone is carried out with any of the commonly used halogenation agents such as NBS, NCS or trimethylphenylammonloum perbromide. Such methods are well-known in the art and are specifically illustrated below as Methods A-1 to A-4.

Reaction Scheme 5 shows the preparation of the $Ar^1$-containing starting material (IV).

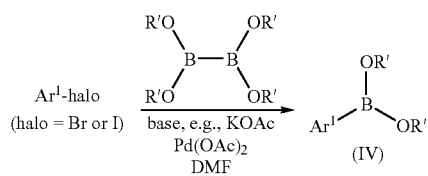

These aryl boronates of formula (IV) where R' is as defined above, are prepared from the corresponding aryl bromide or aryl iodide as shown in Reaction Scheme 5, by reaction with a boronic ester such as bis(pinacolato)diboron (Aldrich Chemical Co., Cat No. 47, 329-4), in the presence of a palladium catalyst such as palladium acetate, and a base such as potassium acetate. This sequence is specifically described below in Method B-1. Aryl halides are either commercially available or prepared by well-known methods in the art or exemplified below in Methods C- to C-14.

Reaction Scheme 6 depicts a variation of Reaction Schemes 1 and 2 for the preparation of formula (I) compounds In which $R^1$, $R^2$, and $R^3$ are H, $R^4$ is $(C_1-C_3)$alkyl, and $Ar^1$ and $Ar^2$ are as described above.

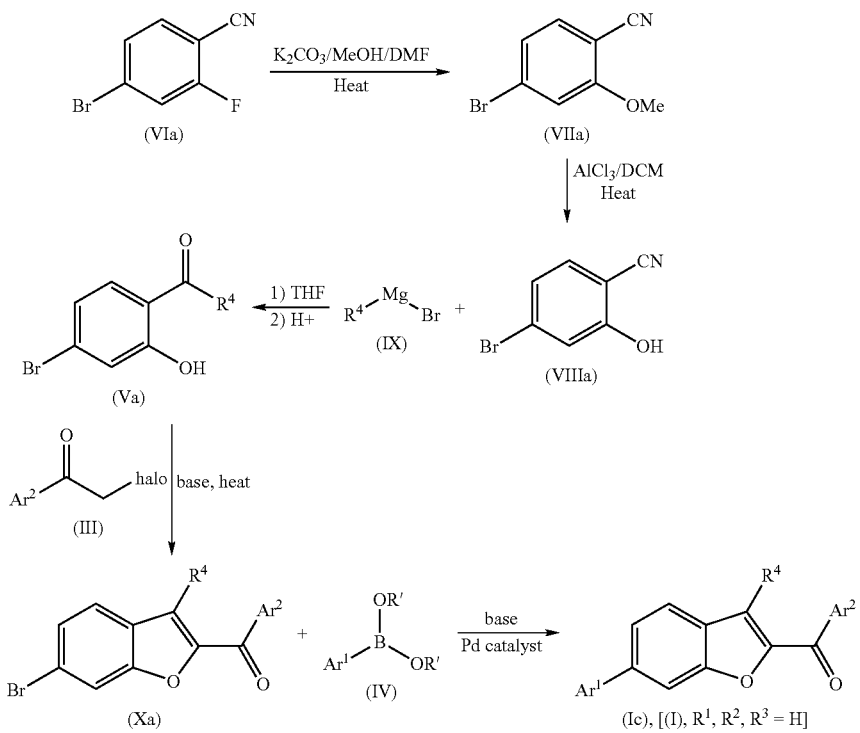

Starting material 4-bromo-2-fluoro-benzonitrile (Via) is reacted with MeOH under basic conditions to yield compound (VIIa). Intermediate (Vila) is demethylated using is aluminum chloride as the demethylating agent to yield compound (VIIIa). Intermediate (VIIIa) is then reacted with a magnesium bromide reagent (IX) in anhydrous THF to form the 2-hydroxyaryl ketone (Va). This preparation of intermediate (Va) is described in Wayne Vaccaro. *J. Med. Chem.*, 1996, 39, 1704. The appropriate haloarylketone (III) of Reaction Scheme IV, and a base such as potassium carbonate are added to intermediate (Va) in solvent such as DMF, and the mixture is heated to yield intermediate (Xa). Boronic acid or ester (IV) is allowed to react with intermediate (Xa) under Suzuki conditions to give the final compounds (Ic), i.e., formula (I), where $R^1$, $R^2$, and $R^3$ are each H.

An example of a formula (I) compound prepared using the method of Reaction Scheme 6 is described further in Specific Example 1 below.

A further variation of the methods of Reaction Schemes 1 and 2 is depicted in Reaction Scheme 7 below for the preparation of formula (I) compounds where $R^4$ is $C(O)NH_2$ or CN.

Reaction Scheme 7

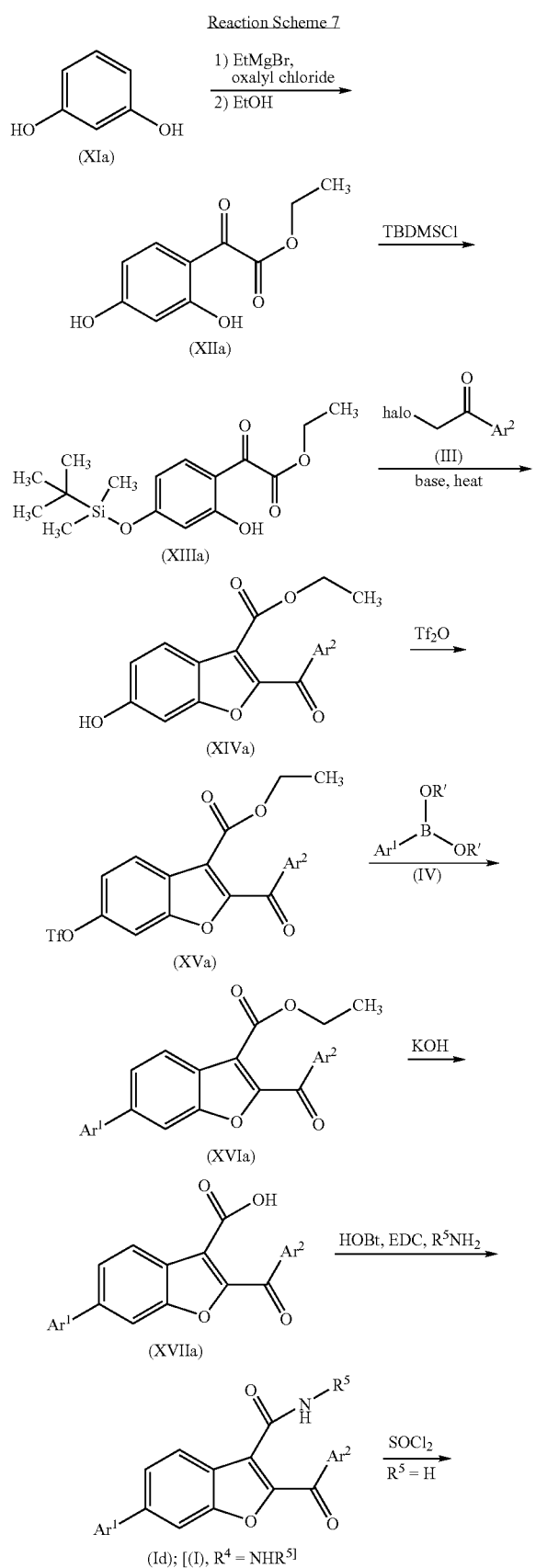

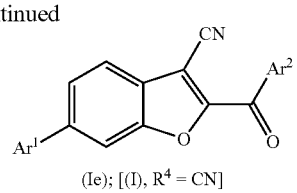

(Ie); [(I), R⁴ = CN]

Ethylmagnesium bromide reagent is allowed to react with resorcinol (XIa) and oxalyl chloride in toluene at room temperature and is then quenched with ethanol to give the dihydroxy carboxylic ester intermediate (XIIa), as described further in Franca Bigi in J. Chem. Soc. Perkin Trans I 1984, 2655. The (XIIa) is then selectively protected with a TBDMS group to form the monosilylated intermediate (XIIIa). An appropriate haloarylketone (III) and potassium carbonate are added to the intermediate (XIIIa) in DMF, and the mixture is heated under argon to yield the deprotected free hydroxy intermediate (XIVa). Conversion of free hydroxy (XIVa) via reaction with Tf$_2$O results in the intermediate (XVa) containing a triflate leaving group. Intermediate (XVa) is then reacted with boronic acid or ester (IV) under Suzuki conditions to give the aryl-benzofuran intermediate (XVIa) which is converted to its corresponding acid (XVIIa) under basic conditions. The acid (XVIIa) is then allowed to react with an appropriate amine (R⁵NH$_2$) under dehydrative coupling conditions [e.g., HOBt and EDC] to give the amide (Id), i.e., formula (I) where R⁴ is NHR⁵. Compound (Id) can be further converted to the nitrile compound (ie), i.e., formula (I) where R⁴ is CN, by reacting (Id) where R⁵ is H with thionyl chloride under refluxing conditions.

Specific examples of the preparation of the formula (Id) and (Ie) compounds using the methods of Reaction Scheme 7 are described further in Specific Examples 2 and 3 below.

A further variation of the methods of Reaction Schemes 1 and 2 is depicted in Reaction Scheme 8 below for the preparation of formula (I) compounds where R⁴ is CF$_3$ and Ar¹, Ar² and R' are as described above.

Reaction Scheme 8

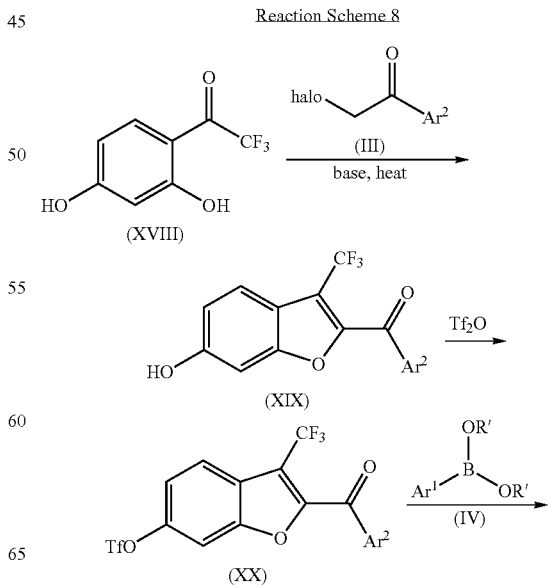

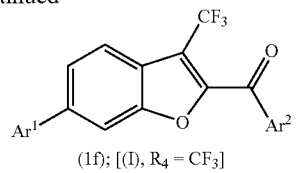

(1f); [(I), R$_4$ = CF$_3$]

In this sequence, the compound of formula (XVIII), prepared as described in the literature, can be treated with a halo ketone of formula (III), in a manner similar to that In Reaction Scheme 1, to provide the compound of formula (XIX). Conversion of the phenol (XIX) to the aryl triflate of formula (XX) can be accomplished with a variety of the known triflating reagents, such as trifluoroacetic anhydride. The product of formula (XX) is allowed to react with a boronic ester derivative of formula (IV) under Suzuki conditions to give the compound of formula (If).

An example of a formula (I) compound prepared using the method of Reaction Scheme 8 is described further in Specific Example 176 below.

A further variation of the methods of Reaction Schemes 1 and 2 is depicted in Reaction Scheme 9 below for the preparation of formula (I) compounds where R$^4$ is alkoxy.

An example of a formula (I) compound prepared using the method of Reaction Scheme 9 is described further in Specific Example 194 below.

A further variation of the methods of Reaction Schemes 1 and 2 is depicted in Reaction Scheme 10 below for the preparation of formula (I) compounds where R$^4$ is CH$_2$Nuc, and Nuc is CH$_2$Oalkyl or CH$_2$NR$^5$R$^5$.

Reaction Scheme 10

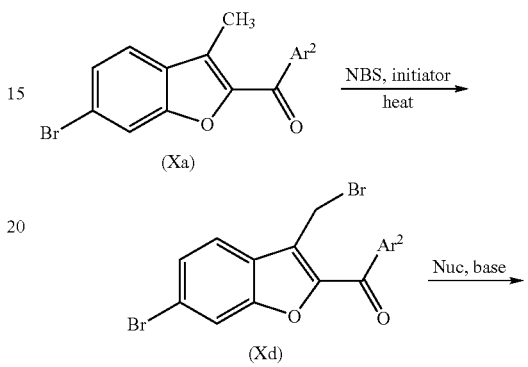

Reaction Scheme 9

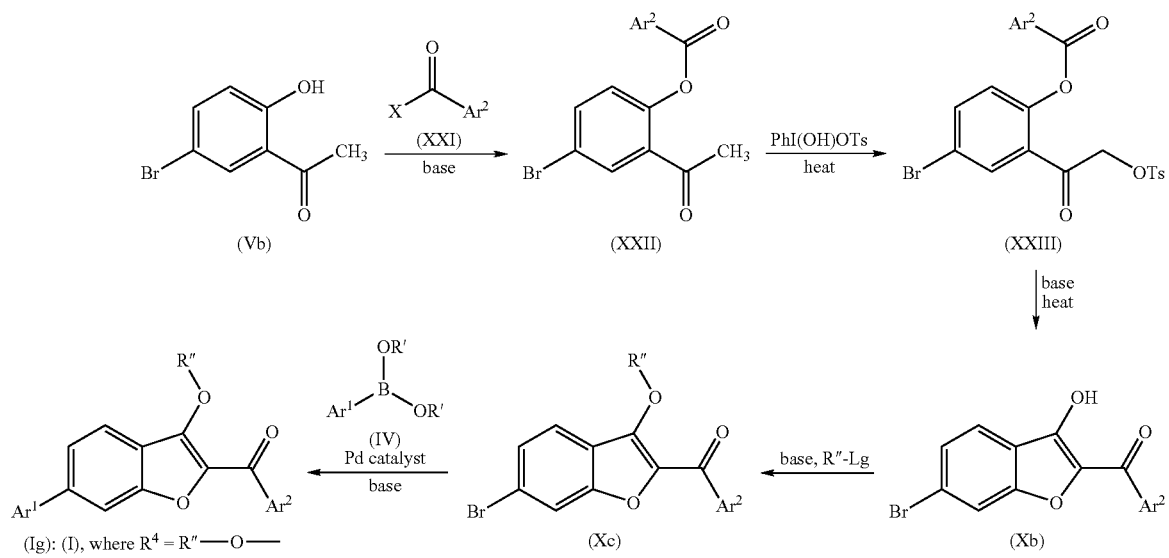

Starting material (Vb) is converted to ester (XXII) via the agency of base and acid chloride (XXI). Alternatively, (Va) could also be treated with an appropriate carboxylic acid and any coupling agent similar, but not limited, to DCC, EDCI, or PyBOP. Ester (XXII) is converted to (XXIII) through application of [hydroxy(tosyloxy)iodo]benzene (Koser's reagent) and heat as described in O m Prakash et al., *Synthesis*, 1992, 629. This publication also describes the methods in which (XXIII) can ultimately be converted to compounds similar to (Xb). Compound (Xb) can be converted to (Xc) in a number of ways including, but not limited to, treatment with an appropriate alkyl halide and base or use of the Mitsunobu coupling protocol. The desired compound, (Ig) can be obtained from (Xc) via Suzuki conditions.

-continued

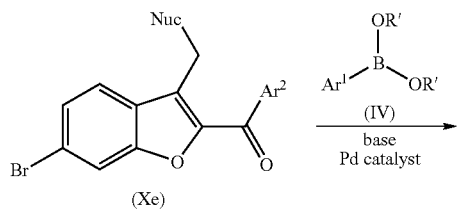

-continued

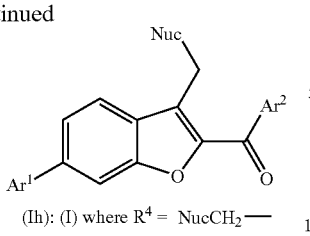

(Ih): (I) where $R^4 = NucCH_2-$

Treatment of compound (Xa) with NBS or other brominating agents in the presence of heat, light and an initiator such as AIBN or benzoyl peroxide, will provide allylic bromide (Xd). The allylic bromide can be displaced by a nucleophile in the presence of a base such as, but not limited to, NaOH or potassium carbonate, to provide (Xe) which will undergo reaction under Suzuki conditions to give (Ih).

An example of a formula (I) compound prepared using the method of Reaction Scheme 10 is described further in Specific Example 177 below.

A further variation of the methods of Reaction Schemes 1 and 2 is depicted in Reaction Scheme 11 below for the preparation of formula (I) compounds where $R^4$ is H.

Reaction Scheme 11

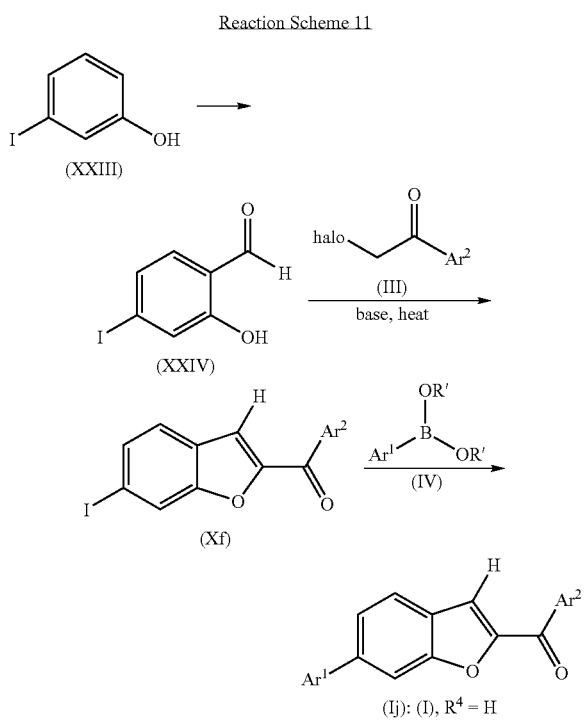

3-Iodophenol (XXIII) can be reacted with paraformaldehyde in the presence of magnesium chloride and triethylamine to afford aldehyde (XXIV). Similarly, one can also employ Vilsmeier type conditions to obtain the desired compound. Subsequent cyclization of (XXIV) with haloarylketone (III) similar to that described earlier in Reaction Scheme 1 will yield iodide (Xf), which can be reacted with a boronic acid or ester (IV) under Suzuki conditions to give the final compound (Ij).

An example of a formula (I) compound prepared using the method of Reaction Scheme 11 is described further in Specific Example 183 below.

A further variation of the methods of Reaction Schemes 1 and 2 is depicted in Reaction Scheme 12 below, suitable for the preparation of formula (I) compounds where $R^4$ is alkyl.

Reaction Scheme 12

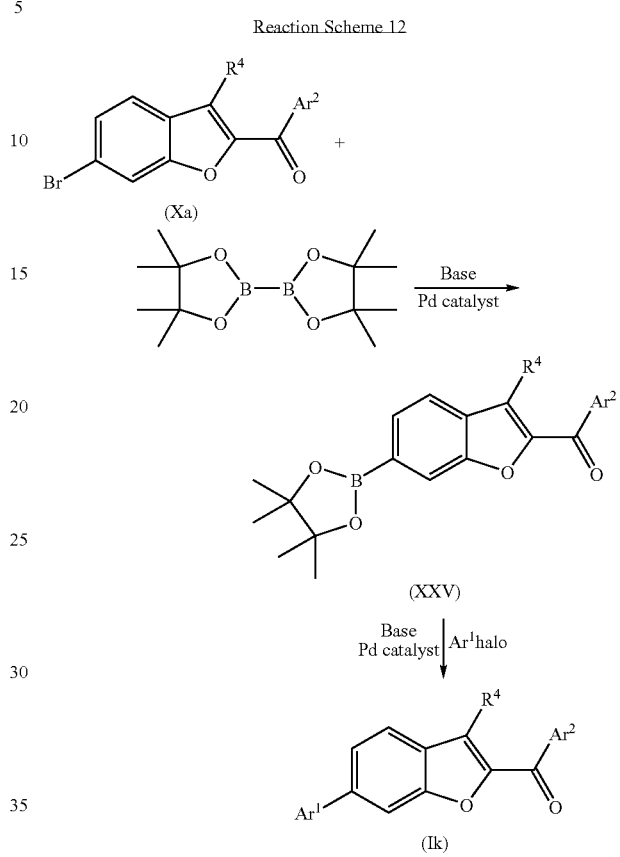

The compound of formula (Xa), prepared by the methods described in Reactions Scheme 1 or 6 above, can be treated with bis(pinacolato)diboron in the presence of base and an appropriate palladium catalyst to provide the aryl borane of formula (XXV). Alternatively, the formula (Xa) compound may be converted to an organometallic compound by halogen-metal exchange, for example with an alkyl lithium reagent, then subsequently treated with a reagent such as bis(pihacolato)diboron to generate the boronic ester of formula (XXV). The formula (XXV) compound thus obtained can be treated under standard Suzuki conditions to give the compound of formula (1 k).

An example of a formula (I) compound prepared using the method of Reaction Scheme 12 is described further in Specific Example 186 below.

One skilled in the art would recognize that sensitive or reactive substituents attached to starting materials or intermediate compounds may need to be protected and deprotected during the synthetic routes described above. Protecting groups in general may be added and removed by conventional methods well known in the art [see, e.g., T. W. Greene and P. G. M. Wuts, *Protective Groups in Organic Synthesis*; Wiley: New York, (1999)].

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The purification of isomers and the separation of isomeric mixtures of a compound of formula (I) may be accomplished by standard techniques known in the art.

The following examples are provided to further illustrate the compounds of the invention and their preparation, but should not be construed to be limiting in any way.

Thus, in another embodiment, the present invention provides a process for preparing the compounds of the formula (I), wherein a compound of formula (X)

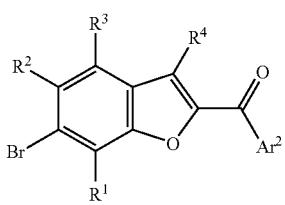
(X)

wherein $R^1$ to $R^4$ and $Ar^2$ have the meaning indicated in claim 1, is reacted with a compound (IV)

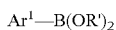 (IV), wherein $Ar^1$ has the meaning indicated in claim 1, and where R' is selected in each instance independently from H and $(C_1\text{-}C_3)$alkyl, or (IV) represents

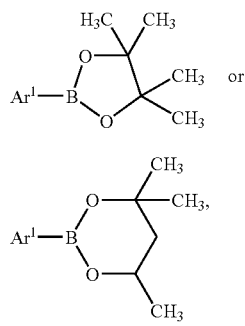
(IVa)
or
(IVb)

in the presence of a palladium catalyst and base; or a compound of formula (XVII)

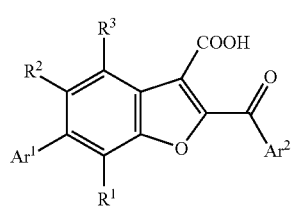
(XVII)

wherein $R^1$ to $R^4$ and $Ar^1$ and $Ar^2$ have the meaning indicated in claim 1, is reacted with a compound of formula

 $R^5NH_2$ wherein $R^5$ has the meaning indicated in claim 1, in the presence of EDC and HOBt, to give a compound of formula (Ia)

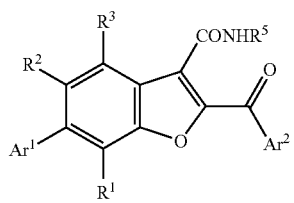
(Ia)

wherein $R^1$ to $R^5$ and $Ar^1$ and $Ar^2$ have the meaning indicated in claim 1; or a compound of formula (Ia)

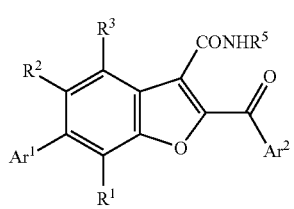
(Ia)

wherein $R^1$ to $R^3$ and $Ar^1$ and $Ar^2$ have the meaning indicated in claim 1 and $R^5$ means hydrogen, is reacted with thionyl chloride to give a compound of formula (Ib)

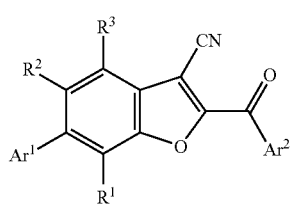
(Ib)

wherein $R^1$ to $R^3$ and $Ar^1$ and $Ar^2$ have the meaning indicated in claim 1.

SPECIFIC EXAMPLES

General Analytical Procedures

Proton ($^1$H) nuclear magnetic resonance (NMR) spectra were measured with a General Electric GN-Omega 300 (300 MHz) spectrometer with either $Me_4Si$ (δ 0.00) or residual protonated solvent ($CHCl_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent ($CDCl_3$ δ 77.0; $d_3$-MeOD; δ 49.0; $d_6$-DMSO δ 39.5) as standard.

Chiral separations were performed using a commercially available Chiracel® AD HPLC column, eluting with a gradient of isopropanol in hexane (from 1% to 15%) with addition of 0.1% trifluoroacetic acid.

HPLC-electrospray mass spectra (HPLC ES-MS) data listed in Tables 1 was obtained using a Hewlett-Packard 1100 HPLC equipped with a quaternary pump, a variable wavelength detector set at 254 nm, a YMC pro C-18 column (2×23 mm, 120A), and a Finnigan LCQ ion trap mass spectrometer with electrospray ionization. Spectra were scanned from 120-1200 amu using a variable ion time according to the number of ions in the source. The eluants were A: 0.01% TFA in water with and B: 0.01% TFA in acetonitrile. Gradient elution from 10% B to 95% over 3.5 minutes at a flow rate of 1.0 mL/min was used with an initial hold of 0.5 minutes and a final hold at 95% B of 0.5 minutes. Total run time was 6.5 minutes. All compound structures are consistent with the analytical data presented.

Example 1

Preparation of (2,4-Dichloro-phenyl)-(3-methyl-6-m-tolyl-benzofuran-2-yl)-methanone

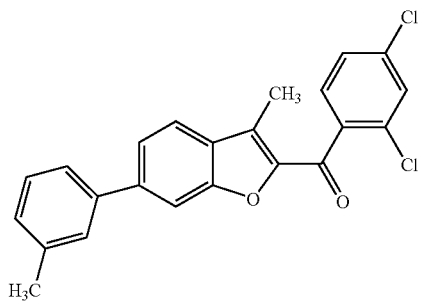

Step 1: Preparation of the Starting Material: 4-Bromo-2-Methoxy-Benzonitrile

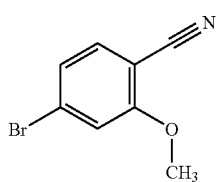

A mixture of 4-bromo-2-fluoro-benzonitrile (15.0 g, 75.0 mmol), methanol (30.4 mL, 350 mmol) and potassium carbonate (31.1 g, 225 mmol) in DMF (150 mL) was stirred under argon at 55° C. overnight. At this point TLC (100% methylene chloride) revealed no starting material, and the reaction mixture was poured into ether (300 mL) and water (150 mL). The layers were separated, and the organic layer was washed with water (150 mL) and brine (50 mL), dried over $Mg_2SO_4$, filtrated, and concentrated under reduced pressure, providing (15.2 g, 95.5%) of 4-bromo-2-methoxy-benzonitrile as a white solid. $^1$H-NMR (CDCl$_3$) δ 7.41 (d, J=8.1 Hz, 1H), 7.16 (dd, J=8.1, 1,6 Hz, 1H), 7.13 (d, J=1.6 Hz, 1H), 3.93 (s, 3H); MS GC-MS (M$^+$=211; RT=6.15 min).

Step 2: Preparation of the Intermediate: 4-Bromo-2-Hydroxy-Benzonitrile

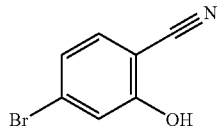

To a stirred solution of 4-bromo-2-methoxy-benzonitrile (4.60 g, 21.7 mmol) in methylene chloride (20 mL) was added aluminum chloride (14.5 g, 108 mmol). After stirring under an argon atmosphere for 10 min, more methylene chloride (30 mL) was added, and the mixture left to reflux under argon overnight. The reaction was then diluted with ethyl acetate, washed with water, brine, and dried over magnesium sulfate. The solvent was removed at reduced pressure, providing (4.09 g, 95.2%) of 4-bromo-2-hydroxy-benzonitrile as a slightly gray-colored product. $^1$H-NMR (CDCl$_3$) δ 7.35 (d, J=8.4 Hz, 1H), 7.19 (d, J=1.4 Hz, 1H), 7.14 (dd, J=8.4, 1,4 Hz, 1H), 6.15 (s, 1H); TLC R$_f$=0.78 (50% ethyl acetate-hexane).

Step 3: Preparation of the Starting Material: 1-(4-Bromo-2-Hydroxy-Phenyl)-Ethanone

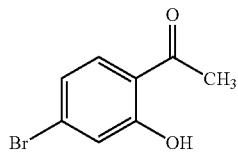

To a stirred solution of 4-Bromo-2-hydroxy-benzonitrile (3.6 g, 18.2 mmol) in anhydrous THF solution (20 mL) was added methylmagnesium bromide (1.4 M in THF/toluene, 39.0 mL, 54.6 mmol, 3 eq) at 0° C. under argon. The reaction mixture was slowly warm up to rt and stirred for 15 h. The mixture was cooled to 0° C. and quenched by the addition of water (5 mL) followed by concentrated HCl (10 mL). The resulting solution was refluxed for 2 h before cooled down to rt. The reaction mixture was then poured into EtOAc (100 mL) and water (100 mL). The layer was separated and the organic layer was washed with water (2×50 mL), dried over Na$_2$SO$_4$, filtrated, and concentrated under reduced pressure. The residue was then subjected to silica gel chromatography (20% EtOAc/Hexane) to provide 1-(4-Bromo-2-hydroxy-phenyl)-ethanone (2.81 g, 71.9%) as yellow oil. $^1$H-NMR (CDCl$_3$): δ 12.32 (s, 1H, OH), 7.57 (d, J=8.7 Hz, 1H), 7.17 (d, J=1.9 Hz, 1H), 7.03 (dd, J=1.9, 8.7 Hz, 1H), 2.62 (s, 3H).

Step 4: Preparation of the intermediate: (6-Bromo-3-methyl-benzofuran-2-yl)(2,4-dichloro-phenyl)methanone

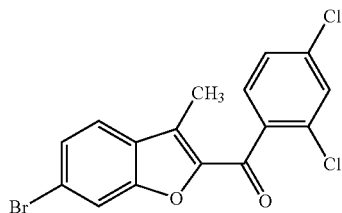

To a stirred solution of 1-(4-Bromo-2-hydroxy-phenyl)-ethanone (2.81 g, 13.1 mmol, from step 1) and 2-chloro-1-(2,4-dichlorophenyl)ethanone (6.88 g, 30.8 mmol, 2.3 eq) in anhydrous N,N-dimethylformamide (50 mL) was added K$_2$CO$_3$ (7.42 g, 53.7 mmol, 4.0 eq). The dark brown reaction mixture was stirred at 90° C. for 38 h. The reaction was poured into ethyl acetate (100 mL) and water (100 mL) after cooled down to rt. Extracted with ethyl acetate (3×50 mL). The organic layer was dried (Na$_2$SO$_4$), filtered, and evaporated in vacuo. The crude product was washed by hexane (2×30 mL) followed by ethyl ether (2×30 mL) to provide 2.22 g (44%) of the desired compound as light yellow solid. $^1$H-NMR (CDCl$_3$) δ 7.64 (d, J=1.9 Hz, 1H), 7.54 (d, J=8.7 Hz, 1H), 7.49 (d, J=1.9 Hz, 1H), 7.45-7.36 (m, 3H), 2.57 (s, 3H); MS LC-MS (MH$^+$=385).

Step 5: Preparation of (2,4-Dichloro-phenyl)(3-methyl-6-m-tolyl-benzofuran-2-yl)methanone

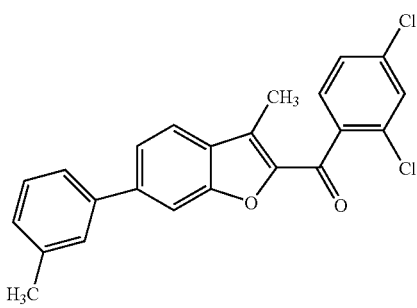

A solution of (6-Bromo-3-methyl-benzofuran-2-yl)-(2,4-dichloro-phenyl)-methanone (50 mg, 0.13 mmol) in toluene (1.5 mL) and ethanol (1.5 mL) was degassed with argon for 15 min. At this time, 3-methyl benzene boronic acid (21.2 mg, 0.16 mmol, 1.2 eq) was added followed by [1,1'-bis(diphenylphosphino)-ferrocene]dichloro-palladium(II), complex with dichloromethane (1:1) (10.6 mg, 0.01 mmol, 0.1 eq) and 2M aqueous Na$_2$CO$_3$ (0.21 mL, 3 eq). The reaction was bubbled with argon for another 5 min and then heated to 85° C. for 4 h. The reaction was diluted with ethyl acetate, washed with water, brine, and dried over sodium sulfate. The solvent was removed at reduced pressure and purified on the pre-HPLC to afford 35.6 mg (69%) of a yellow solid as the product. $^1$H-NMR (CDCl$_3$): δ 7.72 (d, J=8.0 Hz, 1H), 7.65 (s, 1H), 7.57 (dd, J=1.6, 8.0 Hz, 1H), 7.50 (d, J=1.9 Hz, 1H), 7.58 to 7.53 (m, 4H), 7.33 (t, 1H), 7.18 (d, J=7.2 Hz, 1H), 2.56 (s, 3H), 2.42 (s, 3H); LC-MS (MH$^+$=395/397).

Using the method of Example 1 and the appropriate starting materials and reagents, compound Examples 4-39 of Table 1 were similarly prepared.

Example 2

Preparation of 6-(3-Cyano-phenyl)-2-(2,4-dichloro-benzoyl)-benzofuran-3-carbonitrile

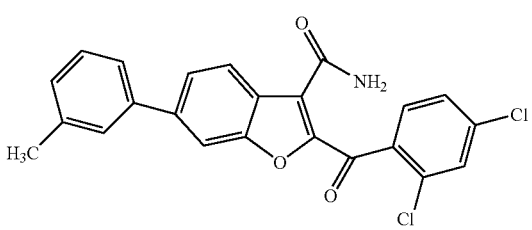

Step 1: Preparation of (2,4-Dihydroxy-phenyl)-oxo-acetic acid ethyl ester

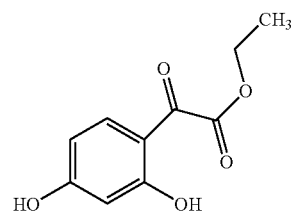

To a solution of resorcinol (5.0 g, 45.4 mmol, 1 eq) in diethyl ether (30 mL) was added 3M EtMgBr (18.5 mL, 50.0 mmol, 1.1 eq)) dropwise under argon. The reaction mixture was stirred at rt for 20 min. The ether was removed under vacuum and anhydrous toluene (80 mL) was added. A solution of oxalyl chloride (4.36 mL, 50 mmol, 1.1 eq) in toluene (20 mL) was added to the mixture dropwise under argon. The reaction mixture was stirred at rt for 15 h. Anhydrous ethanol (40 mL) was added to the mixture and the reaction mixture was stirred at rt for 1 h. Most of the solvent was evaporated and then EtOAc (60 mL) and water (40 mL) were added to the mixture. The layer was separated and the organic layer was washed with water (2×40 mL), dried over Na$_2$SO$_4$, filtrated, and concentrated under reduced pressure. The residue was purified by column chromatography eluted with 20% EtOAc/hexane then 50% EtOAc/hexane solution to afford white solid (5.88 g, 62%) as product. $^1$H-NMR (CD$_3$CN): δ 7.62 (d, J=9.0 Hz, 1H), 6.50 (dd, J=2.3, 9.0 Hz, 1H), 6.41 (d. J=2.3 Hz, 1H), 4.44 (q, 2H), 1.40 (t, 3H).

Step 2: Preparation of [4-(tert-Butyl-dimethyl-silanyloxy)-2-hydroxy-phenyl]-oxo-acetic acid ethyl ester

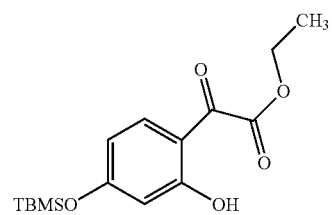

To a solution of (2,4-Dihydroxy-phenyl)-oxo-acetic acid ethyl ester (from step 1, 2.71 g, 12.9 mmol, 1 eq) in anhydrous DCM (40 mL) solution was added triethylamine (1.97 mL, 14.2 mmol, 1.1 eq), followed by addition of tert-butyldimethylchlorosilane (1.89 g, 14.2 mmol, 1.1 eq)/DCM (10 mL) solution dropwise at 0° C. under argon. The reaction mixture was stirred at 0° C. for 5 min. Water (30 mL) was added to the reaction mixture to quench the reaction. The organic layer was washed with water (2×30 mL), dried over Na$_2$SO$_4$, filtrated, and concentrated under reduced pressure to afford a light yellow solid (4.1 g, contains 40% mono-substituted product) as crude product. This material was used in step 3 without further purification.

Step 3: Preparation of 2-(2,4-Dichloro-benzoyl)-hydroxy-benzofuran-3-carboxylic acid ethyl ester

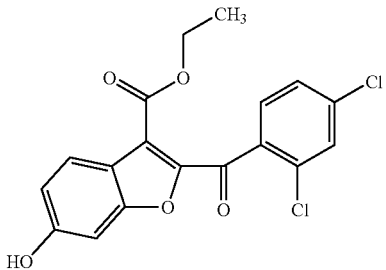

To a solution of [4-(tert-Butyl-dimethyl-silanyloxy)-2-hydroxy-phenyl]-oxo-acetic acid ethyl ester from step 2 (2.0 g, 6.16 mmol) and 2-chloro-1-(2,4-dichlorophenyl)ethanone (1.65 g, 7.4 mmol, 1.2 eq) in anhydrous N,N-dimethylformamide (100 mL) was added potassium carbonate (1.7 g, 12.3 mmol, 2 eq). The reaction mixture was stirred at 90° C. for 16 h. The mixture was cooled to room temperature then poured into ethyl acetate (100 mL) and water (100 mL). The aqueous layer was extracted with ethyl acetate (2×100 mL). Combined the organic layer was washed by water (2×100 mL), dried over $Na_2SO_4$, filtrated, and evaporated in vacuo. The residue was purified by column chromatography eluted with 20% EtOAc/hexane then 50% EtOAc/hexane solution to afford an yellow solid (843 mg, 36%) as product. $^1$H-NMR ($CD_3CN$): δ 7.79 (d, J=8.0 Hz, 1H), 7.64 (d, 1.9 Hz, 1H), 7.59 (d, J=8.0 Hz, 1H), 7.47 (dd, J=2.3, 8.3 Hz, 1H), 7.06 (d, J=2.3 Hz, 1H), 7.0 (dd, J=2.3, 8.0 Hz, 1H), 4.11 (q, 2H), 1.21 (t, 3H); LC-MS ($MH^+$=3791381).

Step 4: Preparation of 2-(2,4-Dichloro-benzoyl)-6-trifluoromethanesulfonyloxy-benzofuran-3-carboxylic acid ethyl ester

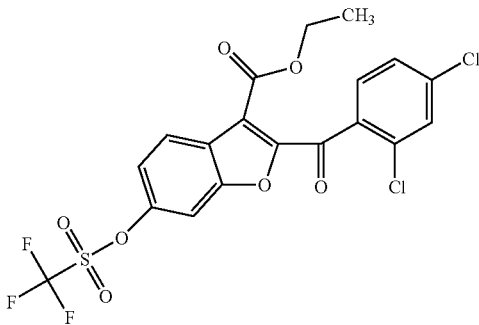

To a solution of 2-(2,4-Dichloro-benzoyl)-6-hydroxy-benzofuran-3-carboxylic acid ethyl ester from step 3 (460 mg, 1.21 mmol, 1 eq) in anhydrous DCM (10 mL) solution was added triethylamine (0.51 mL, 3.64 mmol, 3 eq), followed by trifluoromethanesulfonic anhydride (0.24 mL, 1.46 mmol, 1.2 eq) at 0° C. under argon. The reaction mixture was stirred at 0° C. for 15 min. The reaction solution was concentrated under reduced pressure. The residue was purified by quick flash column chromatography eluted with 20% EtOAc/hexane to afford an dark yellow oil as product (510 mg, 82%) as product. $^1$H-NMR ($CD_3CN$): δ 8.15 (d, J=8.7 Hz, 1H), 7.79 (d, J=2.3 Hz, 1H), 7.66 (d, J=8.7 Hz, 1H), 7.63 (d, J=2.0 Hz, 1H), 7.50-7.46 (m, 2H), 4.17 (q, 2H), 1.20 (t, 3H).

Step 5: Preparation of 2-(2,4-Dichloro-benzoyl)-6-m-tolyl-benzofuran-3-carboxylic acid ethyl ester

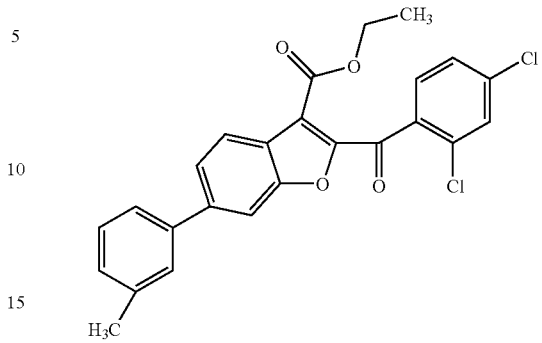

To a solution of 2-(2,4-Dichloro-benzoyl)-6-trifluoromethanesulfonyloxy-benzofuran-3-carboxylic acid ethyl ester from step 4 (162 mg, 0.32 mmol, 1 eq) in anhydrous N,N-dimethylformamide (2 mL) were sequential added 3-methyl benzene boronic acid (64.6 mg, 0.63 mmol, 1.5 eq), potassium carbonate (87.6 mg, 0.63 mmol, 2 eq) and tetrakis (triphenylphosphine)palladium(0) (73.2 mg, 0.06 mmol, 0.2 eq) under argon. The reaction mixture was degassed for 5 min. The reaction was then stirred at 80° C. for 4 h followed by stirred at rt for 12 h. The mixture was cooled to room temperature then poured into ethyl acetate (10 mL) and water (10 mL). The aqueous layer was extracted with ethyl acetate (2×10 mL). Combined the organic layer was washed by water (2×10 mL), dried over $Na_2SO_4$, filtrated, and evaporated In vacuo. The residue was purified by pre-HPLC to afford an yellow solid (91.3 mg, 63%) as product. $^1$H-NMR ($CDCl_3$): δ 8.04 (d, J=8.3 Hz, 1H), 7.73 (s, 1H), 7.64 (dd, J=1.5, 8.3 Hz, 1H), 7.57 (d, J=8.3 Hz, 1H), 7.47 (d, J=1.9 Hz, 1H), 7.41 (m, 2H), 7.36 (dd, J=1.9, 8.3 Hz, 1H), 7.34 (t, 1H), 7.19 (d, J=8.3 Hz, 1H), 4.245 (q, 2H), 2.43 (s, 3H), 1.28 (t, 3H); LC-MS ($MH^+$=453/455).

Step 6: Preparation of 2-(2,4-Dichloro-benzoyl)-6-m-tolyl-benzofuran-3-carboxylic acid

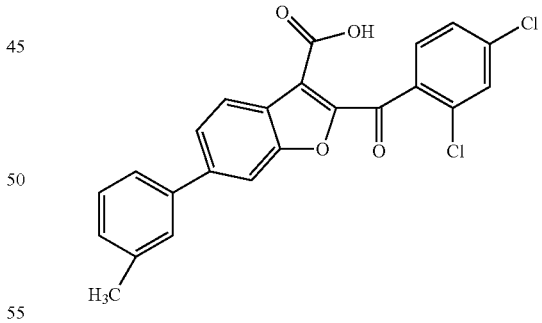

To a solution of 2-(2,4-Dichloro-benzoyl)-6-m-tolyl-benzofuran-3-carboxylic acid ethyl ester from step 5 (91.3 mg, 0.20 mmol, 1 eq) in MeOH/$H_2O$/THF (2 mL, ratio:1:1:1) solution was added potassium hydroxide (72.0 mg, 0.52 mmol, 2.6 eq). The reaction mixture was stirred at rt for 6 h. 2N HCl (500 uL) was added to the reaction mixture and the solvent was removed under reduced pressure. The residue was purified by pre-HPLC to afford an yellow solid (68 mg, 80%) as desired product. $^1$H-NMR ($CDCl_3$): δ 8.58 (d, J=8.3 Hz, 1H), 7.75 (dd, J=1.5, 8.3 Hz, 1H), 7.69 (s, 1H), 7.57 (d, J=1.5 Hz, 1H), 7.56 (d, J=8.3 Hz, 1H), 7.46 (dd, J=1.5, 8.3 Hz, 1H), 7.43 (m, 2H), 7.34 (t, 1H), 7.21 (d, J=8.3 Hz, 1H), 2.43 (s, 3H); LC-MS (MH⁺=425/427).

Step 7: Preparation of 2-(2,4-Dichloro-benzol)-6-m-tolyl-benzofuran-3-carboxylic acid amide

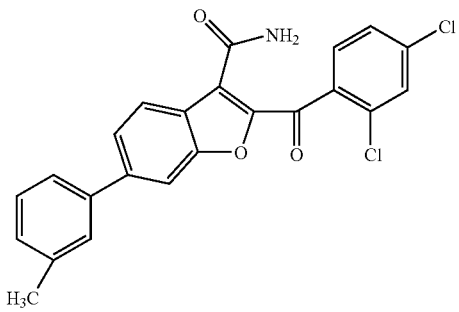

To a solution of 2-(2,4-Dichloro-benzoyl)-6-m-tolyl-benzofuran-3-carboxylic acid from step 6 (61.2 mg, 0.14 mmol, 1 eq) in anhydrous THF (3 mL) solution were added EDC (60.0 mg, 0.31 mmol, 2.2 eq) and HOBt (50.0 mg, 0.37 mmol, 2.6 eq). The reaction mixture was stirred at rt for 1 h. A 30% aq. NH₄OH solution (0.5 mL) was added to the reaction mixture and stirring was continued for 15 h. The reaction mixture was poured into EtOAc (10 mL). The organic layer were washed with 1N NaOH (5 mL), 1N HCl (5 mL), brine (5 mL). The organic layer was dried over Na₂SO₄, filtrated, and evaporated in vacuo. The residue was purified by pre-TLC (10% Acetone/DCM) to afford an yellow solid (46.2 mg, 78%) as product. ¹H-NMR (CDCl₃): δ 9.39 (broad, NH, 1H), 8.58 (d, J=8.3 Hz, 1H), 7.68 (dd, J=1.5, 8.3 Hz, 1H), 7.63 (8, 1H), 7.51 (d, J=1.5 Hz, 1H), 7.48 (d, J=8.3 Hz, 1H), 7.43-7.40 (m, 3H), 7.32 (t, 1H), 7.18 (d, J=8.3 Hz, 1H), 6.01 (broad, NH, 1H), 2.42 (s, 3H); LC-MS (MH⁺=424/426).

Using the method described for Example 2 and the appropriate starting materials, Table 1 Examples 40-43 were similarly prepared.

Example 3

Preparation of 2-(2,4-Dichloro-benzoyl-6-m-tolyl-benzofuran-3-carbonitrile

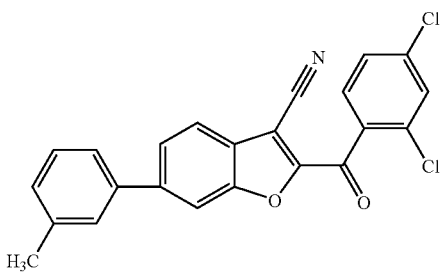

A mixture of 2-(2,4-Dichloro-benzoyl)-6-m-tolyl-benzofuran-3-carboxylic acid amide from Example 2 step 7 (46.2 mg, 0.11 mmol) and SOCl₂ (3 mL) was heated at 80° C. for 15 h. The reaction was cooled down to rt and the solvent was removed under reduced pressure. The residue was purified by pre-HPLC to afford a yellow solid (5.9 mg, 13%) as product. ¹H-NMR (CDCl₃): δ 7.88 (d, J=8.3 Hz, 1H), 7.79 (s, 1H), 7.73 (dd, J=1.5, 8.3 Hz, 1H), 7.54 (d, J=1.5 Hz, 1H), 7.52 (d, J=8.3 Hz, 1H), 7.4 (dd, J=1.5, 8.3 Hz, 1H), 7.41 (m, 2H), 7.36 (t, 1H), 7.23 (d, J=8.3 Hz, 1H), 2.42 (s, 3H); LC-MS (MH⁺=406/408).

Using the method of Example 3 and the appropriate starting materials and reagents, compound Examples 44-46 of Table 1 were similarly prepared.

Example 170

Preparation of N-[3-(2-(2,4-dichlorobenzoyl)-3-{[(2-methoxyethyl)amino]methyl}-1-benzofuran-6-yl)benzyl]methanesulfonamide trifluoroacetate

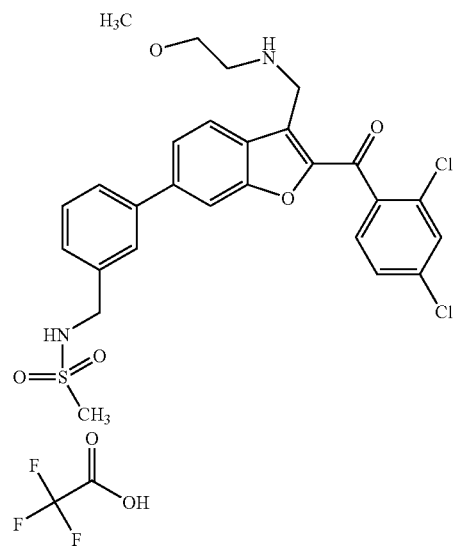

The compound (TFA salt) was prepared as described in Example 171, Step 3. ¹H-NMR (acetone): δ 8.21 (d, 1H), 7.92 (s, 1H), 7.87 (s, 1H), 7.84 (s, 1H), 7.81 (s, 1H), 7.76 (m, 2H), 7.65 (dd, 1H), 7.51 (m, 2H), 6.62 (br, 1H), 4.96 (s, 2H), 4.41 (d, 2H), 3.81 (t, 2H), 3.54 (t, 2H), 3.39 (s, 3H), 2.94 (s, 3H). LC-MS RT=2.66 min; [M+H]⁺=561.5.

Example 171

Preparation of N-[3-(2-(2,4-dichlorobenzoyl-3-{[(2-methoxyethyl)amino]methyl}-1-benzofuran-6-yl)phenyl]methanesulfonamide

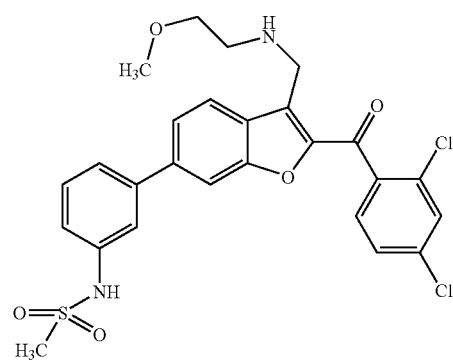

Step 1. Preparation of (6-Bromo-3-bromomethyl-benzofuran-2-yl)-(2,4-dichlorophenyl)-methanone

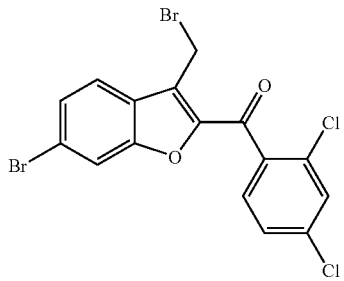

To a stirred solution of (6-Bromo-3-methyl-benzofuran-2-yl)-(2,4-dichloro-phenyl)-methanone (4.0 g, 10.4 mmol) in carbon tetrachloride (40 mL) was added 2,2'-azobisisobutyronitrile (AIBN) (171 mg, 1.04 mmol) and N-bromosuccinimide (1.95 g, 10.9 mmol). The reaction mixture was heated at reflux for 6 h, and upon cooling to rt, the resulting precipitate was removed by filtration and the filtrate was concentrated. The crude residue was purified by column chromatography (10% ethyl acetate in hexanes) to afford the desired product (3.30 g, 65% yield) as a white solid. Rf=0.68 (10% EtOAc in hexanes). $^1$H-NMR (acetone): δ 7.98 (d, 1H), 7.91 (s, 1H), 7.74 (m, 2H), 7.64 (td, 2H), 5.16 (s, 2H).

Step 2. Preparation of {6-Bromo-3-[(2-methoxy-ethylamino)methyl]-benzofuran-2yl}(2,4-dichlorophenyl)-methanone

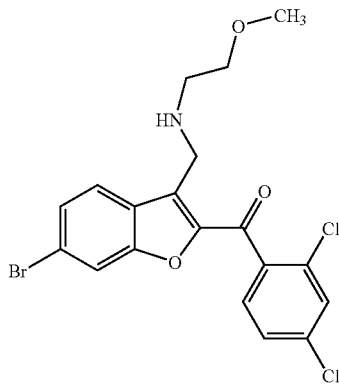

To a solution of 2-methoxyethylamine (118 mg, 1.57 mmol) in THF (6 mL) at 0° C. was added potassium carbonate followed by slow addition of (6-bromo-3-bromomethyl-benzofuran-2-yl)-(2,4-dichlorophenyl)-methanone (660 mg, 1.43 mmol) in several portions. The reaction mixture was stirred at rt for 2 h, and the resulting precipitate was removed by filtration and the filtrate was concentrated. The crude residue was purified by column chromatography (30-50% ethyl acetate in hexanes) giving the desired product (315 mg, 44% yield) as a light yellow viscous oil. $^1$H-NMR (acetone): δ 8.05 (d, 1H), 7.78 (d, 1H), 7.66 (m, 2H), 7.56 (dd, 1H), 7.50 (dd, 1H), 4.25 (s, 2H), 3.41 (t, 2H), 3.25 (s, 3H), 2.74 (t, 2H). LC-MS RT=2.71 min; [M+H]$^+$=456.0.

Step 3. Preparation of N-[3-(2-(2,4-dichlorobenzoyl)-3-{[(2-methoxyethyl)amino]methyl}-1-benzofuran-6-yl)phenyl]methanesulfonamide

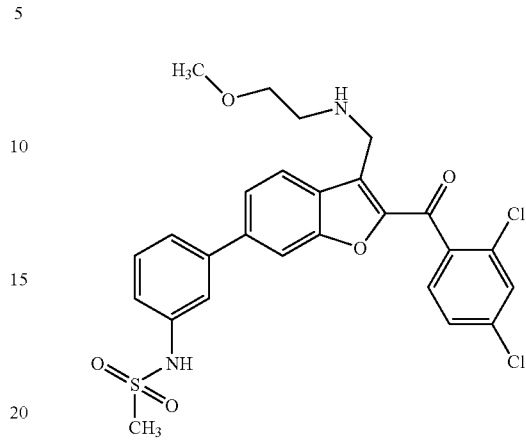

A solution of {6-bromo-3-[(2-methoxy-ethylamino)-methyl]-benzofuran-2-yl}-(2,4-dichlorophenyl)-methanone (110 mg, 0.24 mmol) in toluene (2 mL) and ethanol (2 mL) was degassed with nitrogen for 15 min. At this time, [(3-methylsulfonylamino)phenyl]-boronic acid (62 mg, 0.29 mmol) was added followed by [1,1'-bis(diphenylphosphino)-ferrocene]dichloro-palladium(II), complex with dichloromethane (1:1) (20 mg, 0.02 mmol) and 2M aqueous Na$_2$CO$_3$ (0.64 mL, 5 eq). The reaction was bubbled with nitrogen for another 5 min and then heated at 80° C. for 6 h. Upon cooling to rt, the reaction mixture was filtered and the filtrate was concentrated, and then purified by HPLC to afford the desired product (31 mg, 22% yield) as a solid. $^1$H-NMR (acetone): δ 8.21 (d, 1H), 7.80 (s, 1H), 7.74-7.67 (m, 4H), 7.63-7.46 (m, 4H), 7.37 (dt, 11H), 4.30 (s, 2H), 3.46 (t, 2H), 3.26 (s, 3H), 3.06 (s, 3H), 2.78 (t, 2H). LC-MS RT=2.73 min; [M+H]$^+$=547.1.

Example 172

Preparation of N-[3-(2-(2,4-dichlorobenzoyl)-3-{[(2-methoxyethyl)(methyl)amino]methyl}-1-benzofuran-6-yl)phenyl]methanesulfonamide

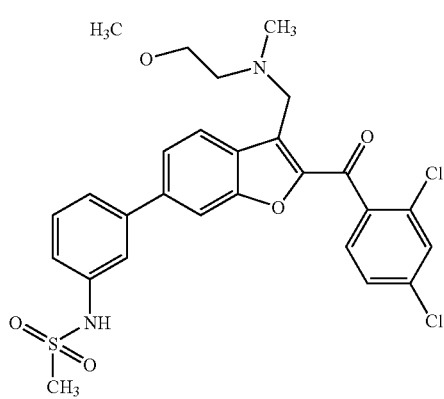

Step 1. Preparation of (6-promo-3-{[(2-methoxy-ethyl)(methyl)amino]methyl}-benzofuran-2yl)-(2,4-dichlorophenyl)methanone

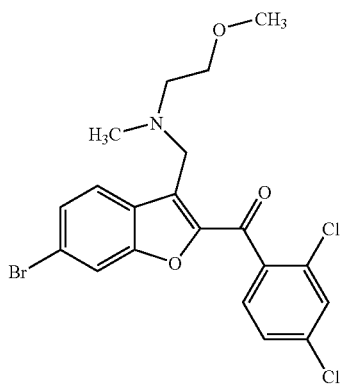

The compound was prepared as described in Example 171, Step 2. $^1$H-NMR (acetone): δ 8.00 (d, 1H), 7.60 (s, 1H), 7.44-7.34 (m, 4H), 4.10 (s, 2H), 3.56 (t, 2H), 3.34 (s, 3H), 2.70 (t, 2H), 2.30 (s, 3H). LC-MS RT=2.65 min; [M+H]$^+$= 470.3

Step 2. Preparation of N-[3-(2-(2,4-dichlorobenzoyl)-3-{[(2-methoxyethyl)(methyl)amino]methyl)}-1-benzofuran-6-yl)phenyl]methanesulfonamide

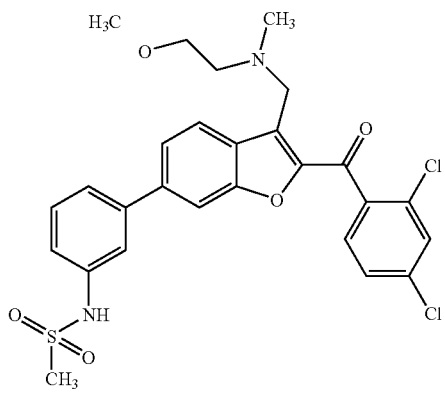

The compound was prepared as described in Example 171, Step 3. $^1$H-NMR (acetone): δ 8.69 (br, 1H), 8.24 (d, 1H), 7.77 (d, 1H), 7.73 (t, 1H), 7.70-7.46 (m, 6H), 7.38 (m, 1H), 4.11 (s, 2H), 3.57 (t, 2H), 3.30 (s, 3H), 3.08 (s, 3H), 2.69 (t, 2H), 2.29 (s, 3H). LC-MS RT=2.63 min; [M+H]$^+$=561.6.

Example 173

Preparation of N-[3-(2-(2,4-dichlorobenzoyl)-3-{[(2-hydroxyethyl)(methyl)amino]methyl}-1-benzofuran-6-yl)benzyl]methanesulfonamide

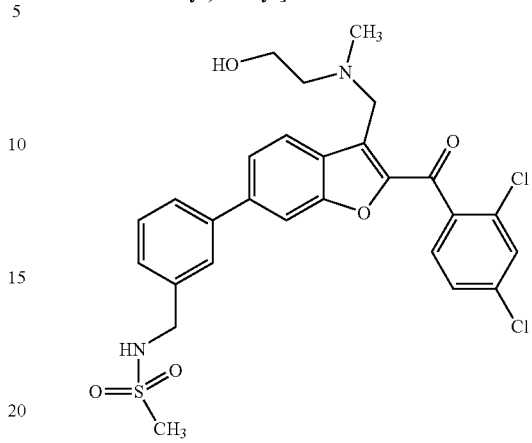

Step 1. Preparation of (6-Bromo-3-{[(2-hydoxy-ethyl)(methyl)amino]methyl}-benzofuran-2yl)-(2,4-dichlorophenyl)-methanone

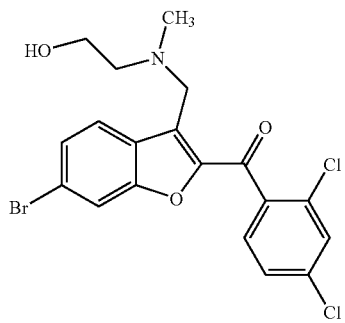

The compound was prepared as described in Example 171, Step 2. $^1$H-NMR (acetone): δ 8.10 (d, 1H), 7.76 (d, 1H), 7.66 (d, 1H), 7.64 (d, 1H), 7.56 (dd, 1H), 7.47 (dd, 1H), 4.08 (s, 2H), 3.68 (t, 2H), 3.53 (br, 1H), 2.62 (t, 2H), 2.26 (s, 3H). LC-MS RT=2.48 min; [M+H]$^+$=456.3.

Step 2. Preparation of N-[3-(2-(2,4-dichlorobenzoyl)-3-{[(2-hydroxyethyl)(methyl)amino]methyl}-benzofuran-6-yl)benzyl]methanesulfonamide

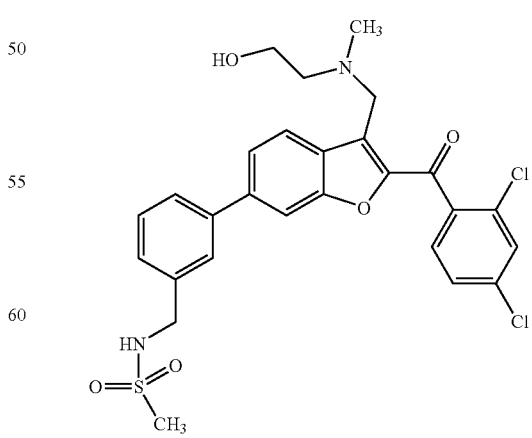

The compound was prepared as described in Example 171, Step 3. $^1$H-NMR (acetone): δ 8.22 (d, 1H), 7.83 (d, 2H), 7.71

(m, 4H), 7.60 (dd, 1H), 7.48 (m, 2H), 6.61 (br, 1H), 4.40 (d, 2H), 4.13 (s, 2H), 3.70 (t, 2H), 2.90 (s, 3H), 2.65 (t, 2H), 2.30 (s, 3H). LC-MS RT=2.59 min; [M+H]$^+$=561.0.

Example 174

Preparation of N-[3-(2-(2,4-dichlorobenzoyl)-3-{[(2-hydroxyethyl)(methyl)amino]methyl}-1-benzofuran-6-yl)phenyl]methanesulfonamide

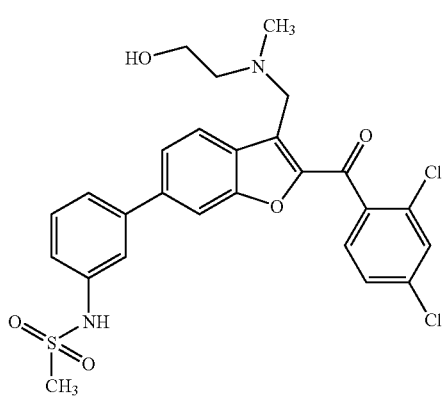

The compound was prepared as described in Example 173, Step 2. $^1$H-NMR (acetone): δ 8.25 (d, 1H), 7.78 (s, 1H), 7.73-7.48 (m, 8H), 7.39 (dt, 1H), 4.13 (s, 2H), 3.70 (t, 2H), 3.06 (s, 3H), 2.65 (t, 2H), 2.30 (s, 3H). LC-MS RT=2.59 min; [M+H]$^+$=547.0.

Example 175

Preparation of N-[3-(2-(2,4-dichlorobenzoyl)-3-{[(2-methoxyethyl)(propyl)amino]methyl}-1-benzofuran-6-yl)phenyl]methanesulfonamide

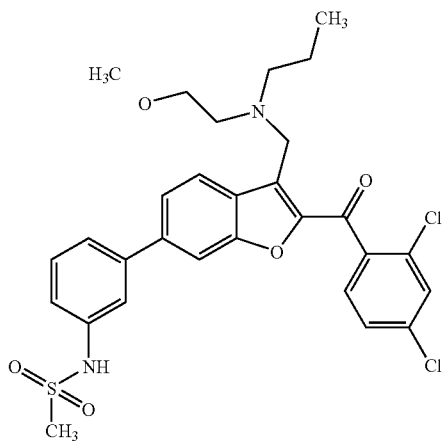

Step 1. Preparation of (6-Bromo-3-{[(2-methoxyethyl)(propyl)amino]methyl}-benzofuran-2yl)(2,4-dichlorophenyl)methanone

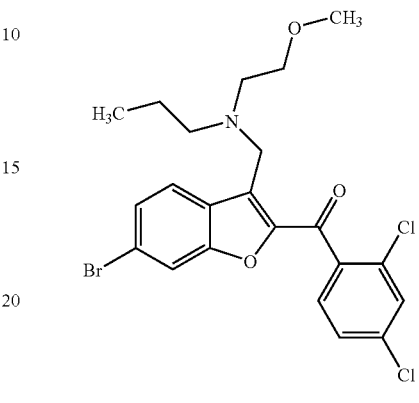

The compound was prepared as described in Example 171 Step 2. $^1$H-NMR (acetone): δ 8.18 (d, 1H), 7.75 (d 1H), 7.65 (m, 2H), 7.58 (dd, 1H), 7.49 (dd, 1H), 4.17 (s, 2H), 3.51 (t, 2H), 3.26 (s, 3H), 2.70 (t, 2H), 2.46 (t, 2H), 1.46 (m, 2H), 0.77 (t, 3H). LC-MS RT=3.22 min; [M+H]$^+$=498.0.

Step 2. Preparation of N-[3-(2-(2,4-dichlorobenzoyl)-3-{[(2-methoxyethyl)(propyl)amino]methyl}-1-benzofuran-6-yl)phenyl]methanesulfonamide

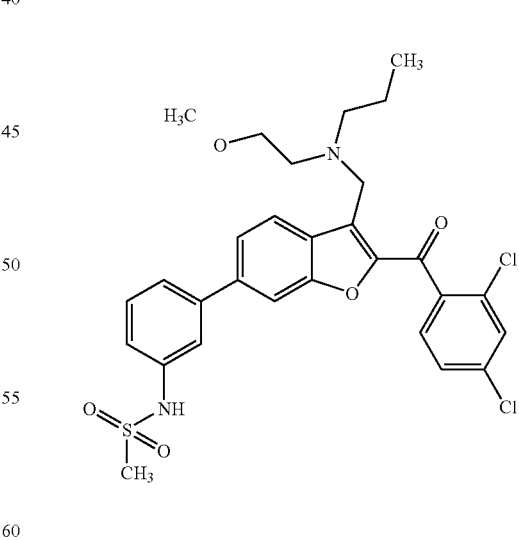

The compound was prepared as described in Example 171, Step 3. $^1$H-NMR (acetone): δ 8.28 (d, 1H), 7.77 (d, 1H), 7.74 (t, 1H), 7.70-7.45 (m, 7H), 7.38 (m, 1H), 4.21 (s, 2H), 3.52 (t, 2H), 3.27 (s, 3H), 3.06 (s, 3H), 2.74 (t, 2H), 2.50 (t, 2H), 1.50 (m, 2H, 0.80 (t, 3H). LCMS RT=2.86 min; [M+H]$^+$=589.0.

Example 176

Preparation of N-{3-[2-(2,4-Dichloro-benzoyl)-3-trifluoromethyl-benzofuran-6-yl]-phenyl}-acetamide

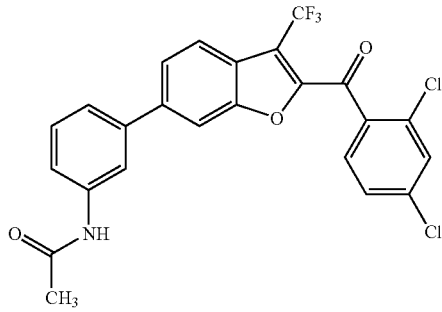

Step 1: Preparation of (2,4-Dichloro-phenyl)-(6-hydroxy-3-trifluoromethyl-benzofuran-2-yl)-methanone

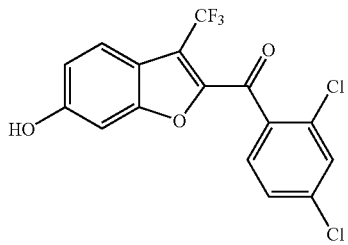

To a solution of 1-(2,4-dihydroxy-phenyl)-2,2,2-trifluoro-ethanone (1.00 g, 4.85 mmol) and 2-chloro-1-(2,4-dichlorophenyl)ethanone (1.08 g, 4.85 mmol, 1.0 eq) in anhydrous N,N-dimethylformamide (10 mL) was added potassium carbonate (1.01 g, 7.28 mmol, 1.5 eq). The reaction mixture was stirred at 90° C. for 16 h. The mixture was cooled to room temperature and then poured into ethyl acetate (100 mL) and water (100 mL). The aqueous layer was extracted with ethyl acetate (2×100 mL). The combined organic layers were washed with water (2×100 mL), dried over Na$_2$SO$_4$, filtrated, and evaporated in vacuo. The residue was purified by column chromatography eluted with 5% EtOAc/hexane then 30% EtOAc/hexane solution to afford a yellow solid (610 mg, 33.5%) as product. $^1$H-NMR (CDCl$_3$): δ 7.76 (d, J=8.7 Hz, 1H), 7.52 (d, J=8.5 Hz, 1H), 7.50 (d, J=1.7 Hz, 1H), 7.41 (dd, J=8.1, 1.9 Hz, 1H), 7.01 to 6.95 (m, 2H), 5.49 (s, 1H); LC-MS (MH$^+$=375/377).

Step 2: Preparation of Trifluoro-methanesulfonic acid 2-(2,4-dichloro-benzoyl)-3-trifluoromethyl-benzofuran-6-yl ester

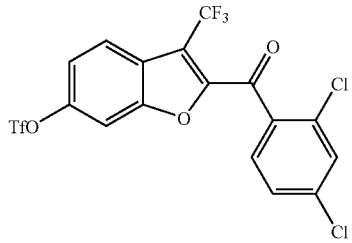

To a solution of (2,4-Dichloro-phenyl)-(6-hydroxy-3-trifluoromethyl-benzofuran-2-yl)-methanone from step 1 (500 mg, 1.33 mmol) in anhydrous DCM (2.5 mL) solution was added pyridine (0.540 mL, 6.66 mmol, 5 eq), followed by trifluoromethanesulfonic anhydride (0.271 mL, 1.60 mmol, 1.2 eq) at 0° C. under argon. The reaction mixture was is stirred at 0° C. for 4 h. The reaction solution was concentrated under reduced pressure and the residue was purified by flash column chromatography (5% EtOAc/hexane) to afford a light yellow oil (610 mg, 90%) as product. $^1$H-NMR (CDCl$_3$): δ 7.99 (d, J=9.1 Hz, 1H), 7.57 (d, J=5.3 Hz, 1H), 7.55 (br s, 1H), 7.52 (d, J=2.0 Hz, 1H), 7.45 (dd, J=8.3, 2.0 Hz, 1H), 7.40 (dd, J=8.8, 2.2 Hz, 1H); LC-MS (MH$^+$=507/509).

Step 3: Preparation of N-{3-[2-(2,4-Dichloro-benzoyl)-3-trifluoromethyl-benzofuran-6-yl]-phenyl}-acetamide

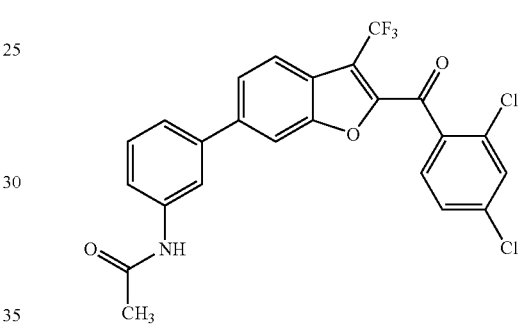

To a solution of trifluoro-methanesulfo4nic acid 2-(2,4-dichloro-benzoyl)-3-trifluoromethyl-benzofuran-6-yl ester from step 2 (110 mg, 0.217 mmol) in anhydrous N,N-dimethylformamide (2 mL) were added 3-acetamidobenzene boronic acid (58.2 mg, 0.325 mmol, 1.5 eq), potassium carbonate (60.0 mg, 0.434 mmol, 2 eq) and tetrakis(triphenylphosphine)palladium(0) (50 mg, 0.043 mmol, 0.2 eq) under argon. The resulting reaction mixture was degassed for 5 min. and then the reaction was then stirred at 80° C. for 6 h. The mixture was cooled to room temperature then poured into ethyl acetate (10 mL) and water (10 mL). The aqueous layer was extracted with ethyl acetate (2×10 mL), and the combined organic layers were washed with water (2×10 mL), dried over Na$_2$SO$_4$, filtrated, and evaporated in vacuo. The residue was purified by pre-HPLC to afford an yellow solid (19.5 mg, 18.3%) as product. $^1$H-NMR (DMSO-d$_6$): 10.08 (s, 1H), 8.10 to 7.99 (m, 3H), 7.91 (d, J=2.0 Hz, 1H), 7.88 (d, J=8.5 Hz, 1H), 7.81 (dd, J=8.5, 1.7 Hz, 1H), 7.70 (dd, J=8.4, 2.3 Hz, 1H), 7.59 (dt, J=7.6, 2.0 Hz, 1H), 7.47 to 7.37 (m, 2H), 2.06 (s, 3H); LC-MS (MH$^+$=492/494).

Using the method of Example 176 and the appropriate starting materials and reagents, compound Examples 180-181 of Table 1 were similarly prepared.

Example 177

Preparation of N-{3-[2-(2,4-dichlorobenzoyl)-3-methoxymethyl)-1-benzofuran-6-yl]phenyl}methanesulfonamide

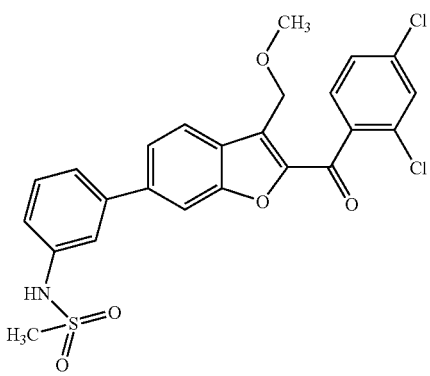

Step 1: Preparation of (6-bromo-3-bromomethyl-benzofuran-2-yl)-(2,4-dichloro-phenyl)-methanone

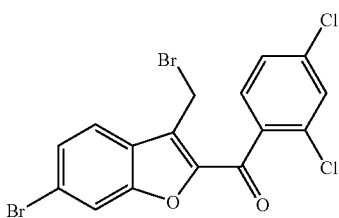

To a solution of (6-bromo-3-methyl-benzofuran-2-yl)-(2,4-dichloro-phenyl)-methanone (3.0 g, 7.81 mmol) in carbon tetrachloride (30 mL) was added N-bromosuccinimide (1.46 g, 8.2 mmol) and 2,2'-azobisisobutyronitrile (128 mg, 0.78 mmol). The reaction mixture was refluxed for 6 h, then filtered. The filtrate was concentrated and the crude product was triturated with 10% EtOAc/hexane to afford the desired product as a pale yellow solid (2.85 g, 78.9%). This material was used in the subsequent step without further purification.

Step 2: Preparation of (6-bromo-3-methoxymethyl-benzofuran-2-yl)-(2,4-dichlorophenyl)methanone

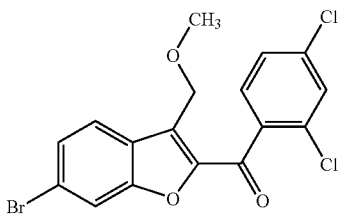

To a solution of (6-bromo-3-bromomethyl-benzofuran-2-yl) -(2,4-dichloro-phenyl)-methanone (1.1 g, 2.3 mmol) in methanol (4 mL) was added 0.5 M sodium methoxide (252 mg, 4.7 mmol). The reaction was stirred at 50 C for 3 h. The solvent was removed at reduced pressure and the mixture was triturated with methanol, providing (227 mg, 23%) a cream colored solid. $^1$H-NMR (CDCl$_3$) δ 7.87-7.37 (m, 6H), 5.00 (s, 2H), 3.47 (s, 3H)

Step 3: Preparation of N-{3-[2-(2,4-dichlorobenzoyl)-3-(methoxymethyl)-1-benzofuran-6-yl]phenyl}methanesulfonamide

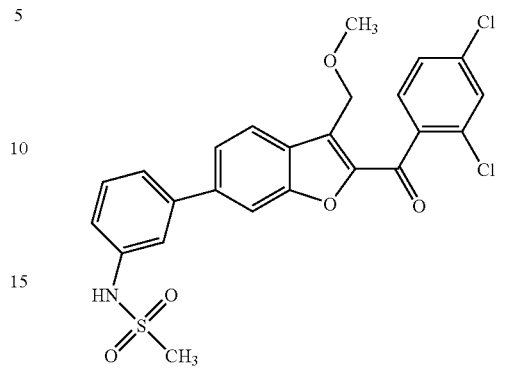

N-{3-[2-(2,4-dichlorobenzoyl)-3-(methoxymethyl)-1-benzofuran-6-yl]phenyl}methanesulfonamide was prepared via a Suzuki coupling of (6-bromo-3-methoxymethyl-benzofuran-2-yl)-(2,4-dichlorophenyl methanone and N-[3-(4,4,5,5-tetramethyl-[1,3,2]dioxaborolan-2-yl-phenyl]-methanesulfonamide as described in method 1 step 5.

Example 183

Preparation of (2,4-dichlorophenyl)(6-pyridin-3-yl-1-benzofuran-2-yl)methanone

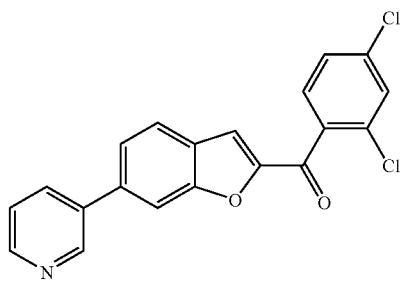

Step 1: Preparation of 4-Iodo-2-hydroxy-benzaldehyde

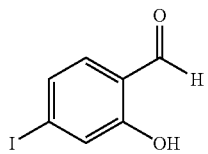

To a solution of 3-iodophenol (3.00 g, 13.6 mmol) in acetonitrile (50 mL) was added magnesium chloride (3.89 g, 40.9 mmol), triethylamine (7.6 mL, 55 mmol), and paraformaldehyde (1.64 g, 55 mmol). The reaction mixture was refluxed overnight, then neutralized with saturated aqueous ammonium chloride. The resultant red precipitate was removed by filtration, and the filtrate was extracted with ethyl acetate. The precipitate was dissolved in methanol and added to the combined organic extracts, which were then dried over magnesium sulfate. The solvent was removed under reduced pressure to provide an orange solid (5.4 g) as the crude product. This material was used in the subsequent step without further purification.

Step 2: Preparation of (2,4-dichloro-phenyl)(6-iodo-benzofuran-2-yl)-methanone

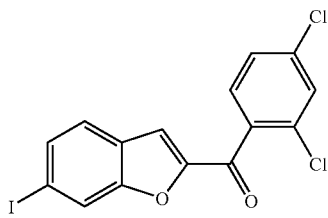

To a solution of 4-iodo-2-hydroxy-benzaldehyde (5.4 g, 22 mmol) and 2-chloro-1-(2,4-dichlorophenyl)ethanone (11.2 g, 50.0 mmol) in anhydrous N,N-dimethylformamide (100 mL) was added $K_2CO_3$ (12.0 g, 86.9 mmol). The dark brown reaction mixture was stirred at 90 C for 48 h, then poured onto water (150 mL) and extracted with ethyl acetate. The solvent was removed under reduced pressure and the residue was purified by column chromatography, eluting with 50% hexanes in dichloromethane. The desired product was obtained as an orange solid (2.06 g, 23%). $^1$H-NMR (CDCl$_3$) δ 7.98 (s, 1H), 7.70 (dd, J=8.3, 1.3 Hz, 1H), 7.54-7.21 (m, 5H).

Step 3: Preparation of (2,4-dichlorophenyl)(6-pyridin-3-yl-benzofuran-2-yl)methanone

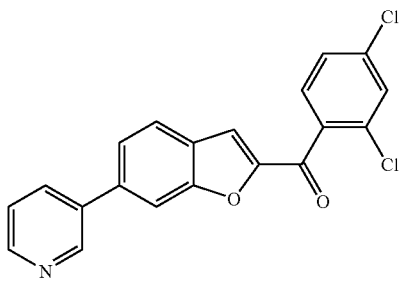

(2,4-Dichlorophenyl)(6-pyridin-3-yl-1-benzofuran-2-yl)methanone was prepared via a Suzuki coupling of (2,4-dichloro-phenyl)-(6-iodo-benzofuran-2-yl)-methanone and pyridine 3-boronoic acid as described in method 1, step 5.

Example 186

Preparation of 3-[2-(2,4-dichlorobenzyl-3-methyl-1-benzofuran-6-yl]benzamide

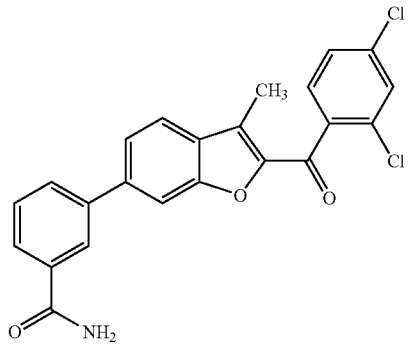

Step 1: Preparation of (2,4-dichlorophenyl)-[3-methyl-6-(4,4,5,5-tetramethyl[1,3,2]dioxaborolan-2-yl)benzofuran-2-yl]-methanone

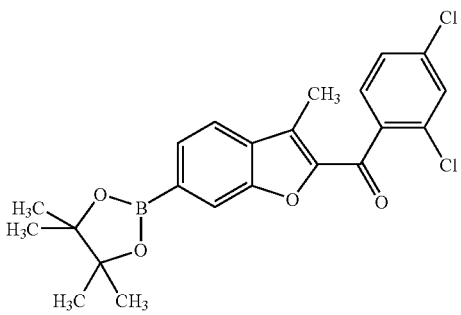

To a solution of (6-bromo-3-methyl-benzofuran-2-yl)-(2,4-dichlorophenyl)-methanone (5.00 g, 13.0 mmol) in dimethylformamide (50 mL) was added bis(pinacolato)diboron (3.94 g, 15.5 mmol), potassium acetate (3.83 g, 39.1 mmol) and [1,1'-bis(diphenylphosphino)-ferrocene]dichloropalladium(II), complex with dichloromethane (1:1) (35 mg, 0.5 mmol). The mixture was degassed under vacuum for 15 min, then heated to 85 C for 4 h. The reaction was diluted with ethyl acetate, washed with water, and concentrated in vacuo. The residue was purified by silica gel chromatography, eluting with 0-15% ethyl acetate in hexanes, to afford the desired product as a white solid (4.07 g, 73%). $^1$H-NMR (CDCl$_3$) δ 7.92 (s, 1H), 7.70 (q, J=21.3, 7.9 Hz, 2H), 7.49 (d, J=2.0 Hz, 1H), 7.46-7.44 (m, 1H), 7.36 (ddd, J=8.2, 1.9, 0.6 Hz, 1H), 2.61 (s, 3H), 1.36 (s, 12H).

Step 2: Preparation of 3-[2-(2,4-dichlorobenzyl-3-methyl-1 benzofuran-6-yl]benzamide

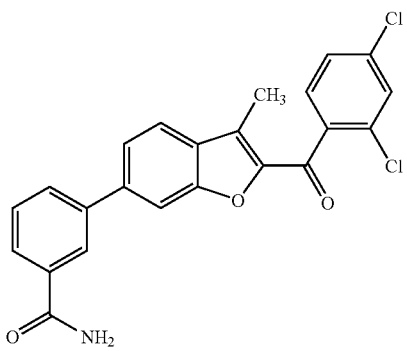

To a solution of (2,4-dichlorophenyl)[3-methyl-6-(4,4,5,5-tetramethyl[1,3,2]dioxaborolan-2-yl)-benzofuran-2-yl]-methanone (100 mg, 0.23 mmol) in toluene (4 mL) and ethanol (4 mL) was added 3-bromobenzamide (56 mg, 0.28 mmol) followed by [1,1'-bis(diphenylphosphino)ferrocene]dichloro-palladium (II), complex with dichloromethane (1:1) (17 mg, 0.02 mmol) and 2M aqueous $Na_2CO_3$ (0.29 mL, 0.58 mmol). The mixture was degassed under vacuum, then heated to 85 C for 2 h. The reaction mixture was concentrated in vacuo, diluted in methanol, and filtered through a syringe filter. Purification by prep-HPLC provided the desired material as a white solid (41.3 mg, 42%). $^1$H-NMR (CDCl$_3$) δ 8.02 (t, J=1.9 Hz, 1H), 7.71-7.67 (m, 3H), 7.61 (m, 1H), 7.52 (dd, J=1.4, 8.4 Hz, 1H), 7.46 (t, J=7.7 Hz, 1H), 7.43 (d, J=2.0 Hz, 1H), 7.39 (m, 1H), 7.31 (ddd, J=8.1, 1.9, 0.2 Hz, 1H), 2.54 (s, 3H).

Example 187

Preparation of 3-[2-(2,4-dichlorobenzoyl)-3-methyl-1-benzofuran-6-yl]-N-(2-methoxyethyl)benzamide

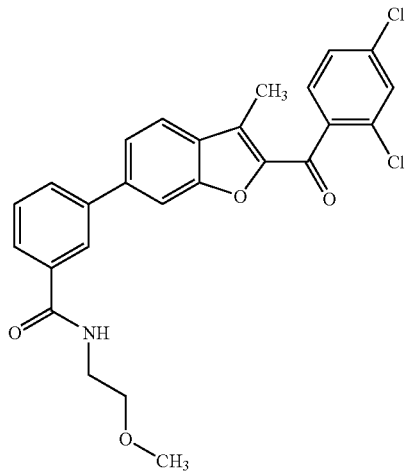

To a solution of 3-[2-(2,4-dichloro-benzoyl)-3-methyl-benzofuran-6-yl]-benzoic acid (40 mg, 0.09 mmol) in dichloromethane (2 mL) was added 2-methoxyethylamine (0.02 mL, 0.19 mmol), EDCI (20 mg, 0.1 mmol), DMAP (1 mg, 0.01 mmol), and N,N-diisopropylethylamine (0.02 mL, 0.1 mmol). The reaction mixture was stirred at rt overnight, then concentrated in vacuo and purified by prep-HPLC to afford the desired product (11 mg, 25%). $^1$H-NMR (CDCl$_3$) δ 8.05 (t, J=1.8 Hz, 1H), 7.77-7.75 (m, 3H), 7.69 (m, 1H), 7.60 (dd, J=8.3, 1.0 Hz, 1H), 7.51 (m, 2H), 7.47 (m, 1H), 7.40 (ddd, J=8.2, 1.9, 0.5 Hz, 1H), 6.62 (t, J=4.5 Hz, 1H), 3.70 (m, 2H), 3.60 (m, 2H), 3.40 (s, 3H), 2.62 (s, 3H).

Example 190

Preparation of (2,4-dichlorophenyl){6-[3-({[2-(dimethylamino)ethyl]amino}methyl)phenyl]-3-methyl-1-benzofuran-2-yl}methanone

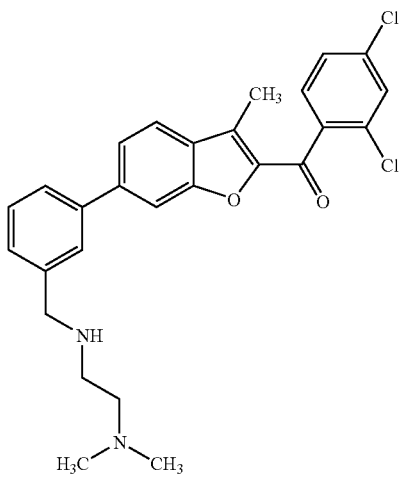

To a solution of (2,4-dichloro-phenyl)-[6-(3-hydroxymethyl-phenyl)-3-methyl-benzofuran-2-yl]-methanone (100 mg, 0.24 mmol) in dichloromethane (5 mL) at 0° C. was added triethylamine (0.05 mL, 0.36 mmol), followed by methanesulfonyl chloride (0.03 mL, 0.36 mmol). After stirring at 0° C. for 1 h, the mixture was quenched with water and extracted with dichloromethane. The combined organic layers were dried over sodium sulfate, filtered, and concentrated in vacuo to afford the crude mesylate.

The mesylate was diluted in toluene (5 mL) and treated with N,N-dimethylethylenediamine (0.21 mL, 2.0 mmol), then the mixture was heated at 80 C for 2 h. The reaction was quenched with saturated aqueous sodium bicarbonate and extracted with ether. Purification by prep-HPLC gave the desired product (9.4 mg, 8%). $^1$H-NMR (CDCl$_3$) δ 7.64 (d, J=8.1 Hz, 1H), 7.59 (m, 1H), 7.52-7.49 (m, 2H), 7.43-7.40 (m, 2H), 7.39-7.34 (m, 1H), 7.31-7.29 (m, 2H), 7.26-7.24 (m, 1H), 7.16 (d, J=0.4 Hz, 1H), 3.80 (s, 2H), 2.65 (t, J=5.8 Hz, 2H), 2.52 (s, 3H), 2.37 (t, J=6.4 Hz, 2H), 2.13 (s, 6H).

Example 194

Preparation of N-{3-[2-(2,4-Dichloro-benzoyl)-3-methoxy-benzofuran-6-yl]-phenyl}-methanesulfonamide

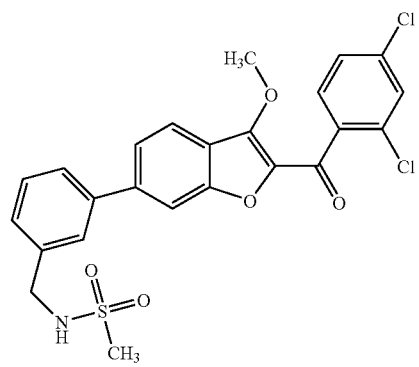

Step 1: Preparation of the starting material: 2,4-dichloro-benzoic acid 2-acetyl-5-bromo-phenyl ester

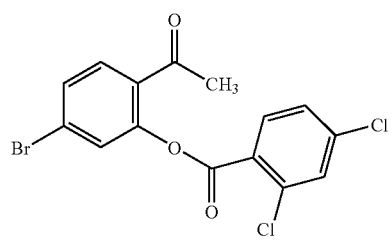

Triethylamine (14.6 mL, 104.6 mmol) was added to a solution of 1-(4-Bromo-2-hydroxy-phenyl)-ethanone (15.0 g, 96.8 mmol) dissolved in dichloromethane (200 mL). The resulting solution was cooled to 0° C. at which time 2,4-dichloro-benzoyl chloride, dissolved in 50 mL dichloromethane was added dropwise over 30 minutes. The resulting mixture was allowed to warm to ambient temperature and stir at this temperature for an additional 16 hours. After this time, the reaction mixture was concentrated via rotary evaporation and then dissolved in EtOAc and washed twice with water and once with a saturated NaHCO$_3$ solution. The organic portion was dried (MgSO$_4$), filtered and concentrated to give the desired product (22.7 g, 84%) which was used without further purification. ¹H-NMR (DMSO) δ 8.18 (d, 1H), 7.96 (d, 1H), 7.82 (s, 1H), 7.64 (m, 3H), 2.53 (s, 3H).

Step 2: Preparation of the intermediate: 6-Bromo-2-(2,4-dichloro-benzoyl)-benzofuran-3-one

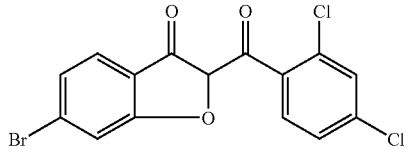

To a stirred solution of 2,4-dichloro-benzoic acid 2-acetyl-5-bromo-phenyl ester (30.0 g, 77.3 mmol) in Dioxane/MeCN/THF (1/1/1 120 mL) was added [hydroxy(tosyloxy) iodo]benzene (HTIB) (30.3 g, 77.3 mmol). The resulting mixture was refluxed for 6 hours at which time additional HTIB (1 g) was added and the mixture was refluxed for an additional 14 hours. The reaction mixture was cooled to ambient temperature and the solvents removed via rotary evaporation. The crude reaction oil was partially recrystallized from EtOH giving an oily solid (12.0 g) which was reacted without further purification by dissolving in THF (200 mL), adding KOH (2.4 g, 43.0 mmol) and heating to reflux. The reaction mixture was heated at this temperature for 1 hour at which time it was cooled and then acidified with dilute H₂SO₄ providing some yellow crystals after filtration. Additional material (2.50 g, 30%) was obtained by column chromatography (10% MeOH/Dichloromethane) to give the title compound as a slightly impure yellow solid. (M+H) 384.9 RT=3.79 min Step 3: Preparation of the starting material: (6-Bromo-3-methoxybenzofuran2yl) (2,4-dichloro-phenyl)-methanone

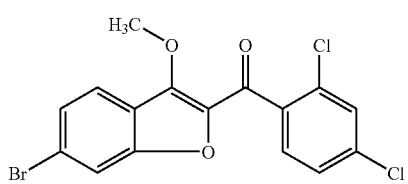

To a solution of 6-Bromo-2-(2,4-dichloro-benzoyl)-benzofuran-3-one (3.30 g, 8.55 mmol) in acetone (50 mL) was added dimethyl sulfate (1.19 g, 9.40 mmol) and cesium carbonate (4.18 g, 12.82 mmol). The resulting mixture was heated at 50 deg for 6 hours is at which time the reaction mixture was concentrated via rotary evaporation. The resulting mixture was taken up in EtOAc and washed twice with water and one time with a saturated sodium carbonate solution. The organic portion was dried over MgSO4 and then filtered and concentrated. The resultant oil was purified via column chromatography (10% MeOH/Dichloromethane) to provide the title compound (950 mg, 28%). ¹H-NMR (CDCl₃): δ 8.03 (d, 1H), 7.65 (d, 1H), 7.46 (m, 2H), 7.35 (m, 2H), 2.46 (s, 3H).

Step 4: Preparation of N-{3-[2-(2,4-Dichloro-benzoyl)-3-methoxy-benzofuran-6-yl]-benzyl}-methanesulfonamide

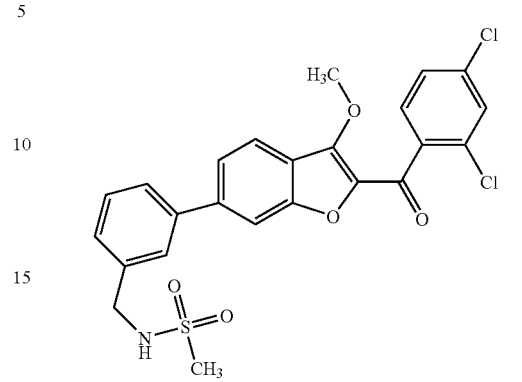

(6-Bromo-3-methoxybenzofuran2-yl)(2,4-dichloro-phenyl) methanone (110 mg, 0.264 mmol), prepared as described above was dissolved in toluene/ethanol (1:1 8 mL). To this solution was added N-[3-(4,4,5,5-tetramethyl-[1,3,2]dioxaborolan-2-yl)-benzyl]-methanesulfonamide (99 mg, 0.317 mmol) and aqueous sodium carbonate (2M, 1.59 mmol). The mixture was degassed with nitrogen for 30 minutes and then Pd(dppf)₂Cl2 (19.32 mg, 0.03 mmol) was added. The resultant mixture was heated at 85 deg C for 18 hours at which time it was cooled to ambient and concentrated via rotary evaporation. The oil thus obtained was diluted with EtOAc and washed with water and brine and dried over MgSO₄. The organic layer was filtered and concentrated and purified by HPLC to give the desired compound (40.4 mg, 29%) ¹H-NMR (CDCl₃): δ 7.84 (d, 1H), 7.63-7.25 (m, 9H), 4.85 (br t, 1H), 4.40 (d, 2H), 4.24 (s, 3H), 2.95 (s, 3H), (M+H) 506.1 RT=3.66 min.

Example 199

Preparation of N-Carbamoylmethyl-2-{3-[2-(2,4-dichloro-benzoyl)-3-methyl-benzofuran-6-yl]-phenyl}acetamide

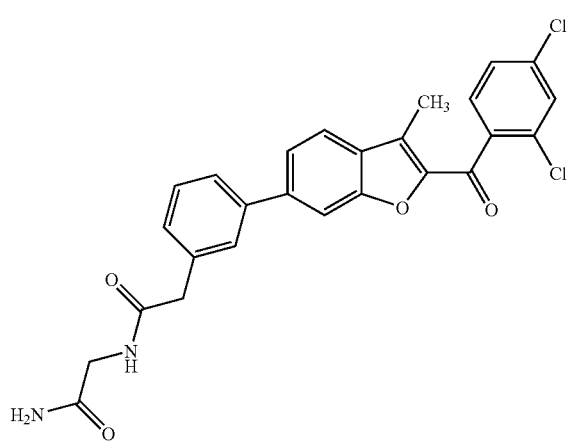

Step 1 Preparation of (3-Bromo-phenyl)-acetic acid methyl ester

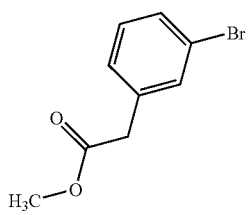

3-bromophenylacetic acid (10000 mg, 46.50 mmol) was dissolved in methanol (200 mL) at room temperature and concentrated hydrochloric acid (4 mL) was added. The resulting solution was heated at 58° C. for 2 h then cooled to room temperature at which time the volatiles were removed in vacuo. The crude material was dissolved in ethyl acetate and the solution was carefully poured into a saturated aqueous sodium bicarbonate solution. The phases were separated and the combined organic extracts were dried over magnesium sulfate and concentrated under reduced pressure. The crude product was purified by MPLC (Biotage) with a gradient of 4 to 35% AcOEt/hexanes to give (3-bromo-phenyl)-acetic acid methyl ester as a colorless oil (10250 mg, 96%). GC-MS (MH+230 RT=9.34 min).

Step 2 Preparation of {3-[2-(2,4-Dichloro-benzoyl)-3-methyl-benzofuran-6-yl]-phenyl}-acetic acid methyl ester

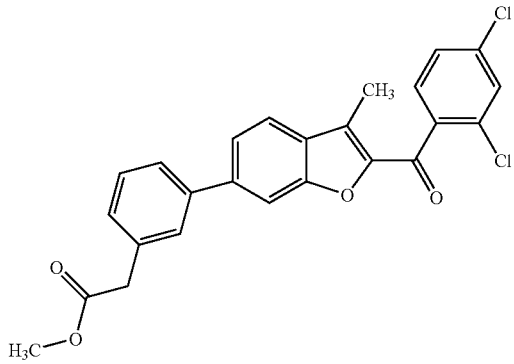

{3-[2-(2,4-Dichloro-benzoyl)-3-methyl-benzofuran-6-yl]-phenyl}-acetic acid methyl ester was prepared via a Suzuki coupling of (6-Bromo-3-methyl-benzofuran-2-yl)(2,4-dichloro-phenyl)-methanone and 3-Bromo-phenyl)-acetic acid methyl ester as described in method 1 step 5. MS ES (MH+) 453.1, RT=4.27 min).

Step 3 Preparation of {3-[2-(2,4-Dichloro-benzoyl)-3-methyl-benzofuran-6-yl]-phenyl}-acetic acid

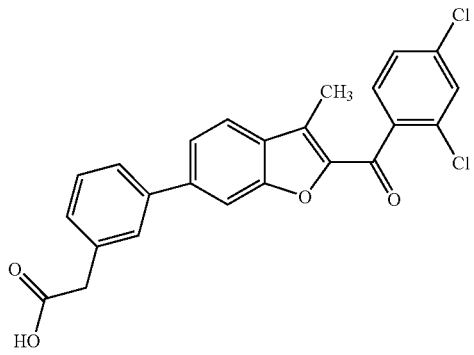

{3-[2-(2,4-Dichloro-benzoyl)-3-methyl-benzofuran-6-yl]-phenyl}-acetic acid methyl ester (3160 mg, 6.97 mmol) was dissolved in tetrahydrofuran (50 mL), methanol (20 mL), water (10 mL), and lithium hydroxide (2650 mg, 110.65 mmol) was added to the solution. The mixture was heated at 50° C. for 3 h then cooled to room temperature. The volatile components were removed under vacuum and the pH of the resulting aqueous component was adjusted to 1 with HCl (1N). The aqueous layer was extracted several times with ethyl acetate and the combined organic extracts were dried over magnesium sulfate and condensed under reduced pressure. The crude residue was purified by MPLC with a gradient of 0 to 30% methanol/dichloromethane to give {3-[2-(2,4-dichloro-benzoyl)-3-methyl-benzofuran-6-yl]-phenyl}-acetic acid as a brown solid (2540 mg, 52% two steps). MS LC-MS (MH+ 439.1/441.1).

Step 4 Preparation of N-Carbamoylmethyl-2-{3-[2-(2,4-dichloro-benzoyl)-3-methyl-benzofuran-6-yl]-phenyl}acetamide

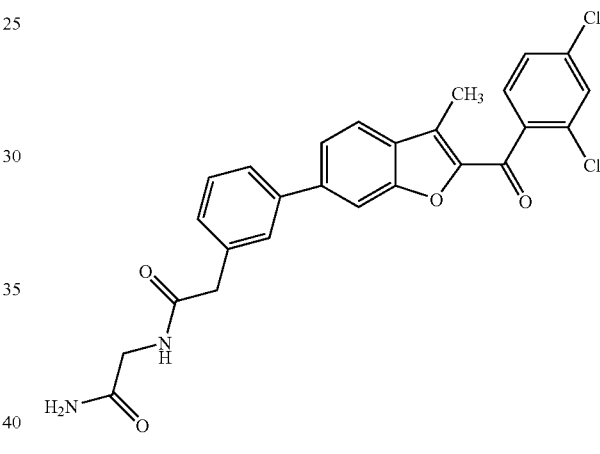

N-Carbamoylmethyl-2-{3-[2-(2,4-dichloro-benzoyl)-3-methyl-benzofuran-6-yl]-phenyl}-acetamide (300 mg, 0.68 mmol), 1-(3-Dimethylaminopropyl)-3-ethylcarbodiimide hydrochloride (143 mg, 0.75 mmol) 1-hydroxybenzotriazole hydrate (110.88 mg, 0.82 mmol) and triethylamine (75.87 mg, 0.75 mmol) were combined and dissolve din N,N-dimethylformamide (3 mL). The resulting mixture was shaken overnight at room temperature. The solvents were evaporated under vacuo and the residue purified by pre HPLC. The fraction containing the pure material were collected and condensed under reduced pressure. The residue was dissolved in dichloromethane and washed with a saturated aqueous sodium bicarbonate solution. The organics were evaporated under reduced pressure to give the N-carbamoylmethyl-2-{3-[2-(2,4-dichloro-benzoyl)-3-methyl-benzofuran-6-yl]-phenyl}-acetamide (95 mg, 28%). MS ES (MH+ 495.0/497.0). $^1$H-NMR (Acetone $d_6$) δ 7.89 (d, J=8 Hz, J=2 Hz, 1H), 7.79-7.78 (m, 1H), 7.78-7.76 (m, 1H), 7.73-7.59 (m, 5H), 7.44-7.36 (m, 3H), 6.92 (br, 1H), 6.45 (br, 1H), 3.84 (d, J=6 Hz, 2H), 3.69 (s, 2H), 2.60 (s, 3H).

Example 200

Preparation of 2-{3-[2-(2,4-Dichloro-benzoyl)-3-methyl-benzofuran-6-yl]-benzylamino}-acetamide

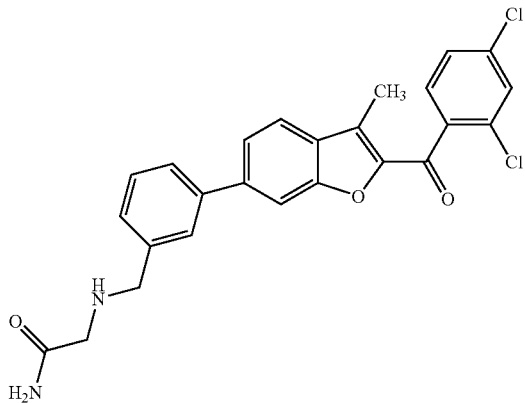

Step 1 Preparation of (2,4-Dichloro-phenyl)-[6-(3-hydroxymethyl-phenyl)-3-methyl-benzofuran-2-yl]-methanone

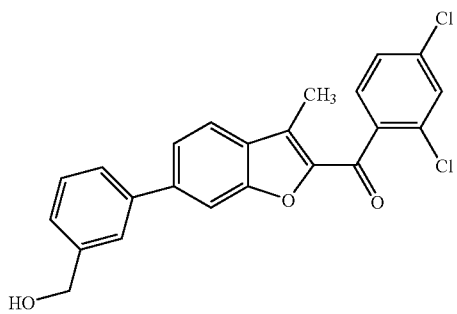

(2,4-Dichloro-phenyl)-[6-(3-hydroxymethyl-phenyl)-3-methyl-benzofuran-2-yl]-methanone was prepared via a Suzuki coupling of (6-Bromo-3-methyl-benzofuran-2-yl)(2,4-dichloro-phenyl)-methanone and 3-(Hydroxymethyl)phenylboronic acid as described in method 1 step 5. $^1$H-NMR (CDCl$_3$) δ 7.62 (d, J=8 Hz 1H), 7.57-7.53 (m, 1H), 7.48 (dd, J=9 Hz, J=2 Hz, 1H), 7.46-7.44 (m, 2H), 7.40 (d, J=2 Hz, 1H), 7.37-7.33 (m, 2H), 7.30-7.26 (m, 2H), 4.68 (s, 2H), 2.51 (s, 3H).

Step 2 Preparation of 2-{3-[2-(2,4-Dichloro-benzoyl)-3-methyl-benzofuran-6-yl]-benzylamino}-acetamide

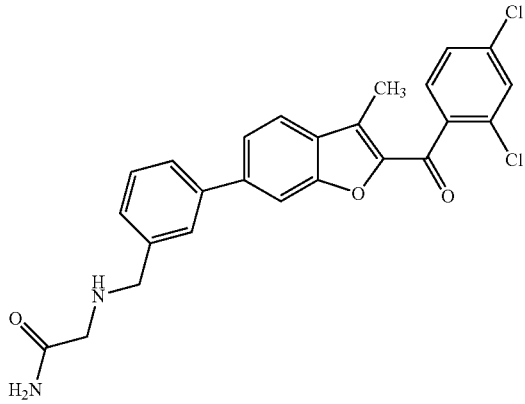

To a solution of (2,4-dichloro-phenyl)[6-(3-hydroxymethyl-phenyl)-3-methyl-benzofuran-2-yl]-methanone (100 mg, 0.24 mmol) in N,N-dimethylformamide (3 mL) at 0° C. was added triethylamine (49.11 mg, 0.49 mmol), lithium iodide (39.04 mg, 0.29 mmol) and methanesulfonyl chloride (33.42 mg, 0.29 mmol). The reaction was aged for 2 h at 0° C. then glycine hydrochloride (40.32 mg, 0.36 mmol) was added to the solution. The reaction mixture was heated overnight at 50° C. after which time the reaction was cooled to room temperature and the volatiles were removed under reduced pressure. The crude residue was purified by pre-HPLC to afford 2-{3-[2-(2,4-Dichloro-benzoyl)-3-methyl-benzofuran-6-yl]-benzylamino}-acetamide as a TFA salt. The material was converted to its free base using aqueous sodium bicarbonate and ethyl acetate to give the title material as a yellowish oil (22 mg, 19%). MS ES (MH+ 467.0/469.0). $^1$H-NMR (Acetone d$_6$) δ 7.92 (dd, J=8 Hz, J=2 Hz, 1H), 7.83-7.82 (m, 1H), 7.81-7.80 (m, 1H), 7.74 (dd, J=8 Hz, J=2 Hz, 1H), 7.70-7.67 (m, 1H), 7.65 (dt, J=7 Hz, J=2 Hz, 1H), 7.62 (d, J=2 Hz, 1H), 7.60 (d, J=2 Hz, 1H), 7.47-7.40 (m, 2H), 7.14 (br, 1H), 6.36 (br, 1H), 3.89 (s, 2H), 3.22 (s, 2H), 2.83 (br, 1H), 2.62 (s, 3H).

Example 209

Preparation of 2-{6-[2-(2,4-Dichloro-benzoyl)-3-methyl-benzofuran-6-yl]-pyridin-2-yl}-acetamide

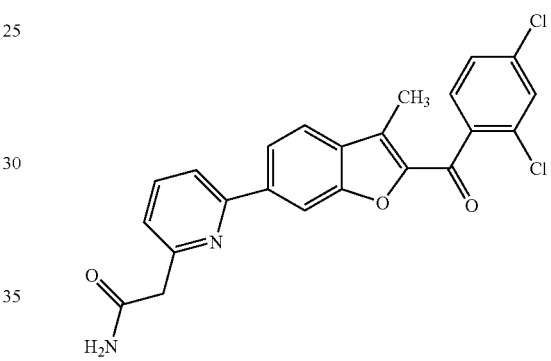

Step 1: 6-Bromo-pyridine-2-carboxylic acid amide

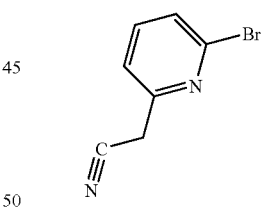

To a solution of (6-Bromo-pyridin-2-yl)-methanol (20.0 g, 106.37 mmol) in N,N-dimethylformamide (200 mL) at 0° c. was added triethylamine (22.2 mL, 159.55 mmol) followed by methanesulfonyl chloride (9.24 mL, 117.01 mmol). The reaction was allowed to stand for 3 hours at which time the reaction was deemed complete. Water was added to the mixture and the entire mixture was extracted with a mixture of 1:1 AcOEt/Hexanes. The combined organic extracts were dried over magnesium sulfate and concentrated in vacuo. The crude material (23400 mg) was dissolved in acetonitrile (50 mL) and potassium cyanide (8311 mg, 127.64 mmol) and 18-crown-6 (14057 mg, 53.18 mmol) were added to the solution. The mixture was heated at reflux for 5 h then cooled to room temperature. The volatiles were removed under reduced pressure and the crude material was dissolved in AcOEt and washed with a saturated aqueous sodium bicarbonate solution. The organic layer was dried over magnesium sulfate and the solvents were removed under reduced pressure. The crude residue was purified by column chromatography eluted with a gradient of 10 to 60% AcOEt/hexanes to give (6-Bromo-pyridin-2-yl)-acetonitrile as a brown solid (12290 mg, 59%). MS ES (MH+ 197.1/199.1).

Step 2: Preparation of 6-Bromo-pyridine-2-carboxylic acid amide

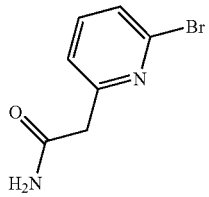

To a solution of (6-bromo-pyridin-2-yl)-acetonitrile (1700 mg, 8.63 mmol) in acetone (60 mL) and water (30 mL) was slowly added sodium percarbonate (16256 mg, 103.53 mmol) portionwise. The reaction mixture was heated at 70° C. for 3 h at which time TLC showed a completed reaction. The phases were separated, and the aqueous layer was extracted several times with ethyl acetate. The combined organic layers were dried over magnesium sulfate and concentrated under reduced pressure. The crude material was purified by pre-HPLC to afford 6-Bromo-pyridine-2-carboxylic acid amide as a yellow solid (733 mg, 40%). MS LC-MS (MH+ 215.0/217.0).

Step 3: Preparation of 2-{6-[2-(2,4-Dichloro-benzoyl)-3-methyl-benzofuran-6-yl]-pyridin-2-yl}-acetamide

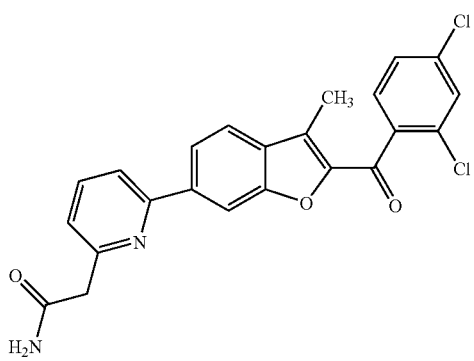

2-{6-[2-(2,4-dichloro-benzoyl)-3-methyl-benzofuran-6-yl]-pyridin-2-yl}-acetamide was prepared via a Suzuki coupling of ((2,4-dichlorophenyl)-[3-methyl-6-(4,4,5, tetramethyl[1,3,2]dioxaborolan-2-yl)-benzofuran-2-yl]-methanone and 6-Bromo-pyridine-2-carboxylic acid amide as described in method 6 step 2. $^1$H-NMR (CD$_3$OD) δ 8.16 (s, 1H), 8.09 (t, J=8 Hz, 1H), 8.03-7.94 (m, 3H), 7.64 (d, J=2 Hz, 1H), 7.57-7.51 (m, 3H), 4.90 (s, 2H), 2.62 (s, 3H).

Example 210

Preparation of N-{6-[2-(2,4-Dichloro-benzoyl)-3-methyl-benzofuran-6-yl]-pyridin-2-ylmethyl}-acetamide

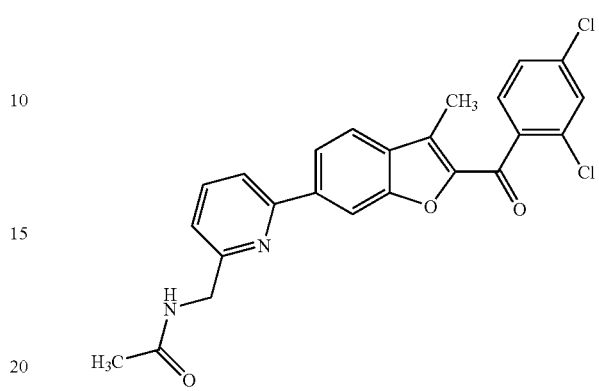

Step 1: Preparation of 6-2-(6-Bromo-pyridin-2-ylmethyl)-isoindole-1,3-dione

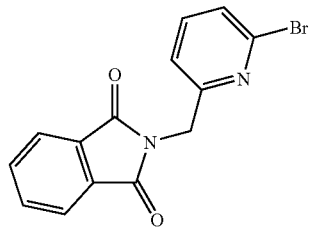

(6-Bromo-pyridin-2-yl)-methanol (2949 mg, 15.68 mmol), phthalimide (3000 mg, 20.39 mmol), triphenylphosphine (5348 mg, 20.39 mmol) and 1,1-(azodicarbonyl)-dipiperidine) 5144, 20.39 mmol) were dissolved in THF (150 mL) and stirred at room temperature for 4 h. The reaction mixture was cooled to 0° C. and the resulting precipitate was removed via filtration. A saturated aqueous sodium bicarbonate solution was added to the filtrate and the solution was extracted several times with ethyl acetate. The combined organic extracts were dried over magnesium sulfate and condensed under reduced pressure. The crude residue was purified by column chromatography with a gradient of 10 to 75% AcOEt/hexanes to give 2-(6-Bromo-pyridin-2-ylmethyl)-isoindole-1,3-dione as a white solid (4000 mg, 80%) MS ES (MH+ 317.2/319.1).

Step 2 Preparation of C-6-Bromo-pyridin-2-yl)-methylamine

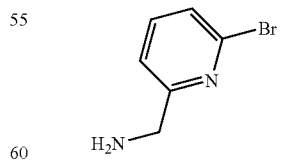

A suspension of 2-(6-Bromo-pyridin-2-ylmethyl)-isoindole-1,3-dione (4000 mg, 12.61 mmol) in ethanol (60 mL) was heated at 70° C. until complete dissolution was observed. Hydrazine hydrate (3156 mg, 63.06 mmol) was then added and the resulting mixture was heated at 70° C. for 5 h. The resulting solution was cooled to 0° C. and filtered. The filtrate was concentrated in vacuo and the crude residue was purified by column chromatography with a gradient of 0 to 30% methanol/dichloromethane to give C-(6-Bromo-pyridin-2-yl)-methylamine as a yellow solid (2070 mg, 79%). MS ES (MH+ 187.1, RT=1.11 min).

Step 3 Preparation of N-(6-Bromo-pyridin-2-ylmethyl)-acetamide

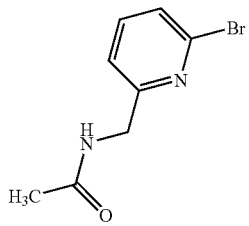

To a solution of C-(6-Bromo-pyridin-2-yl)-methylamine (5440 mg, 29.08 mmol) in dichloromethane (100 mL) at room temperature was added triethylamine (5886 mg, 58.17 mmol) and acetyl chloride (2511 mg, 31.99 mmol). The reaction mixture was heated at 40° C. for 3 h and cooled down to room temperature. A solution of sodium hydroxide (1N) was added and the reaction was stirred for 1 h at room temperature. The layers were separated and the organic phase was concentrated under reduced pressure. The crude mixture was dissolved in EtOH (50 mL) and concentrated hydrochloric acid (10 mL) was added. The mixture was stirred for 30 min and benzene was added followed by sodium hydroxide pellets until pH 10 was reached. The phases were separated and the organic layer was washed with an aqueous solution of ammonium chloride and the volatiles were removed in vacuo. The crude material was purified by column chromatography with a gradient of 0 to 5% methanol/dichloromethane to give N-(6-Bromo-pyridin-2-ylmethyl)acetamide as viscous orange oil. MS ES (MH+ 229.1/231.0).

Step 4 Preparation of N-{6-[2-(2,4-Dichloro-benzoyl)-3-methyl-benzofuran-6-yl]-pyridin-2-ylmethyl}-acetamide

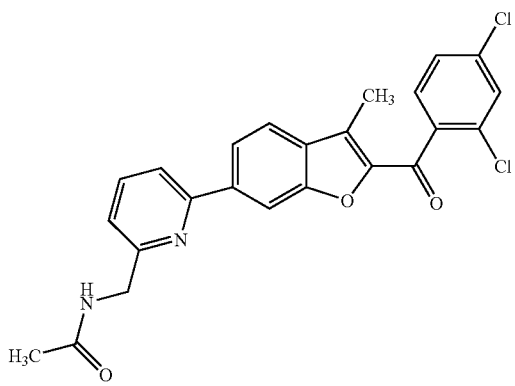

N-{6-[2-(2,4-dichloro-benzoyl)-3-methyl-benzofuran-6-yl]-pyridin-2-ylmethyl}-acetamide was prepared via a Suzuki coupling of ((2,4-dichlorophenyl)-[3-methyl-6-(4,4,5,5-tetramethyl[1,3,2]dioxaborolan-2-yl)-benzofuran-2-yl]-methanone and N-(6-Bromo-pyridin-2-ylmethyl)-acetamide as described in method 6 step 2. $^1$H-NMR (CD$_3$OD) δ 8.19 (s, 1H), 8.05 (dd, J=9 Hz, J=2 Hz, 1H), 7.99-7.89 (m, 3H), 7.64 (d, J=2 Hz, 1H), 7.57-7.51 (m, 2H), 7.40 (d, J=7 Hz, 1H), 4.59 (s, 2H), 2.62 (s, 3H), 2.07 (s, 3H).

Example 214

Preparation of 6-[2-(2,4-Dichloro-benzoyl)-3-methyl-benzofuran-6-yl]-pyridine-2-carboxylic acid amide

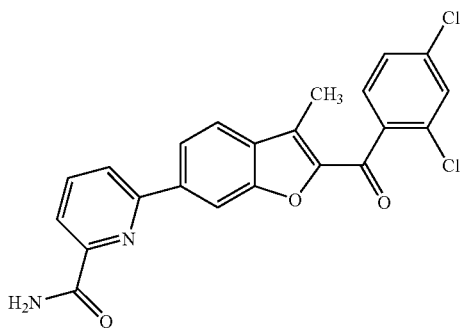

Step 1: 6-Bromo-pyridine-2-carboxylic acid amide

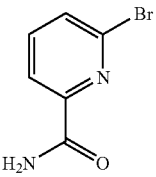

6-Bromopicolinic acid (1000 mg, 4.95 mmol) was suspended in thionyl chloride (15 mL) and heated at 70° C. for 5 h. The reaction was cooled to room temperature and the volatiles were condensed under reduced pressure. A solution of ammonia (2M in dioxane (15 mL) was added to the residue and then the solvents were removed under reduced pressure. The crude residue was purified by MPLC with a gradient of 0 to 20% MeOH/dichloromethane to give 6-Bromo-pyridine-2-carboxylic acid amide as a white powder (555 mg, 45%). MS ES (MH+=201.01203.0).

Step 2: Preparation of 6-[2-(2,4-Dichloro-benzoyl)-3-methyl-benzofuran-6-yl]-pyridine-2-carboxylic acid amide

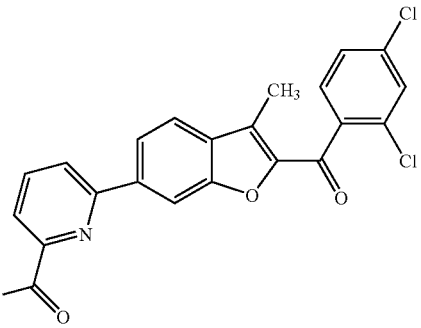

6-[2-(2,4-Dichloro-benzoyl)-3-methyl-benzofuran-6-yl]-pyridine-2-carboxylic acid amide was prepared via a Suzuki coupling of ((2,4-dichlorophenyl)-[3-methyl-6-(4,4,5,5-tetramethyl[1,3,2]dioxaborolan-2-yl)-benzofuran-2-yl]-methanone and 6-Bromo-pyridine-2-carboxylic acid amide as described in method 6 step 2. $^1$H-NMR (CD$_3$OD) δ 8.42 (s, 1H), 8.23-8.17 (m, 2H), 8.09-8.02 (m, 2H), 7.92 (d, J=8 Hz 1H), 7.64 (d, J=2 Hz, 1H), 7.58-7.51 (m, 2H), 2.64 (s, 3H).

Other compounds of formula (I) (including Examples 47-169 of Table 2) may be prepared using the methods described herein or other methods known in the art, by substituting the appropriate starting material(s) and/or intermediate(s) and other reagents, as would be readily recognized by one skilled in the art. The preparation of various starting materials useful for making other compounds of this invention are described further below by way of example and not by way of limitation.

Preparation of Starting Materials

General Method A: 2-Halo-1-arylketones (III)

2-Halo-1-arylketones [e.g., compound (III) of Reaction Schemes 1, 2, 3, etc.] are commercially available, may be prepared as shown in the Reaction Scheme 4 above, and/or may be prepared as specifically described in the experimental Methods A-1 to A-4 below.

Method A-1

Preparation of
2-Bromo-1-(2-bromo-4-fluoro-phenyl)ethanone

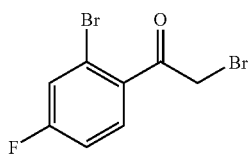

To 1-(2-Bromo-4-fluoro-phenyl)ethanone (2.5 g, 11.52 mmol) in anhydrous tetrahydrofuran (53 mL) under argon was added phenyltrimethylammonium tribromide (4.33 g, 11.52 mmol, 1.0 eq) at 0° C. The reaction mixture was stirred at ambient temperature for 16 h, concentrated, and re-dissolved in ethyl acetate. The organic layer was washed with water (2×150 mL) and brine (1×100 mL), dried (MgSO$_4$), filtered, and evaporated in vacuo. Purification using MPLC chromatography (Biotage) gave 2.14 g (63%) of 2-bromo-1-(2-bromo-4-fluoro-phenyl)-ethanone as a clear oil. $^1$H-NMR (CD$_2$Cl$_2$) δ 7.57 (dd, J=9.6 Hz, 1H), 7.44 (dd, J=8, 2 Hz, 1H), 7.21 (m, 7.21-7.14, 1H), 4.51 (s, 2H); TLC R$_f$=0.38, 15% ethyl acetate-hexanes.

Method A-2

Preparation of
2-Chloro-1-(4-methyl-3-pyridinyl)ethanone
hydrochloride

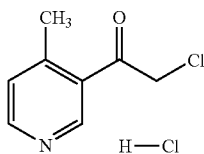

Step 1: Preparation of
1-(4-methyl-3-pyridinyl)ethanone

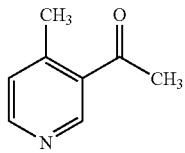

A solution of 3-acetylpyridine (100 g, 0.82 mol), dimethyl sulfide (400 mL, 5.4 mol) and copper (I) iodide (7.94 g, 0.041 mol) in anhydrous THF (2 Lg) was stirred at room temperature under an argon atmosphere. Phenyl chloroformate (0.4 mL, 0.82 mol) was then added, producing a dark brown precipitate. After 30 min, the mixture was cooled below −21° C. and methyl magnesium bromide (1.4 M in 3:1 toluene-THF, 586 mL, 0.82 mol) was added over 50 min, keeping the reaction temperature below −15° C. The color lightened as the mixture became a solution; a lime green precipitate formed near the end of the addition, but re-dissolved upon completion. The mixture was stirred and allowed to warm slowly; after 2 h it had warmed to 8.8° C. Saturated aqueous ammonium chloride solution (500 mL) was added; after stirring 10 min, the mixture was poured into a separatory funnel with water (500 mL). The organic phase was separated, washed with brine (500 mL), dried (Na$_2$SO$_4$), filtered and then concentrated in vacuo. The residue was purified by silica gel chromatography using a hexane-EtOAc gradient to afford 134.3 g (63.7%) of the intermediate dihydropyridine.

A solution of the intermediate dihydropyridine (0.52 mol) in dichloromethane (100 mL) was added to a stirred suspension of sulfur (16.67 g, 0.52 mol) in decalin and slowly heated to reflux under an argon sweep. After refluxing 1 h, the mixture was allowed to cool to room temperature, then filtered through a pad of silica gel. After eluting the decalin with hexane, elution with a hexane-diethyl ether gradient afforded 49.4 g (70.3%) the desired 1-(4-methyl-3-pyridinyl)ethanone as a reddish-brown oil: TLC R$_f$ 0.19 (diethyl ether); TLC R$_f$ 0.14 (1:1 hexane-EtOAc); $^1$H NMR (CD$_2$Cl$_2$) δ 8.9 (s, 1H), 8.5 (d, 1H), 7.2 (dd, 1H), 2.6 (s, 3H), 2.51 (s, 3H); GC MS 135 (M$^+$).

Step 2: Preparation of
2-chloro-1-(4-methyl-3-pyridinyl)ethanone
hydrochloride

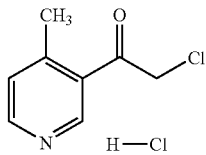

In a 500 mL round bottom flask was placed 1-(4-methyl-3-pyridinyl)ethanone (10.0 g, 74.1 mmol) in 90 mL of Et$_2$O. To this solution was added 88.9 mL of 1M HCl/Et$_2$O (1.2 eq, 88.9 mmol) with stirring and the solution allowed to stir for 1 h at room temperature, at which point, the precipitate was filtered and washed with Et$_2$O. The solid was then dried in vacuo at about 60° C. This HCl salt (12. g, 70.0 mmol) was then dissolved in 70.0 mL of 1M HCl/acetic acid where 9.34 g (1 eq. 70.0 mmol) of N-chlorosuccinimide (NCS) was added and the reaction allowed to stir under Argon at room temperature overnight. At this point, 300 mL of Et$_2$O was added resulting in an off-white precipitate. This was allowed to stir for 1 h at which point the solid was filtered and rinsed with Et$_2$O to provide 12.0 g (83%) of the desired 2-chloro-1-(4-methyl-3-pyridinyl)ethanone hydrochloride. GC/MS RT=6.60 min; $^1$H-NMR (DMSO-d$_6$) δ 2.51 (s, 3H), 5.15 (s, 2H), 7.68 (d, 1H), 8.68 (d, 1H), 9.06 (s, 1H); [M]$^+$169 (95%).

Method A-3

Preparation of 2-chloro-1-[4-(trifluoromethyl)-3-pyridinyl]ethanone hydrochloride

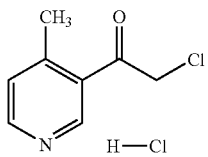

Step 1

In a 250 mL round bottom flask was placed 3.0 g of 4-trifluoronicotinic acid (15.7 mmol, 1 eq) in 100 mL of THF. To this was added 5.3 mL (3.8 g, 37.7 mmol, 2.4 eq) of triethylamine and 9.8 g (18.8 mmol, 1.2 eq) of PyBOP. This was allowed to stir for 10 min at room temperature where 2.7 g of Meldrum's acid (18.8 mmol, 1.2 eq) was added and the reaction allowed to stir at room temperature overnight (18 h). At this point, 30 mL of 1M HCl (aq) was added and the reaction turned immediately from orange to purple. This was then heated at for 18 h gradually turning from purple to yellow. The reaction was then basified with saturated NaHCO$_3$ and extracted with EtOAc (3×200 mL). The combined organics were dried, filtered, and evaporated. The residue was purified via BIOTAGE (35% EtOAc/Hex) to provide methyl 4-trifluoromethylnicotinate 1.84 g (62%) of the desired product as a colorless oil. TLC R$_f$=0.57 (50% EtOAc:Hex).

Step 2

In a 100 mL flask was placed 1.84 g (9.7 mmol, 1 eq) of methyl 4-trifluoromethylnicotinate in 25 mL of 1M HCl in CH$_3$COOH. To this was then added 1.3 g of NCS (9.7 mmol, 1 eq) and the reaction allowed to stir overnight (18 h). The mixture was then transferred to a 500 mL Erlenmeyer flask and to this was added 300 mL of 2 M HCl in Et$_2$O with stirring. This resulted in a white precipitate which was then filtered to provide 1.2 g (49%) of the desired 2-chloro-1-[4-(trifluoromethyl)-3-pyridinyl]ethanone hydrochloride as a white solid. $^1$H-NMR (DMSO-d$_6$) δ 9.21 (s, 1H), 9.02 (d, 1H), 7.94 (d, 1H), 5.19 (s, 2H).

Method A-4

Preparation of 1-Benzo[1,3]dioxol-4-yl-2-bromo-ethanone

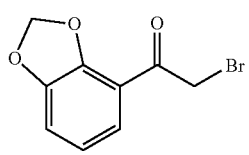

Step 1: Preparation of starting material 1-Benzo[1,3]dioxol-4-yl-ethanone

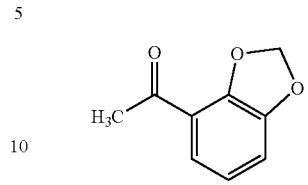

To a solution of MeMgBr in THF (1M, 50 mL, 50 mmol, 1.5 eq) was diluted with 50 mL THF and cooled to −10° C. A solution of benzo[1,3]dioxole-4-carboxaldehyde (5.0 g, 33.3 mmol) in 50 mL THF was slowly added, and the reaction left to stir for 1 h. The reaction mixture was then quenched by pouring it into 500 mL of ice cold sat. ammonium chloride and the mixture extracted with ether. The organic layers were dried over sodium sulfate and filtered through a plug of silica gel before concentrating in vacuo, providing 4.9 g of a white solid. A mixture of this solid (2.0 g, 12.0 mmol) and MnO$_2$ (10.5 g, 120.4 mmol, 10.0 eq) in 75 mL diethyl ether was stirred vigorously for 48 h. The reaction mixture was then filtered first through a plug of silica gel, then through a 0.46 μm frit before concentrating in vacuo to provide 2.1 g of an off-white solid. Purification by MPLC (Biotage) using a hexane-ethyl acetate gradient provided 1.47 g (74%) of 1-benzo[1,3]dioxol-4-yl-ethanone as an off-white solid. $^1$H-NMR (CDCl$_3$) δ 7.35 (d, J=8 Hz, 1H), 6.97 (dm, J=8 Hz, 1H), 6.87 (dd, J=8 Hz, 1H), 6.08 (s, 2H), 2.59 (s, 3H); TLC R$_f$=0.18, 25% ethyl acetate-hexanes.

Step 2: Preparation of Intermediate 1-Benzo[1,3]dioxol-4-yl-2-bromo-ethanone

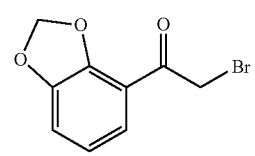

This compound was prepared from 1-benzo[1,3]dioxol-4-yl-ethanone (2.15 g, 13.1 mmol) in the manner described for 2-bromo-1-(2,5-dichlorophenyl)ethanone (Example I-2), affording 1.54 g (48%) of 1-benzo[1,3]dioxol-4-yl-2-bromo-ethanone as an off-white solid. $^1$H-NMR (CD$_2$Cl$_2$) δ; 7.41 (dd, J=8.1 Hz, 1H), 7.05 (dd, J=8.1 Hz, 1H), 6.94 (dd, J=8.8 Hz, 1H), 6.13 (s, 2H), 4.55 (s, 2H). TLC R$_f$=0.28, 15%, ethyl acetate-hexanes.

General Method B: Preparation of Boronate Intermediates (IV)

Aryl boronate intermediates [e.g., compound (IV) in Reaction Schemes 1 and 2, 5, 6, and 7] are either commercially available or may be prepared from the corresponding aryl halide as shown in the Reaction Scheme 5 depicted above, and as specifically described in the experimental procedure B-1 below.

Method B-1

Preparation of 2-[3-(4,4,5,5-Tetramethyl-[1,3,2]dioxaborolan-2-yl)-phenyl]-acetamide

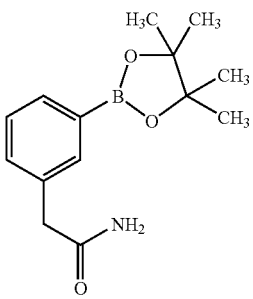

Step 1: Preparation of 2-(3-bromo-phenyl)-acetamide

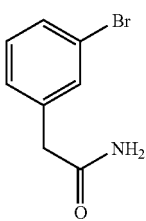

A solution of 3-bromophenylacetonitrile (1.0 g, 5.10 mmol) In acetone (25 mL) and water (15 mL) was treated with sodium percarbonate. The reaction was stirred at 60° C. overnight. The organic solvent was removed at reduced pressure and the residue was diluted with ethyl acetate and water. The layers were separated and the organic was washed with brine and dried over magnesium sulfate. The solvent was removed at reduced pressure and the residue was washed with diethyl ether-hexanes (1/1, v/v) to afford 0.65 g of product (60%) as a white solid. $R_f$=0.18 (silica, ethyl acetate:hexanes, 3:2); $^1$H-NMR (DMSO-$d_6$) δ 7.50 (bs, 1H), 7.46 to 7.39 (m, 2H), 7.26 to 7.22 (m, 2H), 6.93 (bs, 1H), 3.37 (s, 2H).

Step 2: Preparation of 2-[3-(4,4,5,5-Tetramethyl-[1,3,2]dioxaborolan-2-yl)-phenyl]-acetamide A mixture of 2-(3-bromo-phenyl)acetamide (600 mg, 2.8 mmol), potassium acetate (63 mg, 0.28 mmol, 0.1 eq), bis(pinacolato)diboron (783 mg, 3.08 mmol, 1.1 eq), in anhydrous DMF was degassed under $N_2$ for 10 min. Then palladium acetate (824 mg, 8.41 mmol, 3 eq) was added, and the mixture degassed an additional 10 min. The reaction was then heated to 80° C. for 12 h. The reaction mixture was then poured into ethyl acetate and water. Extracted with ethyl acetate (3×20 mL). The combined organic layer was dried with sodium sulfate, filtered through celite pad and concentrated in vacuo. The crude material was used directly to the next step. Yield: (473 mg, 65%). LC-MS (MH$^+$–262).

General Method C: Preparation of Aryl Halide Intermediates

The aryl halides, represented in Reaction Scheme 5 as Ar$^1$-halo where halo is Br or I, and used in the preparation of the aryl boronates (IV) by Method B-1, were either commercially available or prepared as specifically described in the experimental procedures C-1 to C-15 below

Method C-1

Preparation of 1-Bromo-3-methylsulfanylmethyl-benzene

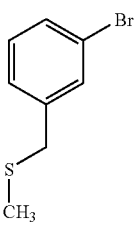

Sodium thiomethoxide (0.616 g, 8.8 mmol) was added to DMF (8 mL) and cooled to 0° C. To this solution was added 1-bromo-3-bromomethyl-benzene (2 g, 8 mmol). The mixture was allowed to warm to rt and stir for 18 h. The mixture was then poured into cold water (50 mL) and extracted with EtOAc (3×20 mL). The organics were combined and dried with sodium sulfate. The solution was concentrated in vacuo to yield the crude product, which was then purified via flash chromatography (5% ethyl acetate-hexanes) to yield 1.3 g (68.5%) of 1-bromo-3-methylsulfanylmethyl-benzene as a pure product. $^1$H-NMR (methylene chloride-d2) δ 7.48-7.47 (m, 1H), 7.392 (dt, J=7.9, 1.5 Hz, 1H), 7.28-7.207 (m, 2H), 3.64 (s, 2H), 1.99 (s, 3H); LC-MS RT: 3.70, [M+H]$^+$: 354.1.

Method C-2

Preparation of 1-Bromo-3-isopropylsulfanyl-benzene

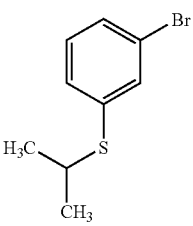

3-Bromobenzenethiol (1 g, 5.3 mmol) was added to acetone (25 mL). Next was added potassium carbonate (1.46 g, 10.58 mmol) and 2-iodopropane (1.17 g, 6.88 mmol). This was refluxed for 5 h. Reaction was then cooled to rt and filtered through a pad of Celite. The organic was then concentrated in vacuo and taken up in ether at which time a white precipitate crashed out. The organic was then re-filtered through the same celite plug and concentrated in vacuo to provide 1.14 g (93.17%) of 1-bromo-3-isopropylsulfanyl-benzene as an oil. 1H-NMR (methylene chloride-d2) δ 7.54 (s, 1H), 7.37-1.31 (m, 2H), 7.18 (t, J-7.9 Hz, 1H), 3.50-3.36 (m, 1H), 1.31 (d, J=6.1 Hz, 6H); LC-MS RT: 4.15, [M+H]$^+$: 233.2.

Method C-3

Preparation of 1-Bromo-3-methylsulfonyl-benzene

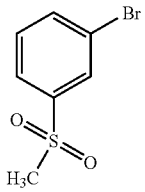

Step 1: Preparation of 1-Bromo-3-methanesulfinyl-benzene

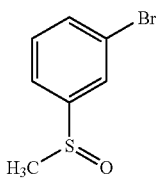

3-Bromothioanisol (0.5 g, 2.46 mmol) was added to methylene chloride (12 mL) and chilled to 0° C. To this was added 3-chloroperoxybenzoic acid (0.467 g, 2.71 mmol). The m-CPBA did not dissolve completely. The mixture was stirred overnight. The reaction was quenched with a saturated sodium thiosulfate (30 mL) solution. The product was extracted with EtOAc (3×20 mL). The organic fractions were combined, washed with brine (20 mL), and dried with sodium sulfate. The organic was then concentrated to yield 0.912 g (81%) 1-bromo-3-methanesulfinyl-benzene. $^1$HNMR (methylene chloride-$d_2$) δ 7.83 (t, J=2.0 Hz, 1H), 7.66 (d, J=7.6 Hz, 1H), 7.57 (d, J=8.3 Hz, 1H), 7.44 (t, J=7.9 Hz, 1H), 2.77 (s, 3H); LC-MS RT: 1.28, [M+H]$^+$: 219.0.

Step 2: Preparation of 1-Bromo-3-methanesulfonyl-benzene

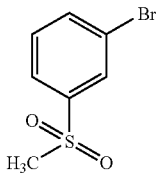

3-Bromothioanisol (8.7 g, 43 mmol) was added to methylene chloride (125 mL) chilled to 0° C. To this was added 3-chloroperoxybenzoic acid (22.2 g, 129 mmol). The m-CPBA did not dissolve completely. The mixture was stirred overnight. The reaction was quenched with a saturated sodium thiosulfate (150 mL) solution. The product was extracted with EtOAc (3×100 mL). The organic fractions were combined, washed with brine (75 mL), and dried with sodium sulfate. The organic was then concentrated to yield 9.89 g (97%) 1-bromo-3-methanesulfonyl-benzene. $^1$HNMR (methylene chloride-$d_2$) δ 8.09 (s, 1H), 7.85 (dd, J=19.2, 7.8 Hz, 2H), 7.50 (t, J=8.2 Hz, 1H), 3.06 (s, 3H); GC-MS RT: 6.49, [M+H]$^+$: 236.0.

Method C-4

Preparation of N-(3-Iodo-benzyl)methanesulfonamide

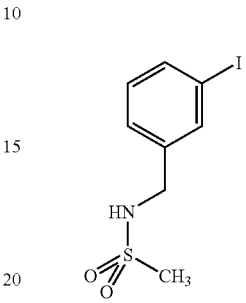

A mixture of 3-iodobenzylamine (1.0 g, 4.29 mmol) and methanesulfonyl chloride (0.35 mL, 4.51 mmol, 1.05 eq) in anhydrous pyridine (2.1 mL) was stirred at 50° C. under argon for 3 days. The cooled reaction was quenched with 1N HCl and diluted with ethyl acetate. The ethyl acetate layer was washed with water, brine, and dried over sodium sulfate. The solvent was removed at reduced pressure, and the crude product was purified on the MPLC (Biotage) eluted with 25% ethyl acetate-hexane. Crystallization from dichloromethane-ether-hexane afforded 1.307 g (97.9%) of the product. 1H-NMR (DMSO-$d_6$) δ 7.68 (s, 1H), 7.60 (ddd, J=7.8 Hz, 1.8 Hz, 1.2 Hz, 1H), 7.55 (t, J=6.3 Hz, is 1H), 7.32 (d, J=9.0 Hz, 1H), 7.80 (t, J=7.8 Hz, 1H), 4.09 (d, J=6.6 Hz, 2H), 2.85 (d, J=1.8 Hz, 3H); LC-MS (ES MH$^+$=264, RT=2.39 min); R$_f$=0.48 (50% ethyl acetate-hexane).

Method C-5

Preparation of 1-(3-Iodo-phenyl)-3-methyl-urea

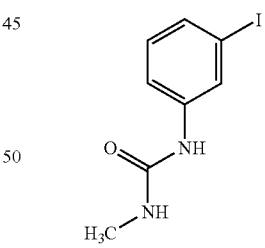

A mixture of 3-iodoaniline (1.0 g, 4.57 mmol) and methylisocyanate (0.29 mL, 5.02 mmol, 1.1 eq) in anhydrous N,N-dimethylformamide (3.0 mL) was stirred at 100° C. under argon for 16 h. The reaction was diluted with ethyl acetate and washed with water, brine, and dried over sodium sulfate. The solvent was removed at reduced pressure, and the crude oil was crystallized from ether-hexane to afford 732.5 mg (58.1%) of the product. $^1$H-NMR (DMSO-$d_6$) δ 8.60 (s, 1H), 7.93 (t, J=1.8 Hz, 1H), 7.25 (ddd, J=8.1 Hz, 2.1 Hz, 0.9 Hz, 1H), 7.20 (ddd, J=8.1 Hz, 2.1 Hz, 0.9 Hz, 1H), 6.98 (t, J=8.1 Hz, 1H), 6.04 (broad d, J=4.8 Hz, 1H), 2.60 (d, J=5.4 Hz, 3H); R$_f$=0.23 (50% ethyl acetate-hexane).

Method C-6

Preparation of (R)-3-(3-Bromo-phenoxy)-propane-1,2-dioll

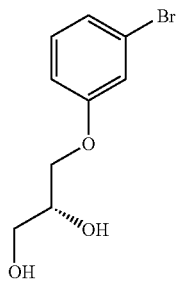

To 3-bromophenol (1.0 g, 5.78 mmol) and (R)-(+)glycidol (428 mg, 5.78 mmol, 1.0 eq) in ethanol (50 mL) was added triethylamine (29 mg, 0.29 mmol, 0.05 eq), and the reaction mixture was refluxed under argon for 3 h. The reaction mixture was cooled and poured into ethyl acetate and water. The organic layer was washed with water, brine, and dried over sodium sulfate. The solvent was removed at reduced pressure, and the crude product was purified on the MPLC (Biotage) eluted with 30% ethyl acetate-hexane to give the diol as a white solid (1.20 g, 84.0%). $^1$H-NMR (Acetone-$d_6$) δ 7.23 (t, J=8.4 Hz, 1H), 7.11 (m, 2H), 6.95 (m, 1H), 4.12 (m, 2H), 3.98 (m, 2H), 3.80 (m, 1H), 3.65 (m, 2H); $R_f$=0.12 (30% ethyl acetate-hexane).

Method C-7

Preparation of 2-fluoro-3-iodo-pyridine

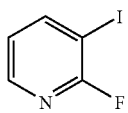

To a solution of n-butyllithium in hexanes (40.14 mL, 1.6 M) under argon at −78° C. was added diisopropylamine (6.5 g, 64.2 mmol, 1.0 eq). After stirring for 30 min at −78° C., a solution of 2-fluoropyridine (6.23 g, 64.2 mmol, 1.0 eq) in anhydrous THF (50 mL) was added. The reaction mixture was stirred at −78° C. for 4 h. Iodine (16.3 g, 64.2 mmol, 1.0 eq) was then added, and the reaction mixture was stirred at −78° C. for another 30 min. The reaction was hydrolyzed with 10% water-THF, and diluted with ethyl acetate and water. The organic layer was washed with water, brine, and dried. The solvent was evaporated under reduced pressure, and the crude product was purified on a MPLC (Biotage) eluted with 20/8020 v/v ethyl acetate-hexane to give 2-fluoro-3-iodo-pyridine as a yellow oil (8.50 g, 59.4%). $^1$H-NMR (Acetone-$d_6$) δ 8.14 (m, 2H), 6.94 (m, 1H); GC-MS (M$^+$=223, RT=9.50 min); $R_f$=0.70 (30% ethyl acetate-hexane).

Method C-8

Preparation of 3-iodo-2-methoxy-pyridine

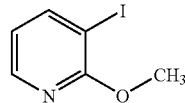

To a solution of sodium methoxide (8.0 mL, 35.9 mmol, 4.0 eq, 25% in methanol) in methanol (60 mL) was added 2-fluoro-3-iodo-pyridine (2.0 g, 8.97 mmol). The reaction mixture was refluxed under argon for 1 h. The reaction mixture was diluted with ethyl acetate and water. The organic layer was washed with water, brine, and dried over sodium sulfate. The solvent was removed at reduced pressure to give 1.8 g (85.4%) of crude product as a yellow oil. $^1$H-NMR (Acetone-$d_6$) 68.16 (m, 2H), 6.78 (m, 1H), 3.93 (s, 3H); LC-MS (ES MH$^+$=236.2); $R_f$=0.75 (30% ethyl acetate-hexane).

Method C-9

Preparation of (3-iodo-pyridin-2-yl)methylamine

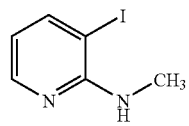

To a solution of 40% methylamine in water (60 mL) was added 2-fluoro-3-iodo-pyridine (2.0 g, 8.97 mmol), and the reaction mixture was refluxed under argon for 4 h. The cooled reaction was diluted with ethyl acetate and water. The organic layer was washed with water, brine, and dried. The solvent was evaporated under reduced pressure to give 1.70 g (81.0%) of crude product. $^1$H-NMR (Acetone-$d_6$) δ 8.06 (dd, J=4.8, 1.5 Hz, 1H), 7.89 (dd, J=7.2, 1.8 Hz, 1H), 6.34 (m, 1H), 5.60 (broad, s, 1H), 2.94 (d, J=4.5 Hz, 3H); $R_f$=0.68 (30% ethyl acetate-hexane).

Method C-10

Preparation of Cyclopropanecarboxylic Acid (3-bromophenyl)amide

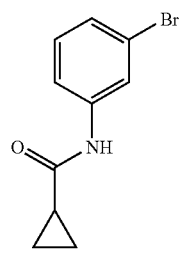

A mixture of 3-bromoaniline (1.0 g, 5.81 mmol), cyclopropane carbonyl chloride (0.61 g, 5.81 mmol, 1.0 eq), and triethylamine (1.17 g, 11.6 mmol, 2.0 eq) in anhydrous THF (20 mL) was stirred at room temperature under argon for 16 h. The reaction mixture was diluted with ethyl acetate and water. The organic layer was washed with water, brine, and dried over magnesium sulfate. The solvent was removed at reduced pressure to afford 1.05 g (75.2%) of the crude product. ¹H-NMR (Acetone-d₆) δ 8.60 (broad s, 1H), 8.07 (dd, J=3.6, 2.1 Hz, 1H), 7.52 (m, 1H), 7.22 (m, 2H), 1.73 (m 1H), 0.90 (m, 2H), 0.80 (m, 2H); MS ES (MH⁺=242); R_f=0.46 (30% ethyl acetate-hexane).

Method C-11

Preparation of 3-Bromo-N-(2-methoxy-ethyl)-benzenesulfonamide

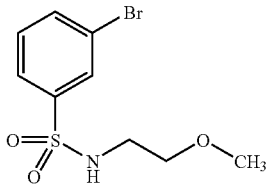

A solution of 3-bromobenzenesulfonyl chloride (1.0 g, 3.72 mmol), 2-methoxyethylamine (0.84 g, 11.15 mmol, 3.0 eq), potassium carbonate (2.57 g, 18.59 mmol, 5.0 eq) in acetone (10.0 mL) was stirred at 40° C. for 4 h. The reaction was diluted with ethyl acetate, washed with water, brine, and dried over magnesium sulfate. The solvent was removed at reduced pressure and purified on the MPLC (Biotage) eluted with 20-25% ethyl acetate-hexane to afford 1.05 g (96%) of the product. R_f=0.33 (silica, ethyl acetate:hexanes, 3:7); ¹H-NMR (DMSO-d₆) δ 7.94 to 7.76 (m, 4H), 7.54 (t, J=7.9 Hz, 1H), 3.27 (t, J=5.6 Hz, 2H), 3.13 (s, 3H), 2.93 (q, J=5.6 Hz, 2H).

Method C-12

Preparation of diethyl-(3-iodo-benzyl)amine

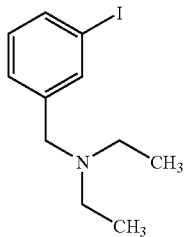

A solution of 3-bromophenacyl bromide (1.0 g, 3.20 mmol), diethylamine (0.70 g, 9.60 mmol, 3.0 eq), potassium carbonate (1.33 g, 9.60 mmol, 3.0 eq) in acetone (10.0 mL) was stirred at 40° C. for 4 h. The reaction was diluted with ethyl acetate, washed with water, brine, and dried over magnesium sulfate. The solvent was removed at reduced pressure and purified on the MPLC (Biotage) eluted with 58% ethyl acetate-hexane to afford 0.92 g (99%) of the product. R_f=0.28 (silica, ethyl acetate:hexanes, 1:9); ¹H-NMR (DMSO-d₆) δ 7.66 (bs, 1H), 7.59 to 7.55 (m, 1H), 7.33 to 7.29 (m, 1H), 7.10 (t, J=7.8 Hz, 1H), 3.47 (s, 2H), 2.42 (q, J=7.1 Hz, 4H), 0.95 (t, J=6.9, 6H).

Method C-13

Preparation of 3-bromo-N-methyl-benzamide

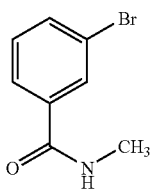

A suspension of methylamine hydrochloride (0.9 g, 13.40 mmol, 3.0 eq) and triethyl amine (2.26 g, 22.33 mmol, 5.0 eq) in anhydrous methylene chloride (10 mL) was cooled to 0° C. The cooled suspension was treated with 3-bromobenzoyl chloride (1.0 g, 4.47 mmol) and then allowed to stir at room temperature for 4 h. The reaction was diluted with ethyl acetate, washed with water, brine, and dried over magnesium sulfate. The solvent was removed at reduced pressure and purified on the MPLC (Biotage) eluted with 35-45% ethyl acetate-hexane to afford 0.60 g (63%) of the product. R_f=0.28 (silica, ethyl acetate:hexanes, 2:3); ¹H-NMR (DMSO-d₆) δ 8.55 (bs, 1H), 7.99 (t, J=1.7 Hz, 1H), 7.83 to 7.79 (m, 1H), 7.73 to 7.69 (m, 1H), 7.42 (t, J=8.0 Hz, 1H), 2.77 (d, J=6.7 Hz, 3H).

Method C-14

Preparation of 2-(3-Bromo-phenyl)propan-2-ol

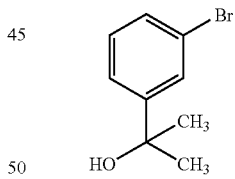

A solution of 3N methylmagnesium bromide (6.53 mL, 19.59 mmol, 3 eq) in diethyl ether was cooled to 0° C. and treated with 3-bromoacetophenone (1.3 g, 6.53 mmol). The reaction was stirred at room temperature for 4 h. The reaction was diluted with ethyl acetate and water. The layers were separated and the organic was washed with saturated sodium bicarbonate, 2N HCl, brine and dried over magnesium sulfate. The solvent was removed at reduced pressure and purified on the MPLC (Biotage) eluted with 5-10% ethyl acetate-hexane to afford 1.2 g (90%) of the product. R_f=0.22 (silica, ethyl acetate:hexanes, 1:9); ¹H-NMR (DMSO-ds) δ 7.63 (t, J=1.8 Hz, 1H), 7.45 to 7.35 (m, 2H), 7.25 (t, J=7.7, 1H), 5.15 (s, 1H), 1.39 (s, 6H).

Method C-15

Preparation of
2-(3-bromo-phenyl)-4,5-dihydro-1H-imidazole

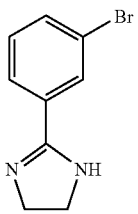

To a solution of 3-bromobenzonitrile (500 mg, 2.75 mmol) in ethylenediamine (3.5 mL) was added sulfur (44 mg, 1.4 mmol). The mixture was refluxed overnight then poured onto ice water, which caused the product to precipitate as a white solid. The product was isolated by vacuum filtration and dried in a vacuum oven (545 mg, 88%). $^1$H-NMR (CDCl$_3$) δ 7.93 (t, J=1.7 Hz, 1H), 7.68 (ddd, J=7.8, 1.2, 1.2 Hz, 1H), 7.56 (dddd, J=7.8, 0.9, 0.9, 0.9 Hz, 1H), 7.26 (dd, J=10.5, 8.0 Hz, 1H), 3.78 (br s, 4H).

It is believed that one skilled in the art, using the preceding information and information available in the art, would know how to make each of the compounds of the to present invention.

Compositions Useful for the Method of this Invention

A compound of formula (I) is useful for treating the conditions described later herein when it is formulated as a pharmaceutically acceptable composition. A pharmaceutically acceptable composition is a compound of formula (I) in admixture with a pharmaceutically acceptable carrier. A pharmaceutically acceptable carrier is any carrier that is relatively non-toxic and innocuous to a patient at concentrations consistent with effective activity of the active ingredient so that any side effects ascribable to the carrier do not vitiate the beneficial effects of the active ingredient.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, CCl$_2$F$_2$, F$_2$ClC—CClF$_2$ and CClF$_3$);

air displacement agents (examples include, but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures);

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered is cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

The compounds of the present invention can be administered with pharmaceutically-acceptable carriers well known in the art using any effective conventional dosage unit forms formulated as immediate, slow or timed release preparations, including, for example, the following.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intranasally, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, Isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example., fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter Into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science & Technology* 1999, 53(6), 324-349; and Nema, S. et al, "Excipients and Their Use in Injectable Products" *PDA Journal of Pharmaceutical Science & Technology* 1997, 51(4), 166-171.

It is believed that one skilled in the art, utilizing the preceding information, can utilize a composition of the present invention to its fullest extent. Nevertheless, the following are examples of pharmaceutical formulations that can be used in a composition of the present invention. They are for illustrative purposes only, and are not to be construed as limiting the invention in any way.

Pharmaceutical compositions according to the present invention can be further illustrated as follows:

Sterile IV Solution: A 5 mg/mL solution of the desired compound of this invention is made using sterile, injectable water, and the pH is adjusted if necessary. The solution is diluted for administration to 1-2 mg/mL with sterile 5% dextrose and is administered as an IV infusion over 60 min.

Lyophilized powder for IV administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 min.

Intramuscular suspension: The following solution or suspension can be prepared, for intramuscular injection:
  50 mg/mL of the desired, water-insoluble compound of this invention
  5 mg/mL sodium carboxymethylcellulose
  4 mg/mL TWEEN 80
  9 mg/mL sodium chloride
  9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate. Soft Gelatin Capsules: A mixture of active ingredient in 8 digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active Ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Hyper-Proliferative Disorders

The compounds and compositions described herein can be used to treat or prevent hyper-proliferative disorders. An effective amount of a compound or composition of this invention can be administered to a patient in need thereof in order to achieve a desired pharmacological effect. A pharmaceutically effective amount of a compound or composition is that amount which produces a desired result or exerts an influence on the particular hyper-proliferative disorder being treated. A patient, for the purpose of this invention, is a mammal, including a human, in need of treatment (including prophylactic treatment) for a particular disorder described further herein.

Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myelold leukemia, acute lymphoblastic leukemia, chronic lymphocytic leukemia, chronic myelogenous leukemia, and hairy cell leukemia.

The disorders described above have been well characterized in humans, but also exist with a similar etiology in other mammals. Accordingly, the method of this invention can be administered to any mammal, including a human, in need thereof for the treatment of proliferative dependent disorders.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere 15 (Bissery et al. *Anti Cancer Drugs* 1995, 6(3), 339), and topoisomerase inhibitors (Edelman et al. *Cancer Chemother. Pharmacol.* 1996, 37(5), 385-93) was demonstrated with the use of in vitro tumor proliferation assays.

The following assay is one of the methods by which compound activity relating to treatment of the disorders identified herein can be determined.

Biological Evaluation of the Invention Compounds

Compounds are tested in a cell based assay that measures the capacity of the compounds to inhibit tumor cell proliferation following a 72 h drug exposure. Cell viability is determined using the Cell Titer-Glo luminescent-cell viability kit from Promega. Briefly, a lysis buffer containing the enzyme luciferase and its substrate, luciferin, is added to each well of the 96 well plate. Upon cell lysis, the ATP released is used to catalyze the metabolism of luciferin, which in turn results in the production of chemiluminescence. The assay is set up such that ATP is the rate-limiting component in the reaction. Since the amount of ATP released into the lysate is directly proportional to the number of viable cells in the well, there is a direct correlation between the amount of luminescence detected and the number of viable cells in each well.

In vitro Tumor Cell Proliferation Assay

The adherent tumor cell proliferation assay used to test the compounds of the present invention involves a readout called Cell Titre-Glo developed by Promega (Cunningham, B A "A Growing issue: Cell Proliferation Assays. Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 8188).

H460 cells (lung carcinoma, purchased from ATCC) are plated in 96-well plates at 3000 cells/well in complete media with 10% Fetal Calf Serum and incubated 24 hours at 37° C. 24 hrs after plating, test compounds are added over a final concentration range of 10 nM to 20 µM in serial dilutions at a final DMSO concentration of 0.2%. Cells are incubated for 72 hours at 37° C. in complete growth media after compound addition. Using the Promega Cell Titer Glo Luminescent assay kit, the number of viable cells/well is determined via measurement of luminescent signal based on amount of intracellular ATP content in cells. Values read at 24-hour incubation are subtracted as Day 0. For determination of IC50's, a linear regression analysis can be used to determine drug concentration which results in a 50% inhibition of cell proliferation using this assay format. Representative compounds of the present invention showed a significant inhibition of tumor cell proliferation in this assay.

Compounds appearing in Table 1, representative of the invention, were tested and demonstrated IC50 values of less than 10 µM in the aforementioned assay.

Based upon the above and other standard laboratory techniques known to evaluate compounds useful for the prevention and/or treatment of the diseases or disorders described above by standard toxicity tests and by standard pharmacological assays for the determination of the prevention and/or treatment of the conditions identified above in mammals, and by comparison of these results with the results of known medicaments that are used to treat these conditions, the effective dosage of the compounds of this invention can readily be determined for prevention and/or treatment of each desired Indication. The amount of the active ingredient to be administered in the prevention and/or treatment of one of these conditions can vary widely according to such considerations as the particular compound and dosage unit employed, the mode of administration, the duration of treatment (including prophylactic treatment), the age and sex of the patient treated, and the nature and extent of the condition to be prevented and/or treated.

The total amount of the active ingredient to be administered will generally range from about 0.001 mg/kg to about 300 mg/kg, and preferably from about 0.10 mg/kg to about 150 mg/kg body weight per day. A unit dosage may contain from about 0.5 mg to about 1500 mg of active ingredient, and can be administered one or more times per day. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of administration and number of doses of a compound or composition of the present invention or a pharmaceutically acceptable salt or ester thereof can be ascertained by those skilled in the art using conventional prevention and/or treatment tests.

The compounds of this invention can be administered as the sole pharmaceutical agent or in combination with one or more other pharmaceutical agents where the combination causes no unacceptable adverse effects. For example, the compounds of this invention can be combined with other anti-hyper-proliferative or other indication agents, and the like, as well as with admixtures and combinations thereof.

For example, optional anti-hyper-proliferative agents which can be added to the composition include but are not limited to compounds listed on the cancer chemotherapy drug regimens in the 11$^{th}$ Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment and/or prevention of neoplasfic diseases in *Goodman and Gilman's The Pharmacologlcal Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of this invention include but are not limited to other anti-cancer agents such as epothilone, irinotecan, raloxifen and topotecan.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein.

What is claimed is:

1. A method of treating a hyper-proliferative disorder in a mammal, comprising administering to a mammal in need thereof an effective amount of a compound of formula (I)

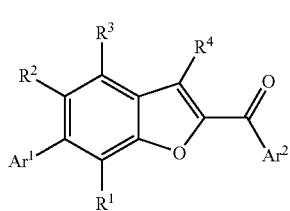

wherein $Ar^1$ is selected from benzodioxolyl, pyrrolidinyl, pyridyl or pyridyl N-oxide, each optionally mono-substituted with $C(O)NH_2$, halo, $(C_1-C_3)$alkoxy, amino, hydroxy$(C_1-C_3)$ alkyl, or $(C_1-C_3)$alkyl optionally substituted with aminocarbonyl or $(C_1-C_3)$alkylcarbonylamino, a five-membered aromatic heterocycle optionally substituted with 1 or 2 substituents each independently selected from $(C_1-C_3)$alkyl, C(O)H, $C(O)(C_1-C_3)$alkyl, and halo, and phenyl optionally substituted with 1 or 2 substituents each selected independently from OH, —$OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $1C(O)R^{10}$, $C(O)NH(C_1-C_3)$alkoxy-$(C_1-C_3)$alkyl, $C(O\ )NH(C_3-C_6)$cycloalkyl, pyrrolidinonyl, imidazolinyl, imidazolidinonyl, $(C_1$—$C_3)$alkoxy optionally substituted with 1 or 2 OH groups, and $(C_1-C_3)$alkyl optionally mono-substituted with CN, OH, $NR^5R^5$, $NHC(O)R^6$, $NHS(O)_2(C_1-C_3)$ alkyl, $C(O)NR^5R^5$, oxazolidinonyl, imidazolidinonyl optionally mono-substituted with $(C_1-C_3)$ alkyl, pyrrolidinonyl optionally mono-substituted with $(C_1-C_3)$alkyl, a five-membered N containing heterocycle optionally mono-substituted with $(C_1-C_3)$alkyl, piperazinyl optionally mono-substituted with $(C_1-C_3)$alkyl, pyridyl optionally mono-substituted with $CF_3$ or $(C_1-C_3)$ alkoxy, thienyl optionally mono-substituted with $C(O)(C_1-C_3)$alkyl, or pyrimidinyl optionally mono-substituted with $NRC[(C_1-C_3)$alkyl$]_2$;

$Ar^2$ is selected from benzodioxolyl, phenyl optionally substituted with 1 or 2 substituents each selected independently from $(C_1-C_3)$alkyl, $(C_1-C_3)$alkoxy, OH, $NO_2$, CN, halo, and $CF_3$, and pyridyl mono-substituted with $(C_1-C_3)$alkyl or $CF_3$;

$R^1$, $R^2$, and $R^3$ are hydrogen;

$R^4$ is selected from hydrogen, $(C_1-C_3)$alkyl, $(C_1-C_3)$ alkoxy, CN, and $C(O)NHR^5$, wherein $(C_1-C_3)$alkyl can optionally be substituted with halo, $(C_1-C_3)$alkoxy, hydroxyalkylamino, alkoxyalkylamino;

$R^5$ is selected from H, $(C_3-C_6)$cycloalkyl, and $(C_1-C_3)$alkyl optionally substituted with 1 or 2 OH groups or mono-substituted with $(C_1-C_3)$alkoxy, $(C_1-C_3)$alkylamino, $S(O)_2(C_1-C_3)$ alkyl, or $C(O)R^7$;

$R^6$ is selected from H, $(C_3-C_6)$cycloalkyl, $(C_1-C_3)$alkoxy, $(C_2-C_6)$alkenyl, $CHF_2$, $CF_3$,$NHR^5$, and $(C_1-C_3)$alkyl optionally substituted with one or more substituents selected from Cl and F, or optionally mono-substituted with $NH_2$ or $NHC(O)(C_1-C_3)$alkyl;

$R^7$ is selected from $(C_1-C_3)$alkoxy, $(C_2-C_6)$alkenyl, $CHF_2$, $CF_3$, $(C_3-C_6)$cycloalkyl, $NR^{7-1}R^{7-1}$, and $(C_1-C_3)$alkyl optionally substituted with one or more substituents selected from Cl and F, or mono-substituted with $NHC(O)(C_1-C_3)$alkyl or $NH_2$, wherein $R^{7-1}$ is hydrogen or $(C_1-C_3)$alkyl;

$R^8$ is selected from $(C_1-C_3)$alkyl and $NR^9R^9$;

$R^9$ is selected from H and $(C_1-C_3)$alkyl optionally mono-substituted with $(C_1-C_3)$alkoxy, or aminocarbonyl, or substituted with 1 or 2 OH groups;

$R^{10}$ is selected from H, $(C_1-C_3)$alkoxy, $NHR^9$, and $(C_1-C_3)$ alkyl optionally mono-substituted with pyrrolidinyl, morpholinyl, pyridinyl, piperazinyl optionally substituted with $(C_1-C_3)$alkyl, or piperidinyl optionally substituted with $(C_1-C_3)$alkyl;

n is 0, 1, or 2;

or a pharmaceutically acceptable salt thereof.

2. The method of claim 1, wherein $Ar^1$ is phenyl optionally substituted with 1 or 2 substituents each selected independently from OH, —$OCF_3$, $CF_3$, CN, halo, $NO_2$, $NR^5R^5$, $NHC(O)R^6$, $NHS(O)_2R^5$, $NHS(O)_2NR^5R^5$, $S(O)_nR^8$, $C(O)R^{10}$, $C(O)NH(C_1-C_3)$alkoxy-$(C_1-C_3)$alkyl, $C(O)NH(C_3-C_6)$cycloalkyl, pyrrolidinonyl, imidazolinyl, imidazolidinonyl, $(C_1-C_3)$alkoxy optionally substituted with 1 or 2 OH groups, and $(C_1-C_3)$alkyl optionally mono-substituted with CN, OH, $NR^5R^5$, $NHC(O)R^6$, $NHS(O)_2(C_1-C_3)$alkyl, $C(O)NR^5R^5$, oxazolidinonyl, imidazolidinonyl optionally mono-substituted with $(C_1-C_3)$alkyl, pyrrolidinonyl optionally mono-substituted with $(C_1-C_3)$alkyl, a five-membered N containing heterocycle optionally mono-substituted with $(C_1-C_3)$alkyl, piperazinyl optionally mono-substituted with $(C_1-C_3)$alkyl, pyridyl optionally mono-substituted with $CF_3$ or $(C_1-C_3)$alkoxy, thienyl optionally mono-substituted with $C(O)(C_1-C_3)$alkyl, or pyrimidinyl optionally mono-substituted with $N[(C_1-C_3)$alkyl$]_2$, $R^5$ is selected from H, $(C_3-C_6)$cycloalkyl, and $(C_1-C_3)$alkyl optionally substituted with 1 or 2 OH groups or mono-substituted with $(C_1-C_3)$alkoxy, $(C_1-C_3)$alkylamino, $S(O)_2(C_1-C_3)$alkyl, or $C(O)R^7$;

$R^6$ is selected from H, $(C_3-C_6)$cycloalkyl, $(C_1-C_3)$alkoxy, $(C_2-C_6)$alkenyl, $CHF_2$, $CF_3$, $NHR^5$, and $(C_1-C_3)$alkyl optionally substituted with one or more substituents selected from Cl and F, or optionally mono-substituted with $NH_2$ or $NHC(O)(C_1-C_3)$alkyl;

$R^7$ is selected from $(C_1-C_3)$alkoxy, $(C_2-C_6)$alkenyl, $CHF_2$, $CF_3$, $(C_3-C_6)$cycloalkyl, $NR^{7-1}R^{7-1}$, and $(C_1-C_3)$alkyl optionally substituted with one or more substituents selected from Cl and F, or mono-substituted with $NHC(O)(C_1-C_3)$alkyl or $NH_2$, wherein $R^{7-1}$ is hydrogen, methyl, or ethyl;

$R^8$ is selected from $(C_1-C_3)$alkyl and $NR^9R^9$;

$R^9$ is selected from H and $(C_1-C_3)$alkyl optionally mono-substituted with $(C_1-C_3)$alkoxy, or aminocarbonyl, or substituted with 1 or 2 OH groups;

$R^{10}$ is selected from H, $(C_1-C_3)$alkoxy, $NHR^9$, and $(C_1-C_3)$ alkyl optionally mono-substituted with pyrrolidinyl, morpholinyl, pyridinyl, piperazinyl optionally substituted with $(C_1-C_3)$alkyl, or piperidinyl optionally substituted with $(C_1-C_3)$alkyl.

3. The method of claim 1, wherein $Ar^1$ is phenyl optionally substituted with $NHS(O)_2R^5$.

4. The method of claim 3, wherein in $R^5$ is $(C_1-C_3)$ alkyl.

5. The method of claim 3, wherein $R^5$ is methyl.

6. The method of claim 1, wherein $Ar^2$ is phenyl optionally substituted with halo.

7. The method of claim 6, wherein halo is chloro.

8. The method of claim 1, wherein $Ar^2$ is 2,4-dihalosubstituted phenyl.

9. The method of claim 1, wherein $Ar^2$ is 2,4-dichlorophenyl.

10. The method of claim 1, wherein $R_4$ is $(C_1-C_3)$alkyl.

11. The method of claim 1, wherein $R_4$ is methyl.

12. The method of claim 1, wherein administering comprises administering parenterally.

13. The method of claim 1, wherein administering comprises administering intravenously.

14. The method of claim 1, wherein the mammal is a human.

15. The method of claim 1 wherein the hyper-proliferative disorder is a solid tumor, lymphoma, sarcoma, or leukemia.

16. The method of claim 1 wherein the hyper-proliferative disorder is a cancer of the breast, respiratory tract, brain, reproductive organs, digestive tract, urinary tract, eye, liver, skin, head and neck, thyroid, parathyroid, and their distant metastases.

17. The method of claim 16, wherein the cancer of the respiratory tract is small-cell lung carcinoma, non-small-cell lung carcinoma, bronchial adenoma, or pleuorpulmonary blastoma.

18. The method of claim 1, wherein administering comprises administering in combination with one or more pharmaceutical agents.

19. The method of claim 18, wherein the one or more other pharmaceutical agents comprise anti-hyper-proliferation agents.

* * * * *

UNITED STATES PATENT AND TRADEMARK OFFICE
CERTIFICATE OF CORRECTION

PATENT NO. : 7,803,956 B2  
APPLICATION NO. : 12/471335  
DATED : September 28, 2010  
INVENTOR(S) : C. Zhang et al.

Page 1 of 3

It is certified that error appears in the above-identified patent and that said Letters Patent is hereby corrected as shown below:

On the Title Page

Item (60)  Related US App. Data

"Continuation of application No. 12/201,547, filed on Aug. 29, 2008, now Pat. No. 7,659,412, which is a division of application No. 10/566,343, filed as application No. PCT/US2004/025480 on Aug. 6, 2004, now Pat. No. 7,420,066."

should read

--Continuation of application No. 12/201,547, filed on Aug. 29, 2008, now Pat. No. 7,659,412, which is a division of application No. 10/566,343, filed Jan. 27, 2006, now Pat. No. 7,420,066, which is a 371 of international application PCT/US2004/025480, filed on Aug. 6, 2004.--

| COLUMN | LINE | ERROR |
|---|---|---|
| 159 | 38 | "selected independently from OH, —$OCF_3$, $CF_3$, CN," |
| (Claim 1) | | should read |
| | | --selected independently from OH, -$OCF_3$, $CF_3$, CN,-- |
| 159 | 41 | "($C_1$-$C_3$)alkyl, C(O )NH($C_3$-$C_6$)cycloalkyl," |
| (Claim 1) | | should read |
| | | --($C_1$-$C_3$)alkyl, C(O)NH($C_3$-C6)cycloalkyl,-- |

Signed and Sealed this  
Twenty-third Day of August, 2011

David J. Kappos  
*Director of the United States Patent and Trademark Office*

CERTIFICATE OF CORRECTION (continued)
U.S. Pat. No. 7,803,956 B2

| COLUMN | LINE | ERROR |
|---|---|---|
| 159 (Claim 1) | 42 | "($C_1$—$C_3$)alkoxy" should read --($C_1$-$C_3$)alkoxy-- |
| 159 (Claim 1) | 45 | "NHS(O)$_2$($C_1$-$C_3$) alkyl" should read --NHS(O)$_2$($C_1$-$C_3$)alkyl-- |
| 159 (Claim 1) | 47 | "($C_1$-$C_3$) alkyl" should read --($C_1$-$C_3$)alkyl-- |
| 159 (Claim 1) | 52 | "($C_1$-C3) alkoxy" should read --($C_1$-$C_3$)alkoxy-- |
| 160 (Claim 1) | 2 | "S(O)$_2$($C_1$—$C_3$) alkyl" should read --S(O)$_2$($C_1$-$C_3$)alkyl-- |
| 160 (Claim 2) | 27 | "each selected independently from OH, —OCF$_3$, CF$_3$," should read --each selected independently from OH, -OCF$_3$, CF$_3$,-- |

CERTIFICATE OF CORRECTION (continued)
U.S. Pat. No. 7,803,956 B2

| COLUMN | LINE | ERROR |
|---|---|---|
| 160 (Claim 2) | 29 | "S(O)$_n$R$^8$, C(O)R$^{10}$, C(O)NHC$_1$ -C$_3$)alkoxy-C$_1$-C$_3$)alkyl," should read --S(O)$_n$R$^8$, C(O)R$^{10}$, C(O)NHC$_1$-C$_3$)alkoxy-C$_1$-C$_3$)alkyl,-- |
| 160 (Claim 2) | 35 | "NHS (O)$_2$(C$_1$ –C$_3$)alkyl," should read --NHS(O)$_2$(C$_1$-C$_3$)alkyl,-- |
| 161 (Claim 10) | 15 | "(C$_i$-C$_3$)alkyl." should read --(C$_1$-C$_3$)alkyl.-- |